United States Patent [19]

Töpfl et al.

[11] Patent Number: 5,201,998
[45] Date of Patent: Apr. 13, 1993

[54] PROCESS FOR SIZING PAPER WITH ANIONIC HYDROPHOBIC SIZING AGENTS AND CATIONIC RETENTION AIDS

[75] Inventors: Rosemarie Töpfl, Dornach; Michael Bernheim, Arlesheim; Hubert Meindl; Hans Wegmüller, both of Riehen; Peter Rohringer, Schönenbuch; Dieter Werthemann, Basel, all of Switzerland

[73] Assignee: Ciba-Geigy Corporation, Ardsley, N.Y.

[21] Appl. No.: 486,679

[22] Filed: Feb. 28, 1990

Related U.S. Application Data

[63] Continuation of Ser. No. 257,132, Oct. 7, 1988, abandoned, which is a continuation of Ser. No. 860,375, May 6, 1986, abandoned, which is a continuation of Ser. No. 497,461, May 23, 1983, abandoned.

[30] Foreign Application Priority Data

| May 28, 1982 | [CH] | Switzerland | 3315/82 |
| Feb. 25, 1983 | [CH] | Switzerland | 1060/83 |
| Mar. 30, 1983 | [CH] | Switzerland | 1754/83 |
| Mar. 30, 1983 | [CH] | Switzerland | 1755/83 |
| Mar. 30, 1983 | [CH] | Switzerland | 1756/83 |

[51] Int. Cl.$^5$ ............................. D21H 17/14
[52] U.S. Cl. ................. 162/158; 162/164.3; 162/164.6; 162/168.2; 162/175; 162/179
[58] Field of Search ............. 162/158, 179, 164.6, 162/168.2, 164.3, 168.3, 175

[56] References Cited

U.S. PATENT DOCUMENTS

| 3,296,065 | 1/1967 | O'Brien et al. | 162/158 |
| 3,652,563 | 3/1972 | Petersen et al. | 162/158 |
| 3,692,885 | 9/1972 | Anello et al. | 162/158 |
| 4,317,756 | 3/1982 | Dumas | 162/158 |
| 4,536,254 | 8/1985 | Falk et al. | 162/158 |
| 4,623,428 | 11/1986 | Bernheim et al. | 162/179 |

FOREIGN PATENT DOCUMENTS

| 2459165 | 6/1976 | Fed. Rep. of Germany | 162/168.2 |
| 867985 | 9/1981 | U.S.S.R. | 162/158 |

*Primary Examiner*—Peter Chin
*Attorney, Agent, or Firm*—Edward McC. Roberts

[57] ABSTRACT

Sizing agents of which some are novel and which have at least one anionic or acidic group which is optionally in the form of a salt and at least two hydrophobic substituents which each have at least 5 carbon atoms, at least two of the most adjacent hydrophobic substituents being bonded to each other with a linking member which has at least 2 hetero atoms, are particularly suitable for use, together with commercially available polymeric, cationic retention aids, in a process for sizing paper or cardboard.

11 Claims, No Drawings

PROCESS FOR SIZING PAPER WITH ANIONIC HYDROPHOBIC SIZING AGENTS AND CATIONIC RETENTION AIDS

This is a continuation of application Ser. No. 257,132 filed on Oct. 7, 1988 abn., which is a continuation of Ser. No. 860,375 filed on May 6, 1986, abandoned, which is a continuation of Ser. No. 497,461 filed May 23, 1983, abandoned.

It is an object of the present invention to make available to the paper manufacturer easily accessible and simply prepared sizing agents which, combined with conventional, cationic retention aids, are suitable for effecting efficient sizing in the production of paper from the dispersions of the fibres.

This object is achieved in a novel manner by using in the production of paper in the presence of polymeric cationic retention aids sizing agents which have at least two long-chain hydrophobic substituents and at least one anionic or acidic group which can be in the form of a salt.

The present invention thus relates to a process for sizing paper or cardboard, which comprises adding to aqueous dispersions of the fibres, which can, if desired, also contain filler, in any order or simultaneously, at least (A) a sizing agent which contains at least one anionic or acidic group which can be in the form of a salt and at least two hydrophobic substituents which each have at least 5 carbon atoms, at least one of the hydrophobic substituents having at least 8 carbon atoms or preferably every hydrophobic group has at least 8 carbon atoms, and at least two of the most adjacent hydrophobic substituents being bonded to each other with a linking member which has at least 2 hetero atoms and preferably at least 1 carbon atom, and (B) a polymeric cationic retention aid.

The invention further relates to the aqueous compositions for carrying out the paper-sizing process which, if the sizing agent (A) and the retention aid (B) are added to the dispersion of the fibres separately in any order, contain, in addition to optional customary additives, the sizing agent (A) alone, which is at least partly in the form of salts, or, if the sizing agent (A) and the retention aid (B) are added to the fibre-bearing liquid simultaneously, contain not only the sizing agent (A) which can be at least partly in the form of a salt but also the retention aid (B) in addition to optional customary additives, the paper or cardboard sized in the process of the invention and the use of a sizing agent A) of the specified type for sizing paper or cardboard.

Some of the representatives of the specified sizing agents (A) are known compounds, while others are novel compounds. The use of the compounds known per se is novel. Where the sizing agents are novel compounds they, together with the process for their preparation, also form part of the subject matter of the present invention.

The sizing agents (A) used in the invention have as an essential feature 1 to 6, above all 1 to 4 preferably 1 or 2, in particular one anionic or acidic group which each generally contain one or two negative charges. For example, acid phosphates

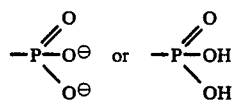

as acidic groups have 2 negative charges, while acid sulfates, $-SO_3^{\ominus}$ or $SO_3H$, or carboxyl groups, $-COO^{\ominus}$ or $-COOH$, only have one negative charge.

In a further embodiment, the sizing agents (A) have preferably 1 or 2 potential anionic, acidic methylene or methine groups. The capacity of anionic or acidic groups to have or be able to form anions in an aqueous medium is a further significant characteristic of the sizing agent. The formation of anions takes place at the pH values of the dispersion of the fibres which are customary in the production of paper. Under said conditions the cationic retention aid (B) form cations. The capacity of the sizing agents and of the retention aids to form anions or cations under paper production conditions can also be referred to as anion-active or cation-active. The anionic sizing agents and the cationic retention aids can also be called anion-active sizing agents and cation-active retention aids respectively.

The sizing agents (A) have as a further characterising feature 2 to 10, preferably 2 to 6, in particular 2 or 3 hydrophobic substituents which only contain the carbon and hydrogen atoms and have at least 5, preferably 8 to 22, in particular 16 to 20, carbon atoms, for example $C_5-C_{12}$-cycloalkyl, $C_6-C_{10}$-aryl, alkaryl or aralkyl radicals. Preferred substituents, however, are open-chain alkyl or alkenyl radicals which generally derive from unsaturated or preferably saturated fatty alcohols, amines or acids having 8 to 22 carbon atoms. The way these hydrophobic substituents are bonded to one another is a further characteristic of the sizing agents (A). The linking members which link at least two of the hydrophobic substituents namely have in a particular embodiment of the sizing agents (A) preferably 4 to 15 carbon atoms and at least 2 hetero atoms, preferably at least two oxygen, and/or nitrogen atoms.

For example, in possible carboxyl or amide radicals

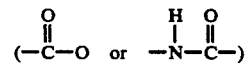

an oxygen or a nitrogen atom as hetero atoms are part of a linking member.

Depending on the number of hydrophobic substituents, the sizing agents contain 1 to 5, preferably 1 to 3, linking members of the specified type.

Preferred linking members generally have one of the formulae $-Q_1-(O)_{n-1}-A_1-(O)_{m-1}-Q_2-$ (1)

or $-O-A_2-O-$, (2)

in which n and m each are 1 or 2, $A_1$ is a divalent aliphatic or cycloaliphatic radical, $A_2$ is a divalent aromatic radical and $Q_1$ and $Q_2$ are different from or, preferably, identical to each other and, if n and m are 1, they are $-NH-$,

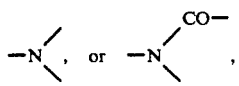

or, if n and m are 2, in particular

n and m preferably being 2.

In formula (1), the radical $A_1$ forms part of an aromatic, preferably aliphatic or cycloaliphatic, bridging member which preferably has 1 or 2, in particular one anionic or acidic group and can have 1 to 5, preferably 1, 2 or 3, nitrogen atoms. Examples of bridging members are those of the formulae

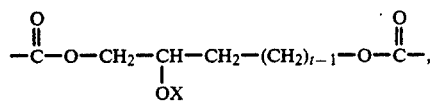

(3)

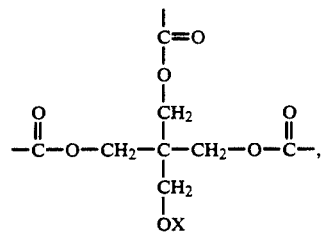

(4)

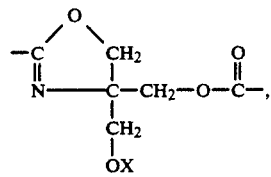

(5)

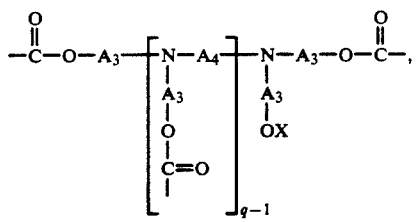

(6)

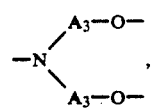

(7)

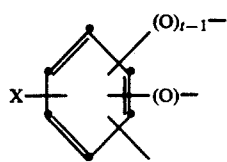

(8),

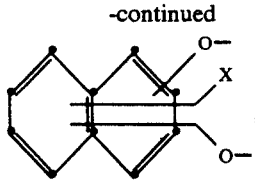

(9)

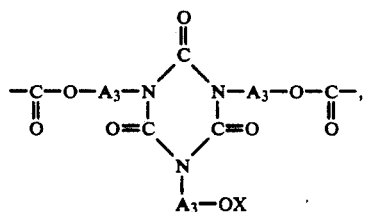

(10)

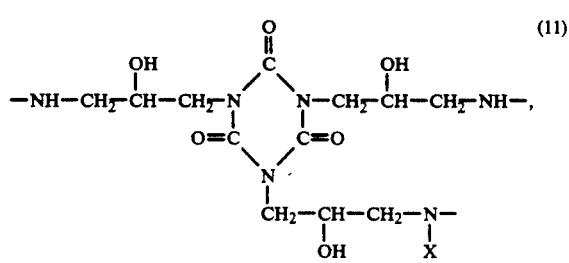

(11)

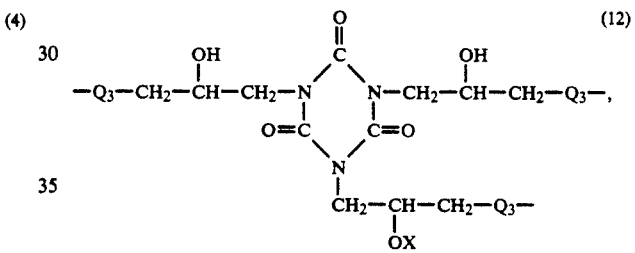

(12)

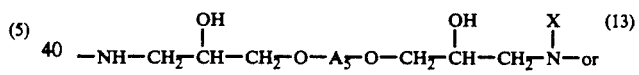

(13)

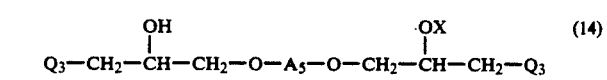

(14)

in which t is 1 or 2, q is an integer from 1 to 5, preferably 1 to 3, $A_3$ and $A_4$ each are propylene, isopropylene or ethylene, $A_5$ is branched or unbranched alkylene having 1 to 6 carbon atoms, X is an anionic or acidic group and $Q_3$ is

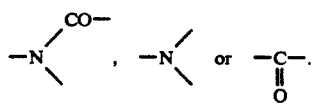 

Of particular importance for use as sizing agent (A) are those which can be obtained by chemical reaction of (a) an aliphatic alcohol which has 3 to 26 carbon atoms and 2 to 6, preferably 2 to 4, hydroxyl or hydroxy-$C_1$–$C_4$-alkyl groups and which can have 1 to 5, preferably 1, 2 or 3, nitrogen atoms and, in the presence of 2 hydroxyl groups, can have a $C_6$–$C_{22}$-, preferably $C_8$–$C_{22}$-, in particular $C_{16}$–$C_{20}$-, fatty amine radical, a heterocyclic alcohol or a glycide which preferably has 3 nitrogen atoms in the hetero ring and 3 hydroxy-$C_1$–$C_4$-alkyl or glycide groups, an alkanedioldiglycide having 2 to 6 carbon atoms in the alkane radical or a diphenol or triphenol or a dihydroxynaphthalene, with (b) a saturated or unsaturated fatty acid or its halides or a primary or secondary fatty amine having 6 to 22, preferably 8 to 22, in particular 16 to 20, carbon atoms in the fatty radical and (c) a polybasic inorganic or organic acid having 2 to 18, preferably 4 to 9, carbon atoms or its anhydrides.

Examples of specific representatives of component (a), from which the sizing agents (A) can be obtained, are as dihydroxynaphthalenes and diphenols or triphenols 1,5-, 1,8-, 2,3- and 2,7-dihydronaphthalene, pyrogallol, hydroxyhydroquinone, phloroglucine, hydroquinone and especially pyrocatechol and resorcinol, as heterocyclic alcohols or glycides especially tris(hydroxyethyl) isocyanurate and isocyanuric acid triglycide as alkanedioldiglycides especially butane-1,4-dioldiglycide, as aliphatic alcohols sorbitol, sorbitan (i.e. cyclic anhydrosorbites obtained from sorbitol by elimination of water), especially butane-1,2,4-triol, glycerol, pentaerythritol, tris(hydroxymethyl)-aminomethane, trialkanolamines, for example triethanolamine, $C_8$–$C_{22}$-fatty amine dialkoxylates, for example laurylamine diethoxylate, and polyhydroxyalkylpolyalkylenepolyamines, for example N,N,N',N'-tetrakis(2-hydroxypropyl)ethylenediamine.

Aliphatic alcohols are preferred for use as component (a) to dihydroxynaphthalenes, diphenols, triphenols, heterocyclic alcohols or glycides or alkanedioldiglycides.

Sizing agents (A) having a bridging member of the formula (3) can be obtained from butane-1,2,4-triol or glycerol, having a bridging member of the formula (4) from pentaerythritol, having a bridging member of the formula (5) from tris(hydroxymethyl)-aminomethane, having a bridging member of the formula (6) from a fatty amine dialkoxylate or polyhydroxyalkylpolyalkylenepolyamine, having a bridging member of the formula (7) from a trialkanolamine, having a bridging member of the formula (8) from a diphenol or triphenol, having a bridging member of the formula (9) from a dihydroxynaphthalene, having a bridging member of the formula (10) from a tris(hydroxyalkyl) isocyanurate, having a bridging member of the formula (11) or (12) from isocyanuric acid triglicide and having a bridging member of the formula (13) or (14) from an alkanedioldiglycide, for use as component (a).

Especially suitable for use as component (b), from which the sizing agents (A) can be obtained, are saturated or unsaturated fatty acids having 6 to 22, preferably 8 to 22, in particular 16 to 20, carbon atoms, halides thereof or, as secondary and especially primary fatty amines, monoalkytamines or dialkylamines or monoalkenylamines or dialkenylamines each having 6 to 22, preferably 8 to 22, in particular 16 to 20, carbon atoms in the alkyl or alkenyl radical. An unsaturated or saturated $C_6$–$C_{22}$-, preferably $C_8$–$C_{22}$--, in particular $C_{16}$–$C_{20}$-, fatty acid for use as component (b) is, for example caproic, preferably caprylic, capric or arachidic acid, in particular lauric, myristic, palmitic, stearic or behenic acid or myristoleic, palmitoleic, elaeostearic, clupanodonic acid, in particular oleic, elaidic, erucic, linoleic or linolenic acid. Of these, lauric, palmitic, stearic, oleic and behenic acid are of particular importance, stearic acid being to the fore in interest. Technical, readily accessible mixtures of the acids just mentioned are also suitable. The unsaturated or preferably saturated fatty acid halides, for example alkyl or alkenyl halides, the monoalkylamines or dialkylamines or monoalkenylamines or dialkenylamines structurally derive from the fatty acids just mentioned. Suitable alkyl or alkenyl halides are especially the chlorides or, in particular, the bromides. Dioctadecylamine, especially octadecylamine and octadecyl bromide, are specifically mentioned as representatives of monoalkylamines or dialkylamines having $C_{16}$–$C_{20}$-alkyl radicals or of alkyl halides because they are readily accessible. Technical mixtures of fatty amines or alkyl halides of the specified type are also suitable.

Specific representatives of component (c) are in particular sulfur trioxide, sulfuric acid, phosphoric acid, trimellitic anhydride, phthalic anhydride, glutaric anhydride and especially chlorosulfonic acid, phosphorus pentoxide, succinic anhydride and maleic anhydride. X in the formulae (3) to (14) is thus preferably one of the acidic groups —CO—$C_6H_4$—COOH, —CO—($CH_2$)$_2$—COOH, —CO—CH=CH—COOH,

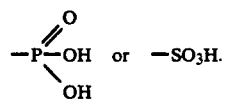

or —$SO_3H$.

The reaction products from the components (a) and (b) are intermediates from which the sizing agents (A) can be obtained by reaction with component (c). A skilled worker will know from the type of component (a) used whether a fatty acid, a fatty amine, a fatty acid anhydride or an alkyl halide or alkenyl halide needs to be used as component (b). If a diphenol, triphenol or a dihydroxynaphthalene is used as component (a), an alkyl halide or alkenyl halide is used as component (b), while if an aliphatic or heterocyclic alcohol is used as component (a), a fatty acid is generally used as component (b). If, however, a heterocyclic glycide or an alkanedioldiglycide is used as component (a), it is possible to use not only fatty amines but also fatty acids.

If a diphenol, a triphenol or a dihydroxynaphthalene is used as component (a), preferably [h] mols of alkyl halide or alkenyl halide are used as component (b) per mol of component (a), [h] denoting the number of hydroxyl groups of component (a). It is thus possible in this case to obtain hydroxyl-free aromatic di- or tri-ethers as intermediates, from which the sizes (A) can be obtained by using 1 to 2, preferably 1 to 1.5, in particular 1, mol(s) of component (c) per mol of starting component (a). Since the reaction with component (c) takes place at the aromatic nucleus of the fatty acid di- or tri-ether, it is advisable to use as component (c) sulfuric acid, sulfur trioxide or, in particular, chlorosulfonic acid. The sizes (A) can accordingly be obtained in one of their preferred embodiments by reacting at least (a) 1 mol of a diphenol, a triphenol or a dihydroxynaphthalene with (b) [h] mols of an alkyl halide or alkenyl halide having 6 to 22, preferably 8 to 22, in particular 16 to 20 carbon atoms, [h] denoting the number of hydroxyl groups of component (a), and (c) 1 to 2, preferably 1 to 1.5, in particular 1, mol(s) of chlorosulfonic acid, component (c) being added last.

If a heterocyclic glycide or an alkanedioldiglycide is used as component (a), preferably [h'] mol(s of a fatty acid and/or of a primary or secondary fatty amine are used, [h'] denoting the number of glycide groups of component (a). In this case it is thus possible to obtain as intermediates heterocyclic compounds or alkanes which have β-hydroxy-γ-(fatty acid)-propyl groups, primary or secondary β-hydroxy-γ-(fatty amino)-propyl groups or β-hydroxy-)γ-bis(fatty amino)-propyl groups or secondary β-hydroxy-γ-(fatty carboxamide)-propyl groups. Heterocyclic compounds as intermediates preferably have 3 such groups and alkanes as intermediates preferably have 2 such groups, which are contained, for example, in the bridging members of the formulae (11) to (14). The sizing agents (A) can be obtained from such intermediates by using 1 to 2, preferably 1 to 1.5, in particular 1, mol(s) of component (c) per mol of starting component (a), any abovementioned, specific representatives of polybasic inorganic or organic acids having 2 to 8 carbon atoms, or anhydrides thereof being possible for use as component (c).

If the intermediate is obtained from component (a) together with a primary fatty amine as component (b), and therefore has primary β-hydroxy-γ-(fatty amino)-propyl groups, the reaction with component (c) generally takes place at the hydrogen atom of the -NH- radical of such groups. However, if the intermediate is obtained from component (a) by means of a fatty acid or a secondary fatty amine, i.e. by means of a dialkylamine or dialkenylamine having 6 to 22 carbon atoms, or by means of a primary fatty amine, i.e. by means of $C_6$–$C_{22}$-alkylamine or -alkenylamine, and has secondary β-hydroxy-γ-(fatty acid ester)-propyl groups, β-hydroxy-δ-bis-(fatty amino)-propyl groups or β-hydroxy-γ-(fatty carboxamido)propyl groups, the reaction with component (c) generally takes place at the hydrogen atom of the β-hydroxyl radical of such groups.

Sizing agents (A) in a further preferred embodiment can thus be obtained by reacting at least (a) 1 mol of a heterocyclic glycide having preferably 3 nitrogen atoms in the hetero ring and 3 glycide groups, in particular isocyanuric acid triglycide, or an alkanedioldiglycide having preferably 2 to 6 carbon atoms in the alkane radical, in particular butane-1,4-dioldiglycide, with (b) [h'] mol(s) of a fatty acid or of a primary or secondary fatty amine each having 6 to 22, preferably 8 to 22, in particular 16 to 20, carbon atoms in the fatty radical, [h'] denoting the number of glycide groups of component (a), and then with (c) 1 to 2, preferably 1 to 1.5, in particular 1, mol(s) of a polybasic inorganic or organic acid having 2 to 8 carbon atoms or anhydrides thereof, component (c) being added last.

If, as preferred, a heterocyclic or aliphatic alcohol is used as component (a), preferably [h-1] mol(s) of a fatty acid are used, [h] denoting the number of hydroxyl groups of component (a). If, for example, an aliphatic alcohol having 2 hydroxyl groups and a fatty amine radical is used as component (a), 1 mol of fatty acid is used as component (b) per mol of component (a). However, if a heterocyclic alcohol having 3 hetero atoms is used as component (a), 2 mols of fatty acid are used as component (b) per mol of component (a). If aliphatic alcohols having preferably 3 or 4 hydroxyl groups are used as component (a), 2 or 3 mols of fatty acid are used as component (b) per mol of component (a). The intermediates obtained from component (a) and (b) if alcohols of the specified type are used as component (a) are partially esterified compounds, i.e. partial esters which still contain a free hydroxyl group. The sizing agents (A) can be obtained from these compounds by using 1 to 2 mols, preferably 1 to 1.5 mols, in particular 1 mol, of component (c) per mol of starting component (a), the component (c) forming an acid ester with the hydroxyl group of the intermediates from (a) and (b) and any abovementioned specific representative of polybasic inorganic or organic acids having 2 to 8 carbon atoms or anhydrides thereof can be used as component (c).

Sizing agents (A) can thus be obtained in their particularly preferred form by reacting at least (a) 1 mol of an aliphatic alcohol which has 3 to 26 carbon atoms, 2 to 6, preferably 2 to 4, hydroxyl groups and can have 1 to 5, preferably 1, 2 or 3, nitrogen atoms and, in the presence of 2 hydroxyl groups, can have a $C_6$–$C_{22}$-, preferably $C_8$–$C_{22}$-, in particular $C_{16}$–$C_{20}$-, fatty amine radical, with (b) [h-1] mol(s) of an unsaturated or preferably saturated fatty acid having 6 to 22, preferably 8 to 22, in particular 16 to 20, carbon atoms or mixtures thereof, [h] denoting the number of hydroxyl groups of component (a), and then with (c) 1 to 2, preferably 1 to 1.5, in particular 1, mol(s) of a polybasic inorganic or organic acid having 2 to 18 carbon atoms or anhydrides thereof, the polybasic acid being used as component (c) being added last and forming acid esters with the hydroxyl groups present in the intermediates formed from components (a) and (b).

Those acid esters which are intended for use as sizes (A) and which can be obtained by reacting intermediates from 1 mol of laurylamine diethoxylate and 1 mol of behenic acid, from 1 mol of glycerol, triethanolamine or tris(hydroxymethyl)aminomethane and 2 mols of stearic acid or an equimolar mixture of stearic acid and palmitic acid or from 1 mol of pentaerythritol or N,N,N',N'-tetrakis(2-hydroxypropyl)ethylenediamine and 3 mols of stearic acid, with 1 to 1.5 mols each of chlorosulfonic acid, phosphorus pentoxide or maleic anhydride, are of particular importance.

To the fore of interest are sizing agents (A) which can be obtained by reacting (a) 1 mol of triethanolamine or, in particular, 1 mol of glycerol with (b) 2 mols of stearic acid and then with (c) 1 mol of phosphorus pentoxide, or, in particular, (a) 1 mol of tris(hydroxymethyl)aminomethane with (b) 2 mols of stearic acid and then with (c) 1 to 1.5 mols of maleic anhydride.

Further sizing agents of interest can be obtained by reacting tensides which are derived from sulfosuccinic acid, e.g. sulfosuccinic isooctyl ester, with a fatty alcohol.

Preferred sizing agents (A) can be obtained from components (a), (b) and (c) or from the tensides of the specified type and have molecular weights of about 400 to about 3,000, preferably of about 600 to 1,500, and an acid value (mg of KOH/g of substance) of about 15 to about 150, preferably 35 to about 125.

As mentioned above, some of the compounds used in the invention as sizing agents and some of the intermediates from which these sizing agents can be obtained are known.

German Patent 733,689, for example, discloses intermediates from triethanolamine and stearic acid which still have at least one free hydroxyl group, which can be esterified with phthalic anhydride. However, this publication discloses no intermediates prepared from two fatty acids which differ from each other. The publication mentions as polybasic acids or anhydrides thereof for preparing the acid esters apart from aromatic acids such as phthalic acid, and its isomers, and naphthalic acid, only tartaric acid and succinic acid.

German Patent 193,189, for example, discloses further intermediates from glycerol and stearic acid which have a free hydroxyl group, which can be esterified with phosphorus pentoxide. Apart from phosphorus pentoxide, this publication mentions no other polybasic acid or anhydride thereof for preparing the acidic esters.

Nor do the German patents mentioned contain any information about using the disclosed compounds as sizing agents for paper.

U.S. Pat. No. 2,504,951, moreover, describes how 2-heptadecyl-bis(4-stearyloxymethyl)-2-oxazoline is prepared from 1 mol of tris(hydroxymethyl)aminomethane and 3 mols of stearic acid. However, this patent contains no information about 2-heptadecyl-4-hydroxymethyl-4-stearoyloxymethyl-2-oxazoline from 1 mol of tris(hydroxymethyl)aminomethane and 2 mols (instead of 3 mols) of stearic acid, nor about using the oxazoline described as a sizing agent for paper.

Reference is finally made to U.S. Pat. No. 2,067,960, which discloses $C_{12}$–$C_{14}$-alkyl diethers of hydroquinone, resorcinol or pyrocatechol, but does not contain any information about reaction products of such ethers with polybasic inorganic or $C_2$–$C_8$ organic acids or their anhydrides or about their use as sizing agents for paper.

Furthermore, the German "Offenlegungsschrift" 2,162,620 discloses the final products which can be obtained from tensides which are derived from sulfosuccinic acid. This reference contains, however, no information about the utility of such products, e.g. as sizing agents for paper.

The invention thus also relates to novel intermediates, from which the sizing agents (A) to be used in the invention can be obtained and which have one of the formulae

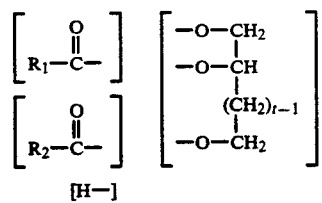 (15)

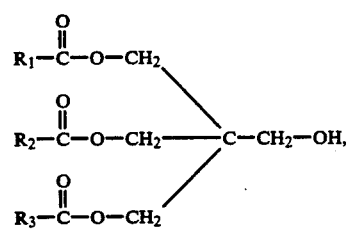 (16)

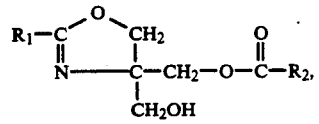 (17)

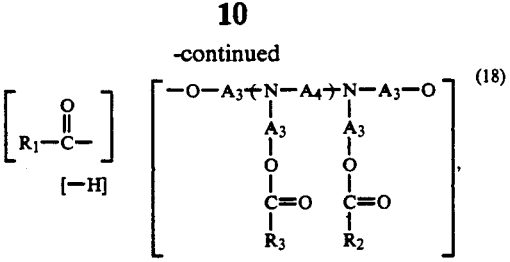 (18)

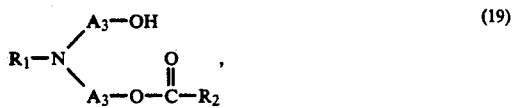 (19)

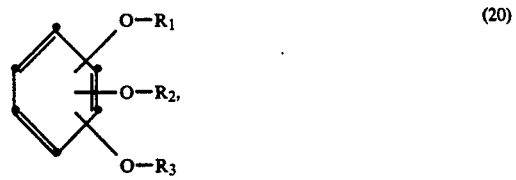 (20)

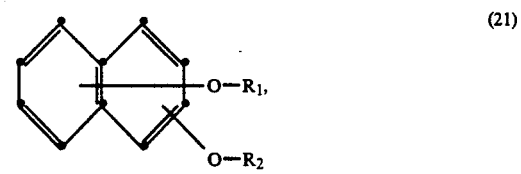 (21)

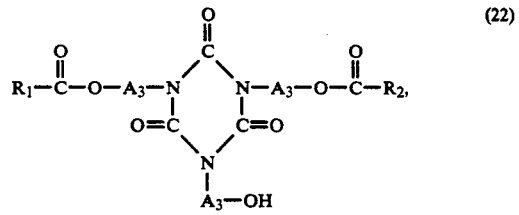 (22)

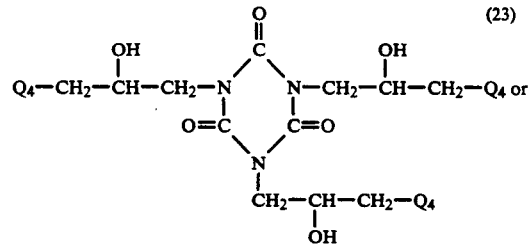 (23)

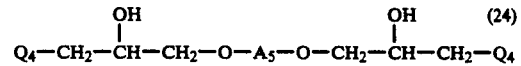 (24)

in which q is an integer from 1 to 5, preferably 1 to 3, in particular 1, t is 1 or 2, $A_3$ and $A_4$ each are propylene, isopropylene or ethylene, $A_5$ is branched or unbranched alkylene having 1 to 6 carbon atoms, $Q_4$ is

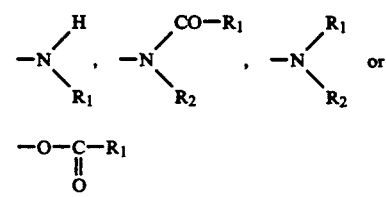

and $R_1$, $R_2$ and $R_3$ are different from or, preferably, identical to one another and each is alkyl or alkenyl having 6 to 22, preferably 8 to 22, in particular 16 to 20, carbon atoms, $R_1$ and $R_2$ being different from each other in the formula (15) and (18) if q and t are 1.

The method of preparing the intermediates of the formulae (15) to (24) is also part of the subject matter of the invention, and comprises reacting with one another (a) 1 mol of butane-1,2,4-triol, pentaerythritol, tris(hydroxymethyl)aminomethane or a compound of the formula

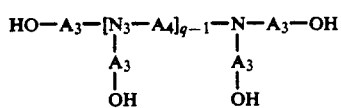 (25)

in which q, $A_3$ and $A_4$ are as defined above, in particular N,N,N',N'-tetrakis(2-hydroxypropyl)ethylenediamine or a compound of the formula

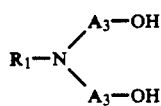 (26)

in which $R_1$ and $R_3$ are as defined above, in particular a $C_8$–$C_{22}$-fatty amine diethoxylate, or a compound of the formula

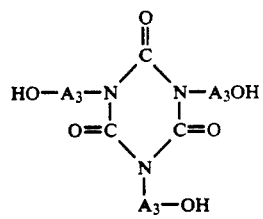 (27)

in which $A_3$ is as defined above, in particular tris(hydroxyethyl) isocyanurate, with (b) [h-1] mol(s) of an unsaturated or preferably saturated fatty acid of the formula

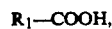 $R_1$—COOH, (28)

 $R_2$—COOH and/or (29)

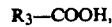 $R_3$—COOH, (30)

in which $R_1$, $R_2$ and $R_3$ are as defined above and [h] is the number of hydroxyl groups of component (a) or (a) 1 mol of pyrogallol, hydroxyhydroquinone, phloroglucine or a dihydroxynaphthalene with (b) [h-1] mol(s) of an alkenyl halide or preferably alkyl halide of the formula

 $R_1$ - $Z_1$, (31)

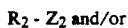 $R_2$ - $Z_2$ and/or (32)

 $R_3$ - $Z_3$, (33)

in which $R_1$, $R_2$, $R_3$ and h are as defined above and $Z_1$, $Z_2$ and $Z_3$ each are a halogen, preferably chlorine, in particular bromine, or (a) 1 mol of isocyanuric acid triglycide or 1 mol of the compound of the formula

in which $A_5$ is as defined above, in particular butanedioldiglycide, with (b) [h'] mol(s) of a fatty acid of the formula (26), a primary fatty amine of the formula

 $R_1$—$NH_2$ (35)

or a secondary fatty amine of the formula

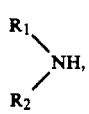 (36)

in which $R_1$ and $R_2$ are as defined above, or [h'] mol(s) of a primary fatty amine of the formula (33) and then [h'] mol(s) of a fatty acid of the formula (26) in which [h'] is the number of glycide groups of component (a).

The invention also relates to novel compounds and their salts, which can be obtained from the novel intermediates prepared from components (a) and (b) of the formulae (15) to (24) or from dialkyl ethers or dialkenyl ethers of hydroquinone, resorcinol or pyrocatechol each having 6 to 22, preferably 8 to 22, in particular 16 to 20, carbon atoms in the alkyl or alkenyl radical and from a polybasic inorganic or organic acid having 2 to 18 carbon atoms as component (c) and which can be used as sizing agent (A) in the invention and have one of the formulae

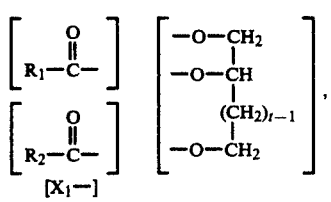 (37)

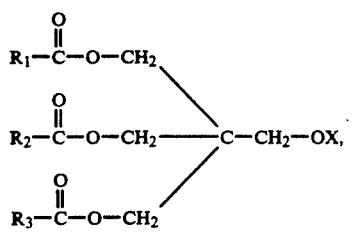 (38)

-continued
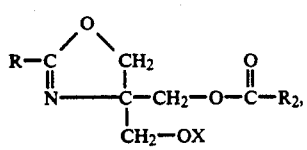 (39)
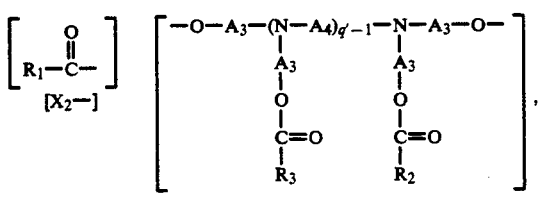 (40)
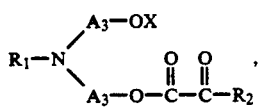 (41)
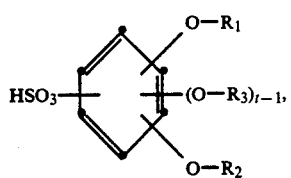 (42)
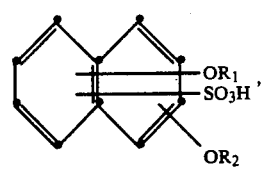 (43)
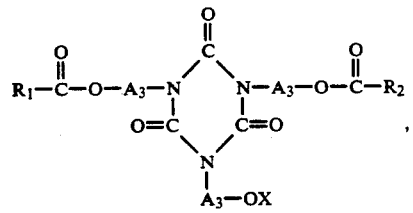 (44)
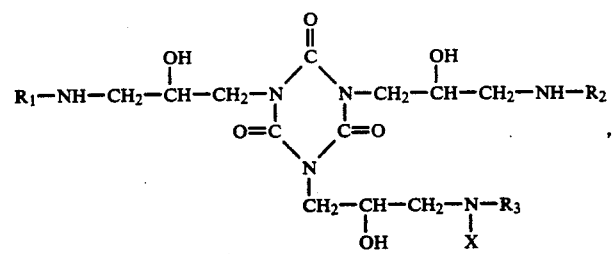 (45)
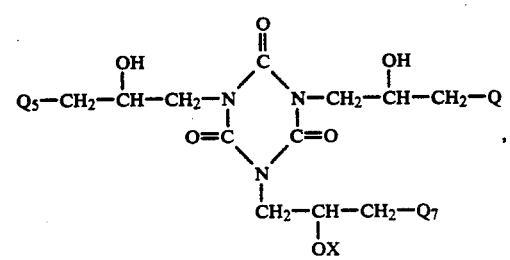 (46)
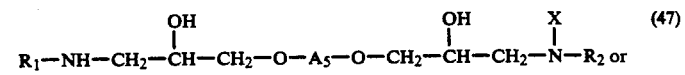 (47)

-continued

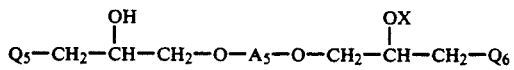
(48)

in which q is an integer from 1 to 5, t is 1 or 2, $Q_5$, $Q_6$ and $Q_7$ each are

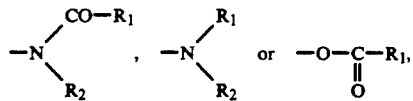

X is the radical of a polybasic inorganic or organic acid having 2 to 18, preferably 4 to 9, carbon atoms, $X_1$ is defined in the same way as X or, if t is 1, is
—CO—$C_6H_4$—COOH, —CO—$(CH_2)_2$—COOH, —CO—CH=CH—COOH, or $SO_3H$, $X_2$ is defined in the same way as X or, if q is 1, is —CO—CH=CH—COOH,

or —$SO_3H$, and $A_3$, $A_4$, $A_5$, $R_1$, $R_2$ and $R_3$ are each as defined above.

The method of preparing the novel compounds of one of the formulae (37) to (48) or their salts is part of the subject matter of the invention. This method comprises reacting 1 mol of an intermediate of the formulae (16), (17), (19), (22), (23) and (24) or 1 mol of an intermediate of the formula (15) in which t is 2 or 1 mol of an intermediate of the formula (18) in which q is 2, 3, 4 or 5, with 1 to 2, preferably 1 to 1.5, in particular 1, mol(s) of a polybasic acid, as component (c), of the formula

H—X, (49)

in which X is defined as above, or 1 mol of the intermediate of the formula (15) in which t is 1, with 1 to 2, preferably 1 to 1.5, in particular 1, mol(s) of a polybasic acid, as component (c), of the formula

H—$X_1$ (50)

in which $X_1$ is —CO—$C_6H_4$—COOH, —CO—$(CH_2)_2$—COOH, —CO—CH=CH—COOH or —$SO_3H$, or 1 mol of the intermediate of formula (18) in which q is 1 and $R_1$ and $R_2$ are different from or, preferably, identical to each other, with 1 to 2, preferably 1 to 1.5, in particular 1, mol(s) of a polybasic acid, as component (c), of the formula

H—$X_2$ (51)

in which $X_2$ is —CO—CH=CH—COOH,

or —$SO_3H$ or 1 mol of an intermediate of the formula (20) or (21) or of the compound of the formula

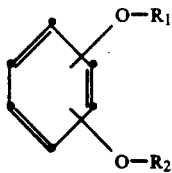
(52)

in which $R_1$ and $R_2$ are each as defined above, with 1 to 2, preferably 1 to 1.5, in particular 1, mol(s) of chlorosulfonic acid as component (c), and, if desired, converting the reaction products obtained into the corresponding salts.

In the course of the reaction of aliphatic or heterocyclic compounds of the formulae (15) to (19) or (22) to (24) as intermediates, with the acids of the formula (49), (50) or (51) as component (c), the free hydroxyl group of the compounds (15) to (19) or (22) or at least one of the free hydroxyl groups present in the compounds of the formula (23) or (24) reacts with the compound of the formula (49), (50) or (51) in such a way that acidic esters are formed. However, if aromatic compounds of the formula (20) or (21) are used as intermediates or compounds of the formula (52) are used as starting materials, the reaction with chlorosulfonic acid as component (c) takes place at the aromatic nucleus of said intermediates or starting materials.

The processes for preparing intermediates from the components (a) and (b) and acidic esters by further reaction with component (c) are preferably carried out in the presence of solvents which need to be inert not only to every starting component (a), (b) and (c) but also to the intermediate and end products, i.e. the reaction products of (a) and (b) and of (a), (b) and (c). Suitable solvents are in particular halogenated or unhalogenated hydrocarbons which have a boiling point of at most 140° C. For the reaction between components (a) and (b) hydrocarbons which boil between about 110° C. and about 140° C. are preferred, for example toluene, chlorobenzene, o-, m- or p-xylene, a technical xylene mixture or even mixtures of the hydrocarbons mentioned. If the further reaction of the intermediates from components (a) and (b) with component (c), not only the specified hydrocarbons but also preferably halogenated hydrocarbons which boil at a lower boiling point, for example at about 40° C. to about 80° C., for example dichloroethane or carbon tetrachloride, are suitable. Particularly suitable elevated temperatures in the reaction of components (a) and (b) are temperatures of 100° C. to 140° C. and in the further reaction with component (c) room temperature (15° to 25° C.) to elevated temperatures of about 40° to 80° C.

It is furthermore advantageous to carry out the reaction of components (a) and (b), especially, in the presence of a catalyst which will accelerate the esterification reaction if need be.

Examples of suitable catalysts are inorganic acids such as hydrochloric acid, sulfuric acid or phosphoric acid, and especially organic acids such as organic sulfonic acids and, in particular, p-toluenesulfonic acid. It is advantageous to use, for example, 1 to 4% of these catalysts per mol of component (a).

To prevent polymerisation in the course of the preparation of acidic esters having a reactive C=C double bond, the esterification with component (c) can advantageously be carried out in an inert nitrogen atmosphere. This is particularly relevant when particularly reactive components, for example maleic acid, are used. In this case or when an unsaturated (b) component, for example oleic acid, is used, it is advantageous to use a polymerisation inhibitor, especially at elevated temperatures. Examples of such inhibitors are methylene blue, benzothiazine and, in particular, hydroquinone. It is advantageous to use, for example, 0.1 to 0.3% of these inhibitors per mol of unsaturated components (b) or (c).

In another preferred embodiment the sizing agents (A) used in the invention preferably contain besides acidic phosphate or sulfate or carboxyl groups as anionic or acid group and preferably 2 to 5, in particular 2 hydrophobic substituents of the specified type divalent linking members with which at least two of the most adjacent hydrophobic substituents are bonded to each other, which have preferably 1 to 15, preferably 2 to 4, carbon atoms and at least 2 hetero atoms, preferably 2 to 6, in particular 2, nitrogen atoms. Depending on the number of hydrophobic substituents, such sizing agents contain 1 to 5, preferably 1 to 3, in particular 1, linking member of the specified type.

In their simplest embodiment preferred linking members have the formula

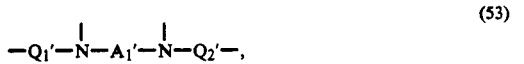

(53)

in which $Q'_1$ is ethylene, propylene or butylene and $Q'_1$ and $Q'_2$ each are a direct bond, —CO— or —CO—NH—.

Linking members of the formula (53) are parts of ing members which have at least one anionic or acidic group bonded to a nitrogen atom and the formula

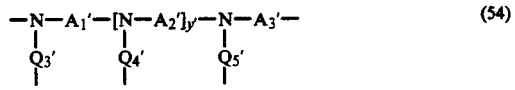

(54)

in which $A'_1$, $A'_2$ and $A'_3$ each are ethylene, propylene or butylene, at least one of the radicals $Q'_3$, $Q'_4$ and $Q'_5$ is —X' at least two of the radicals $Q'_3$, $Q'_4$ and $Q'_5$ are —CO—, —CO—NH— or a direct bond, X' is an anionic or acidic group or a radical carrying such a group, and y' is an integer from 1 to 5.

In the formula (54), y' is preferably 2, and especially 1. Moreover, $A'_1$, $A'_2$ and $A'_3$ are preferably defined in the same way and are in particular propylene and, especially, ethylene.

Bridging members to the fore of interest thus have the formula

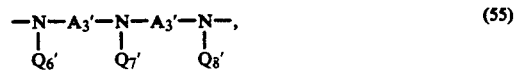

(55)

in which the $A'_3$ radicals are ethylene or propylene and two of the $Q'_6$, $Q'_7$ and $Q'_8$ radicals are —CO— or —CO—NH— and one of the radicals $Q'_6$, $Q'_7$ and $Q'_8$ is —X', —X' being as defined above.

Those sizing agents (A) are of particular importance which can be obtained by reacting (a') a polyalkylenepolyamine which is unsubstituted or monosubstituted by N—$C_6$–$C_{22}$-alkyl or -alkenyl and has 3 to 6 nitrogen atoms and 4 to 40 carbon atoms with (b') a fatty acid or a fatty alcohol, an alkyl or alkenyl halide or an alkyl or alkenyl isocyanate having at least 5, preferably 6 to 22, especially 16 to 20, carbon atoms in the alkyl or alkenyl radical and then with (c') the anhydride of a polybasic, preferably tribasic, in particular dibasic, inorganic or organic acid having 2 to 18, preferably 2 to 8, carbon atoms or an α- or β-halogenocarboxylic acid having 2 to 6 carbon atoms, the component (c') being added last.

Examples of specific representatives of from which the sizing agent can be obtained are N,N'-bis(3-aminopropyl)-1,4-diaminobutane, N-(3-aminopropyl)-1,4-diaminobutane, 1,2-bis( 3-aminopropylamino)ethane, pentaethylenehexamine, especially tetraethylenepentamine, triethylenetetramine and in particular dipropylenetriamine and diethylenetriamine, the last being to the fore of interest.

A component (b') from which the sizing agent (A) can be obtained is in particular a saturated or unsaturated fatty acid, an alkenyl, preferably alkyl isocyanate having 6 to 22, preferably 8 to 22, in particular 16 to 20 carbon atoms in the alkyl or alkenyl radical. An unsaturated or saturated $C_6$–$C_{22}$-, preferably $C_8$–$C_{22}$-, in particular $C_{16}$–$C_{20}$-, fatty acid for use as component (b') is e.g. caproic, preferably caprylic, capric, lauric, myristic or arachidic acid, in particular palmitic, stearic or behenic acid or myristoleic, palmitoleic, elaeostearic, clupanodonic acid, in particular oleic, elaidic, erucic, linoleic or linolenic acid. Of these, palmitic, stearic, oleic and behenic acid are all of particular importance, palmitic and especially stearic acid being to the fore of interest. Technical, readily accessible, mixtures of the acids just mentioned are also suitable. Because it is readily accessible, octadecyl isocyanate is mentioned as a $C_{16}$–$C_{20}$- alkyl isocyanate.

Anhydrides of organic polybasic acids are preferred to those of inorganic polybasic acids for use as component (c'). Examples of specific representatives of the anhydrides of inorganic polybasic acids are sulfur trioxide, especially phosphorus pentoxide and in particular chlorosulfonic acid. An organic polybasic acid anhydride is, for example, the anhydride of benzophenone tetracarboxylic acid, 1,8-naphthalic acid, trimellitic acid, pyromellitic acid, bicyclo(2,2,1)hept-5-ene-2,3-dicarboxylic acid (also called norbornene dicarboxylic acid or nadic acid), hexahydrophthalic acid, tetrahydrophthalic acid, phthalic acid, succinic acid, glutaric acid, dimethylmaleic acid, citraconic acid, itaconic acid, and in particular maleic acid. The halogenocarboxylic acid is, for example, 2-chlorobutyric acid, 2- and 3-chloropropionic acid, bromoacetic acid or chloroacetic acid and their alkali metal salts. The sultone used is especially propanesultone. To the fore of interest are glutaric anhydride, succinic anhydride, sodium chloroacetate, citraconic anhydride, itaconic anhydride, phthalic anhydride, pyromellitic anhydride and in particular trimellitic anhydride and maleic anhydride, from which particularly effective sizing agents can be obtained.

The reaction products of components (a') and (b') are intermediates from which the sizing agents (A) can be obtained by reacting these intermediates with component (c').

As mentioned above, some of the sizing agents (A) used in the invention are compounds known per se. This is also true of intermediates from components (a') and (b') from which the sizing agents (A) can be obtained.

For instance, French Patent 1,388,523, inter alia, describes intermediates prepared from fatty acids, for example oleic acid or stearic acid, and polyalkylenepolyamines, for example triethylenetetramine, which are reacted with polybasic acids. As polybasic acids, however, this patent specification explicitly only mentions hexahydrophthalic, tetrahydrophthalic, phthalic, terephthalic, trimellitic, succinic, adipic and maleic acid and the corresponding anhydrides.

U.S. Pat. No. 4,332,737 also describes intermediates prepared from fatty acids and polyalkylenepolyamines, which are reacted with polybasic acids, but as polybasic acids it explicitly mentions naphthalene dicarboxylic acids, phthalic, terephthalic, malonic, succinic, glutaric, maleic and citraconic acid and the corresponding anhydrides.

Japanese Patent Application 74/137,917, finally, discloses intermediates prepared from fatty acids and polyalkylenepolyamines, which are only reacted with sodium chloroacetate as acid.

Intermediates prepared from polyalkylenepolyamines and fatty alcohols or alkyl or alkenyl halides are known and are commercially available. Intermediates prepared from polyalkylenepolyamines or N-alkyl or -alkenylpolyalkylenepolyamines and alkyl or alkenyl isocyanates, however, are novel. This is also true of the reaction products of such intermediates with any desired polybasic acid. Reaction products prepared from polyalkylenepolyamines and fatty acids and reacted with polybasic acids are also novel provided the polybasic acid anhydride used was that of pyromellitic acid, norbornene dicarboxylic acid, dimethylmaleic acid or citraconic acid. Reaction products reacted with 2-chlorobutyric acid, 2- or 3-chloropropionic acid, bromoacetic acid or propanesultone are also novel.

The invention accordingly also relates to intermediates which can be obtained by reacting ($a'_1$) 1 mol of a polyalkylenepolyamine which is unsubstituted or monosubstituted by $C_6$-$C_{22}$-alkyl or -alkenyl and has 3 to 6 nitrogen atoms and 4 to 40 carbon atoms with ($b'_1$) 1 to [$h''$-1] mol(s) of an alkenyl isocyanate or preferably alkyl isocyanate having at least 5, preferably 6 to 22, especially 8 to 22, in particular 16 to 20, carbon atoms in the alkyl or alkenyl radical, [$h''$] denoting the number of nitrogen atoms of component ($a'_1$), compounds which can be obtained by reacting intermediates prepared from components ($a'_1$) and ($b'_1$) with ($c'_1$) 1 to $h''_1$] mol(s) of the anhydride of a polybasic, preferably dibasic, inorganic or, in particular organic acid having 2 to 18 carbon atoms, a 2- or 3-halogenocarboxylic acid having 2 to 6 carbon atoms or a sultone, [$h''_1$] denoting the number of free nitrogen atoms present in the intermediate from ($a'_1$) and ($b'_1$) which are not reacted with component ($b'_1$), compounds which can be obtained by reacting ($a'_1$) 1 mol of a polyalkylenepolyamine having 3 to 6 nitrogen atoms and 4 to 20 carbon atoms with ($b'_2$) 1 to [$h''$-1] mol(s) of an unsaturated or preferably saturated fatty acid having at least 5, preferably 6 to 22, especially 8 to 22, in particular 17 to 20, carbon atoms, [$h''$] being as defined above, and then with ($c'_1$) 1 to [$h''_2$] mol(s) of pyromellitic, norbornene dicarboxylic, dimethylmaleic or citraconic anhydride, 2-chlorobutyric acid, 2- or 3-chloropropionic acid, bromoacetic acid or propanesultone, [$h''_2$] denoting the number of free nitrogen atoms present in the intermediate product from ($a'_1$) and ($b'_2$) which are not reacted with component ($b'_2$).

The reactions of components (a') and (b') are generally carried out at about 120° to about 250° C., preferably up to 200° C., in the melt. If high temperatures of about 200° to 250° C. are used, the resulting products can be purified with active charcoal if necessary. However, especially if alkenyl or alkyl isocyanates are used as component (b') or in the reaction with component (c') it is also possible to carry out the reactions in the presence of at least one solvent which needs to be inert to the starting, intermediate and end products. If such solvents are used, the reactions can also be carried out at lower temperatures, for example 30° to 120° C. Examples of possible solvents are acetone, dioxane and halogenated or unhalogenated hydrocarbons, for example dichloroethane, carbon tetrachloride, benzene, toluene, chlorobenzene, o-, m- and p-xylene, a technical xylene mixture or mixtures of the hydrocarbons mentioned. If halogenated carboxylic acids, for example chloroacetic acid, are reacted as component (c'), it is advisable to prevent the formation of by-products by using an approximately equimolar amount (based on the halogenated acid) of a weak nitrogen-containing base, for example pyridine, isoquinoline, quinoline or preferably triethylamine, as an acid acceptor. If unsaturated (c') or especially (b') components are used, it is furthermore advantageous to carry out the reaction in an inert nitrogen atmosphere and/or especially at elevated temperatures in the presence of a polymerisation inhibitor, for example methylene blue, benzothiazine or preferably hydroquinone.

Preferred sizing agents (A) of the type specified from the components (a'), (b') and (c') in particular have molecular weights of about 400 to about 3,000, preferably about 500 to about 3,000, in particular about 600 to about 1,500, and, owing to the fact that they contain at least one acidic group, for example an —$SO_3H$ or —COOH group, an acid value (mg of KOH/g of substance) of about 15 to 150, preferably about 50 to about 120.

In a further preferred embodiment the sizing agents (A) used in the invention contain besides 1 or 2 potential anionic, acidic methylene or methine groups and 2 or 3 hydrophobic substituents of the specified type divalent linking members with which at least two of the most adjacent hydrophobic substituents are bonded to each other which have 1 to 15, preferably 3 to 8, carbon atoms and each have at least 2 hetero atoms, preferably 2 to 4 nitrogen and/or oxygen atoms or in particular 4 nitrogen atoms or 2 oxygen atoms. The linking members which each have 3 to 5 carbon and 2 oxygen atoms are particularly preferred. Depending on the number of hydrophobic substituents, the sizing agents preferably contain 1 or 2 linking members of the specified type.

Preferred linking members generally have one of the formulae

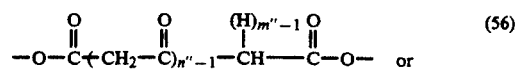 (56)

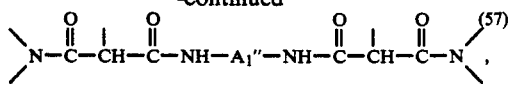

in which n″ and m″ each are 1 or 2 and A″₁ is branched or especially straight-chain alkylene having 4 to 12, in particular 6 to 10, carbon atoms, cycloalkylene having 6 to 14 carbon atoms or arylene having 6 to 14, in particular 6 to 8, carbon atoms. If m″ in the formula (56) is 1, the linking member has a methine group at the corresponding site. However, if m″ is 2, the linking member has a methylene group at the corresponding site.

In linking members of the formula (56) or (57) the methylene or methine groups are part of a divalent or trivalent —CO—CH₂CO— or

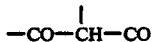

radical where the acidic properties of the methylene or methine groups is due to each methylene group being linked between two CO groups or the methine group being linked between 3 CO groups or 2 CO groups and one CN group.

If n in the formula (56) is 2, m is generally 2. m is generally only defined as 1 if n is also 1. However, the linking member particularly preferably has the formula (56) in which n is 1 and m is 2.

Those sizing agents (A) are of particular importance which can be obtained by reacting (a″₁) malonic acid, a malonyl dihalide, acetone dicarboxylic acid or a $C_1$-$C_4$-alkyl malonate, acetone or methane tricarboxylate with (b″₁) a fatty alcohol or (a″₂) cyanoacetic acid or its $C_1$-$C_4$-alkyl ester with (b″₂) a fatty amine and then with (c″) a $C_4$-$C_{12}$-alkylene, $C_6$-$C_{14}$-cycloalkylene or $C_6$-$C_{14}$-arylene diisocyanate.

A suitable component (a″₁), from which the sizing agent (A) can be obtained, is in particular a dihalide, for example the dibromide and in particular the dichloride, of malonic acid and its methyl or in particular ethyl esters. Malonyl dichloride is particularly preferred because of its high reactivity. The dimethyl and especially the diethyl ester of acetone dicarboxylic acid and the trimethyl and especially triethyl ester of methanetricarboxylic acid are also suitable because they are readily accessible.

Component (a″₂) is in particular methyl cyanoacetate and especially ethyl cyanoacetate.

Malonyl dichloride and ethyl cyanoacetate are to the fore of interest for use as components (a″₁) and (a″₂).

Suitable for use as component (b″₁), from which the sizing agent (A) can be obtained, are in particular saturated or unsaturated aliphatic alcohols having 6 to 22, preferably 8 to 22, in particular 16 to 20 carbon atoms and for use as component (b″₂) in particular monoalkylamines, dialkylamines, monoalkenylamines or dialkenylamines which each have 6 to 22, preferably 8 to 22, in particular 16 to 20, carbon atoms in the alkyl or alkenyl radical. Saturated fatty alcohols and alkylamines or dialkylamines are preferred to unsaturated fatty alcohols and alkenylamines or dialkenylamines. Primary amines are also preferred to secondary amines. Specific $C_{16}$-$C_{20}$ fatty alcohols and $C_{16}$-$C_{20}$-alkyl radical monoalkylamine or dialkylamine representatives mentioned because they are readily accessible are hexadecanol, octadecanol, oleyl alcohol, octadecylamine and dioctadecylamine. Technical mixtures of fatty alcohols or fatty amines of the specified type are also suitable.

An aliphatic diisocyanate as component (c″) has branched or preferably straight-chain alkylene radicals having about 4 to 12, in particular 6 to 10, carbon atoms. Specific representatives of such diisocyanates are butylene diisocyanate, dodecylene diisocyanate, especially decylene 1,10-diisocyanate and in particular hexylene 1,6-diisocyanate. A cycloaliphatic diisocyanate generally has 6 to 14 carbon atoms in the cycloalkylene radical. Examples are cyclohexyl and dicyclohexyl diisocyanate. The aromatic diisocyanates generally have 6 to 14, preferably 6 to 8, carbon atoms in the arylene radical. Examples of specific representatives are naphthylene 1,5-diisocyanate, diphenylmethane 4,4′-diisocyanate, phenylene 1,4-diisocyanate and toluylene 2,4- and 2,6-diisocyanate. Hexane 1,6-diisocyanate and toluylene 2,4- or 2,6-diisocyanate and especially technical toluylene 2,4- and 2,6-diisocyanate mixtures are mentioned because they are readily accessible.

About 1 mol of fatty alcohol as component (b″₁) is generally used per functional group of the component (a″₁) used. For instance, about 2 mols of fatty alcohol are generally used per mol of component (a″₁) if component (a″₁) is malonic acid or acetone dicarboxylic acid or halides or esters thereof, and about 3 mols of fatty alcohol are used per mol of component (a″₁) if the component (a″₁) is methyl or ethyl methanetricarboxylate.

If components (a″₂) and (b″₂) are used, they are generally reacted with each other, in about equimolar ratios. The resulting cyanoacetic acid fatty amide is an intermediate which is reacted with component (c″), about 0.5 mol of alkylene, cycloalkylene or arylene diisocyanate of the specified type being used as component (c″) per mol of the intermediate from about equimolar amounts of the components (a″₂) and (b″₂).

Sizing agents (A) of the specified type from the components (a″₁) and (b″₁) or from the components (a″₂), (b″₂) and (c″) which are preferably used have molecular weights of about 400 to about 3,000, preferably of about 600 to about 1,500.

The reactions of the (a″₁), (a″₂), (b″₁), (b″₂) and (c″) components specified above are generally carried out by methods known per se. For example, the reactions of components (a″₁) with (b″₁) or (a″₂) with (b″₂) are carried out at about 30° to about 250° C., preferably at about 40° to 140° C., in the melt, as the case may be. If high temperatures of about 200° to 250° C. are used, the resulting products can be purified with active charcoal if necessary. However, on use of acid halides as component (a″₁) in particular and on reacting intermediates prepared from components (a″₂) and (b″₂) with component (c″) in general it is advantageous to carry out the reactions in the presence of at least one solvent which needs to be inert to every starting, intermediate and end product. If such solvents are used, the reactions can also be carried out at lower temperatures, for example at 30° to 120° C., preferably 30° to 50° C. Examples of possible solvents are acetone, dioxane and halogenated or unhalogenated hydrocarbons such as dichloroethane, carbon tetrachloride, benzene, toluene, chlorobenzene, o-, m- and p-xylene, a technical xylene mixture or even mixtures of the hydrocarbons mentioned, which are particularly suitable for use as reaction medium when acid halides as component (a"₁) are reacted with fatty alcohols as component (b"₁). If intermediates prepared from (a"₂) and (b"₂) are reacted with component (c"), in particular dimethylformamide or dimethylsulfoxide are particularly suitable for use as further solvent. If free acids are reacted as components (a"₁) or (a"₂) with fatty alcohols or fatty amines as components (b"₁) or (b"₂), the use of a catalyst, for example hydrochloric acid, sulfuric acid, phosphoric acid or organic sulfonic acids, preferably p-toluenesulfonic acid, can be advantageous to accelerate the esterification or transesterification reactions if need be. If unsaturated (b"₁) and (b"₂) components are used it is furthermore advantageous to carry out the reaction in an inert nitrogen atmosphere and/or, especially at high temperatures, for example above 90° C., in the presence of a polymerisation inhibitor, for example methylene blue, benzothiazine or preferably hydroquinone.

As mentioned above, some of the sizing agents (A) are compounds known per se. For example, the article by Staudinger et al. in the journal "Makromolekulare Chemie," Volume 3, pages 251 to 280 (1949), describes fatty alkyl diesters of malonic acid, i.e. compounds which have a linking member of the formula (56) in which n is 1 and m is 2. The article by Staudinger et al. says nothing, however, about the possible use of the disclosed compounds. Furthermore, British Patent 737,528 for example, discloses fatty alkyl diesters of acetone dicarboxylic acid, i.e. compounds which have a linking member of the formula (56) in which m and n are 2. However, this patent specification has nothing to say about using the disclosed compounds as sizing agents for paper.

On the other hand, compounds which have a linking member of the formula (56) in which n and m are 1, or a linking member of the formula (57) are novel compounds. The intermediates prepared from components (a"₂) and (b"₂) are also novel.

The invention thus also relates to compounds which can be used as intermediates and have the formula

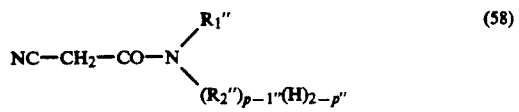

in which p" is 2 or preferably 1, R₁" and R₂" are different from or preferably identical to each other and each is alkenyl or preferably alkyl having 6 to 22, but preferably 8 to 22, in particular 16 to 20, carbon atoms, and to their salts.

The invention also relates to a process for preparing the compounds of the formula (58), which comprises reacting 1 mol of cyanoacetic acid or its C₁–C₄-alkyl ester with about 1 mol of a secondary or primary amine of the formula

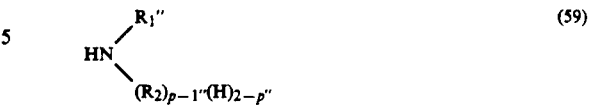

Novel compounds which are part of the subject matter of the invention and can be used as sizing agents (A) have the formula

or

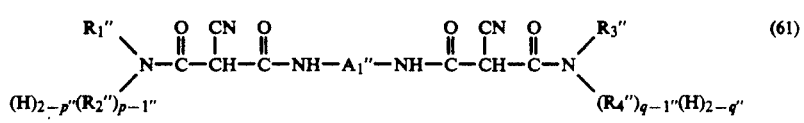

in which p" and q" are different from or preferably identical to each other and each is 2 or preferably 1, R₁", R₂", R₃" and R₄" are different from or preferably identical to one another and each is alkenyl or preferably alkyl having 6 to 22, preferably 8 to 22, in particular 16 to 20, carbon atoms and A₁" is cycloalkylene having 6 to 14 carbon atoms, especially alkylene having 4 to 12, preferably 6 to 10, carbon atoms or arylene having 6 to 14, preferably 6 to 8, carbon atoms.

The process for preparing compounds of the formula (60) or (61) comprises reacting 1 mol of C₁–C₄-alkyl methanetricarboxylate, in particular ethyl methanetricarboxylate, with about 3 mols of a fatty alcohol of one of the formulae $$R_1''\text{—OH}, \quad (62)$$

$$R_2''\text{—OH} \quad (63)$$

or $$R_3''\text{—OH}, $$

in which R₁", R₂" and R₃" are as defined above, or reacting 1 mol of diisocyanate of the formula $$O=C=N-A_1''-N=C=O,$$

in which A₁ is as defined above, with about 2 mols of the intermediate of the formula (58) or of the formula

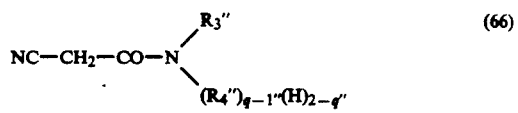

in which R₃", R₄" and q" are as defined above. In a further also preferred embodiment, the sizing agents (A) as inventively used contain besides 1 to 6, preferably 1 to 4, in particular 1 or 2, —COO⁻ or —COOH groups as anionic or acidic groups and 2 to 10, preferably 2 to 6, hydrophobic substituents of the specified type divalent linking members with which at least two of the most adjacent hydrophobic substituents are bonded to each other which preferably have 4 to 15 carbon atoms and at least 2 hetero atoms each, preferably one nitrogen and one oxygen atom or in particular 2 nitrogen atoms or 2 oxygen atoms. Linking members which each have 4 to 10 carbon and two oxygen atoms are particularly preferred. Depending on the number of hydrophobic substituents, the sizing agents contain 1 to 5, preferably 1 to 3, linking members of the specified type.

Preferred linking members generally have one of the formulae

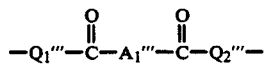 (67)

or

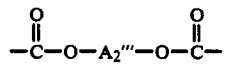 (68)

in which $A_1'''$ and $A_2'''$ each are a divalent aliphatic or aromatic radical, $Q_1'''$ and $Q_2'''$ are different from or preferably identical to each other and are —O—, —NH— or —N<.

In the formulae (67) and (68), the radicals $A_1'''$ and $A_2'''$ form part of an aliphatic or aromatic bridging member which has 1 to 6, preferably 1 to 4, in particular 1 or 2, anionic or acidic groups and can have 1 nitrogen atom.

Specific examples of preferred bridging members are those of the formulae

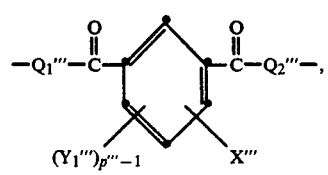 (69)

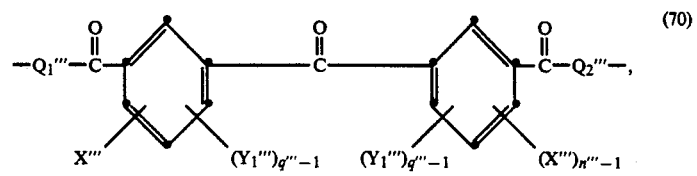 (70)

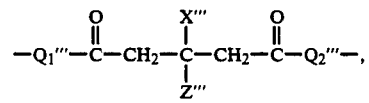 (71)

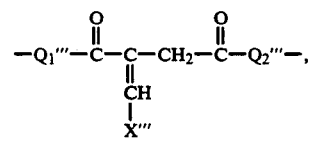 (72)

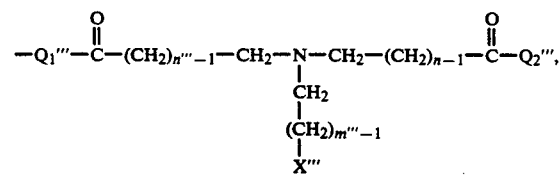 (73)

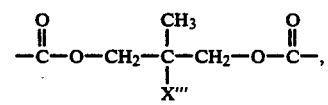 (74)

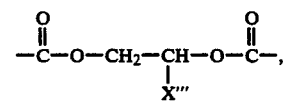 (75)

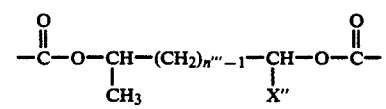 (76)

or

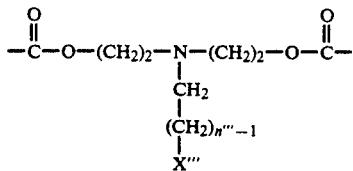

(77)

in which $Q_1$ and $Q_2$ each are —O—, —NH— or —N<, X''' is —COOH, or —COO$^\ominus$, Y''' is —COOH, —COO$^\ominus$ or

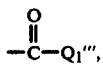

Z''' is hydrogen, methyl or preferably hydroxyl, n''' and m''' each are 1 or 2, p''' is an integer from 1 to 4 and q''' and q'''' each are 1, 2 or 3.

In particular those sizing agents (A) are of special importance which can be obtained by reacting at least (a''') an aliphatic or aromatic carboxylic acid having at least 3 carboxyl groups, a polyalkylenepolyaminopolyacetic acid having 4 to 6 carboxyl groups or an aliphatic monocarboxylic acid or aminocarboxylic acid having 2 hydroxyl groups with (b''') a fatty alcohol and/or a fatty amine or a fatty acid, fatty alcohols and/or fatty amines being used as component (b''') when carboxylic acids having at least 3 or 4 to 6 carboxyl groups are used as component (a''') and fatty acids being used as component (b''') when monocarboxylic acids are used as component (a''').

The sizing agents which can be obtained in this way are, as a rule, aliphatic or aromatic fatty acid esters or fatty acid amides. Preferred esters or amides of this type have bridging members of one of the formulae (69) to (73) in which $Q_1'''$ and $Q_2'''$ are identical. Other sizes, however, are in the form of amide-esters which can be obtained not only from fatty alcohols but also from fatty amines and from aliphatic or aromatic acids having at least 3 carboxyl groups or 4 to 6 carboxyl groups. Preferred amide-esters of this type have bridging members of one of the formulae (69) to (73) in which $Q_1'''$ and $Q_2'''$ differ from each other. If monocarboxylic acids having 2 hydroxyl groups are used as component (a'''), only fatty acids are suitable for use as component (b'''), to give fatty acid esters which, in their preferred embodiment, have bridging members of one of the formulae (74) to (77).

Sizing agents (A) of the specified type from the components (a''') and (b''') which are preferably used have molecular weights of about 400 to about 3,000, preferably of about 600 to about 1,500. Sizes having a bridging member of one of the formulae (69) or (71) are particularly preferred.

In particular those sizing agents are to the fore of interest which can be obtained by reacting at least (a''') an aromatic acid which has 9 to 20 carbon atoms and 3 to 6 carboxyl groups, an aliphatic acid which has 3 carboxyl groups and can have a nitrogen atom, a polyalkylenepolyaminopolyacetic acid which has 4 to 6 carboxyl groups and 2 to 4 nitrogen atoms, an aliphatic dihydroxymonocarboxylic acid or bis(hydroxyalkyl)aminomonocarboxylic acid which has 3 to 6 carbon atoms, their halides or anhydrides, with (b''') a fatty alcohol and/or a primary or secondary fatty amine or, if a monocarboxylic acid of the specified type is used as component (a'''), from a fatty acid, the fatty radicals of the fatty alcohols, fatty amines and fatty acids being unsaturated or preferably saturated and having 6 to 22, preferably 8 to 22, in particular 16 to 20, carbon atoms.

For the sizing agents, as mentioned earlier, to have at least one —COO$^\ominus$ or —COOH group as anionic or acidic substituents and the linking member with which the hydrophobic substituents are directly bonded to each other to contain at least 2 hetero atoms, the sizing agents, in their preferred embodiment, can be obtained from 1 mol of component (a''') and 2 to (h'''-1) mol(s) of component (b'''),h''' denoting the number of carboxyl groups of component (a'''), if carboxylic acids having at least 3 or 4 to 6 carboxyl groups are used as components (a''') and fatty alcohols and/or fatty amines as component (b'''). If 1 mol of monocarboxylic acid having 2 hydroxyl groups is used as component (a'''), 2 mols of fatty acid are generally used, however.

Owing to the presence of at least one —COO$^\ominus$ or —COOH group in the sizing agents, they have an acid value (mg of KOH/g of substance) of about 15 to about 150, preferably of about 40 to about 100.

Carboxylic acids having at least 3 carboxyl groups for use as component (a'''), from which the sizing agents (A) can be obtained, are in particular aromatic mononuclear polycarboxylic acids, for example hemimellitic, trimellitic, trimesic, prehnitic, mellophanic, pyromellitic or mellitic acid, benzenepentacarboxylic acid, aromatic binuclear polycarboxylic acids, for example benzophenonetricarboxylic to benzophenonehexacarboxylic acid or anhydrides of said aromatic carboxylic acids, aliphatic tricarboxylic acids, for example tricarballylic, aconitic or citric acid, aliphatic tricarboxylic acids which have a nitrogen atom, for example bis(2-carboxyethyl)carboxymethylamine, nitrilotripropionic acid and nitrilotriacetic acid, and polyalkyleneaminopolyacetic acids, for example triethylenetetraaminehexaacetic acid, diethylenetriaminepentaacetic acid, dipropylenetriaminepentaacetic acid, ethylenediaminetetraacetic acid, N,N'-bis(2-carboxyethyl)-N,N'-bis(carboxymethyl)ethylenediamine, tris[2-bis(carboxymethylamino)ethyl]amine, bis[2-bis(carboxymethylamino)ethyl]methylamine or N,N'-bis[2-bis(-carboxymethylamino)ethyl]-N,N'-dimethylethylenediamine. Of these, because they are easily accessible, trimellitic anhydride, pyromellitic dianhydride, hemimellitic acid, benzophenonetetracarboxylic dianhydride, tricarballylic acid, trans-aconitic acid, citric acid and nitrilotriacetic acid are particularly preferred. Aliphatic monocarboxylic acids suitable for use as component (a''') are, for example, glyceric acid, 1,2-dihydroxybutyric acid, 1,3- and 2,3-dihydroxyvaleric acid, 2,2-bis(hydroxymethyl)propionic acid, N,N-bis(hydroxyethyl)-β-alanin and N,N-bis-(hydroxyethyl)glycine, of which 2,2-bis(hydroxymethyl)propionic acid and N,N-bis(hydroxyethyl)glycine are preferred. Trimellitic anhydride, pyromellitic dianhydride and citric acid are to the fore in interest.

If polyalkylenepolyaminopolyacetic acids are used as component (a'''), oligomeric sizing agents can be obtained therefrom. However, if the other acids are used as component (a'''), monomeric sizing agents can be obtained and are preferred to the oligomeric sizing agents.

Sizing agents (A) having a bridging member of the formula (69) can be obtained from, for example, said aromatic mononuclear polycarboxylic acids, having a bridging member of formula (70) from benzophenonetricarboxylic to benzophenonehexacarboxylic acid, having a bridging member of the formula (71) from tricarballylic or citric acid, having a bridging member of the formula (72) from aconitic acid, having a bridging member of the formula (73) from aliphatic tricarboxylic acids which have a nitrogen atom, having a bridging member of the formula (74) from 2,2-bis(hydroxymethyl)propionic acid, having a bridging member of the formula (75) from glyceric acid, having a bridging member of the formula (76) from 1,3-dihydroxyvaleric acid or 1,2-dihydroxybutyric acid, and having a bridging member of the formula (77) from N,N-bis(hydroxyethyl)-β-alanin or N,N-bis(hydroxyethyl)glycine as component (a''').

Component (b'''), from which the sizing agent (A) can be obtained, is in particular a saturated or unsaturated aliphatic fatty acid or alcohol having 6 to 22, preferably 8 to 22, in particular 16 to 20, carbon atoms or a monoalkylamine, dialkylamine, monoalkenylamine or dialkenylamine each having 6 to 22, preferably 8 to 22, in particular 16 to 20, carbon atoms in the alkyl or alkenyl radical. A component (b''') unsaturated or saturated $C_6$-$C_{22}$-, preferably $C_8$-$C_{22}$-, in particular $C_{16}$-$C_{20}$-, fatty acid is, for example caproic, preferably caprylic, capric, lauric, myristic or arachidic acid, in particular palmitic, stearic and behenic acid or myristoleic, palmitoleic, elaeostearic, clupanodonic acid, in particular oleic, elaidic, erucic, linoleic and linolenic acid. Of these palmitic, stearic, oleic and behenic acid are of particular importance, palmitic and especially stearic acid being to the fore of interest. Technical, readily accessible mixtures of the acids just mentioned are also suitable. The unsaturated or saturated fatty alcohols and the unsaturated or preferably saturated monoalkylamines or dialkylamines or monoalkenylamines or dialkenylamines structurally derive from the fatty acids just mentioned. Because they are readily accessible, hexadecanol, octadecanol, oleyl alcohol, octadecylamine and dioctadecylamine are mentioned as specific representatives of $C_{16}$-$C_{20}$ fatty alcohols and of monoalkylamines or dialkylamines having $C_{16}$-$C_{20}$ alkyl radicals. Technical mixtures of fatty alcohols or fatty amines of the specified type are also suitable.

The following compounds which can be used as size as component (A) of the process of the invention and their preparation from components (a''') and (b''') are known per se:

diesters and diamides of aromatic carboxylic acids having at least 3 carboxyl groups and bridging members of the formula (69) in which $Q_1'''$ and $Q_2'''$ are identical, and described in for example, German "Offenlegungsschrift" 2,417,556, British Patent 1,025,433 and U.S. Pat. No. 3,981,838;

diamides of aromatic carboxylic acids having at least 3 carboxyl groups and bridging members of the formula (70) in which $Q_1'''$ and $Q_2'''$ are identical and are —NH— or —N< and described in, for example, U.S. Pat. No. 3,275,651;

diesters and diamides of aliphatic carboxylic acids having 3 carboxyl groups and bridging members of the formula (71) in which $Q_1'''$ and $Q_2'''$ are identical and are —O—, —NH— or —N< and $Z'''$ is —OH and described in, for example, U.S. Pat. Nos. 3,929,712 and 4,021,377; and diesters of 2,2-bis(hydroxymethyl)propionic acid which have bridging members of the formula (74) and are described in, for example, British Patent 1,257,928 and U.S. Pat. No. 3,441,953.

On the other hand, novel compounds which can be used as sizing agents in the invention have the formula

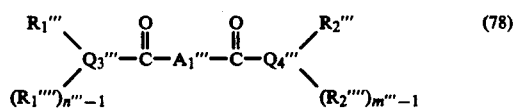

or

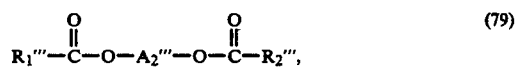

in which m''' and n''' each are 1 or 2, $Q_3'''$ and $Q_4'''$ each are —O— or —NH— or, if n''' and/or m''' are 2, $Q_3'''$ and/or $Q_4'''$ are n—N< and $R_1'''$, $R_1''''$, $R_2'''$ and $R_2''''$ each are alkyl or alkenyl having at least 5 carbon atoms, at least one of the radicals $R'''_1$, $R''''_1$, $R'''_2$ and $R''''_2$ having at lest 8, preferably 8 to 22, in particular 16 to 20, carbon atoms, $A'''_1$ is a divalent radical of one of the formulae

or

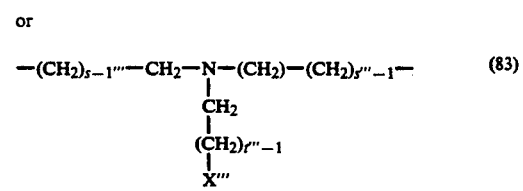

or, if $Q_3'''$ and $Q_4'''$ in the formula (78) are different from each other, one of the formula

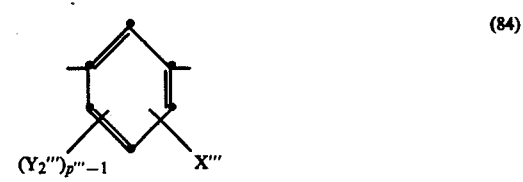

or

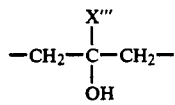 (85)

or, if $Q_3'''$ and $Q_4'''$ in the formula (78) are identical and are —O— or $Q_3'''$ and $Q_4'''$ are different from each other, the formula

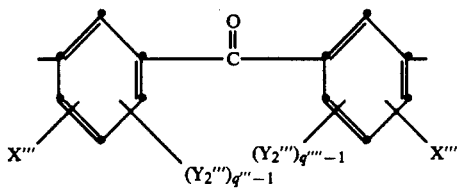 (86)

and $A_2'''$ is a divalent radical of one of the formulae

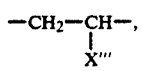 (87)

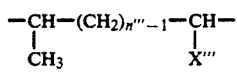 (88)

or

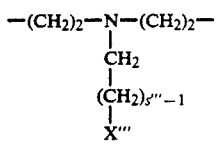 (89)

in which $X'''$ is —COOH or —COO$^\ominus$, $Y'''_2$ is

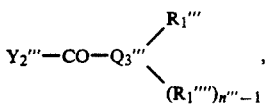, $p'''$ is an integer from 1 to 4, $q'''$ and $q''''$ each are 1, 2 or 3 and $m''''$, $n'''$, $s'''$ and $t'''$ each are 1 or 2 and $Q'''_3$, $R'''_1$ and $R''''_1$ are as defined above.

Preferred novel compounds which can be used as sizes have one of the formulae

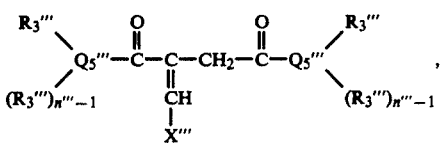 (90)

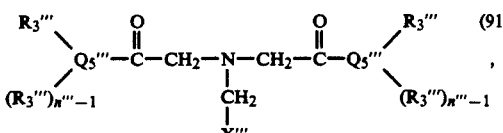 (91)

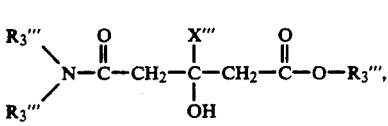 (92)

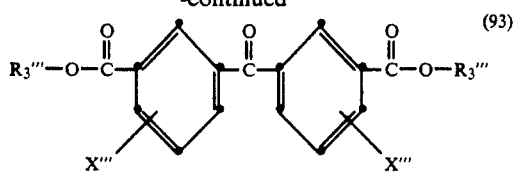 (93)

or

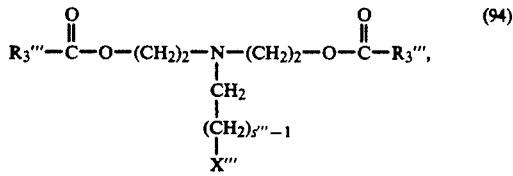 (94)

in which $n'''$ and $s'''$ are 1 or 2, $Q_5'''$ is —O— or, if $n'''$ is 2, —N<, $X'''$ is —COOH or —COO$^\ominus$ and $R_3'''$ is alkenyl or preferably alkyl having 16 to 20 carbon atoms.

The novel compounds are generally prepared by reacting 1 mol of a polycarboxylic acid of the formula $$HO-\overset{O}{\underset{\|}{C}}-A_1'''-\overset{O}{\underset{\|}{C}}-OH \quad (95)$$

with 2 to (h'''-1) mol(s) of a fatty alcohol of the formula $R_1'''$—OH (96)

or $R_2'''$—OH (97)

and/or with 2 to (h'''-1) mol(s) of a primary or secondary fatty amine of the formula $$\begin{matrix} R_1''' \\ \diagdown \\ (R_1'''')_{n'''-1} \end{matrix} N(H)_{2-n'''}-H \quad \text{or} \quad (98)$$

$$\begin{matrix} R_2''' \\ \diagdown \\ (R_2'''')_{n'''-1} \end{matrix} N(H)_{2-n'''}-H, \quad (99)$$

or 1 mol of a diol of the formula

HO—$A_2'''$—OH (100)

with 2 mols of a fatty acid of the formula $R_1'''$—COOH (101)

or $R_2'''$—COOH (102)

by methods known per se, $A_1'''$, $A_2'''$, $R_1'''$, $R_1''''$, $R_2'''$, $R_2''''$ and $n'''$ being as defined above and $h'''$ being the number of carboxyl groups of the carboxylic acid of the formula (95).

The reactions are generally carried out at about 120° to about 250° C., preferably up to 200° C., in the melt. If high temperatures of about 200° to 250° C. are used, the resulting products can be purified with active charcoal if need be. Especially if acid anhydrides are used, however, it is also possible to carry out the reactions in the presence of at least one solvent which needs to be inert to every starting and end product. If such solvents are used, the reactions can also be carried out at lower temperatures, for example 30° to 120° C. Examples of possible solvents are acetone, dioxane or halogenated or unhalogenated hydrocarbons such as dichloroethane, carbon tetrachloride, benzene, toluene, chlorobenzene, o-, m- and p-xylene, a technical xylene mixture and mixtures of the hydrocarbons mentioned. If, for example, diols of the formula (100) are reacted with fatty acids of the formulae (101) or (102), it can be advantageous to use a catalyst, for example hydrochloric acid, sulfuric acid, phosphoric acid or organic sulfonic acids, preferably p-toluenesulfonic acid, to accelerate the esterification reactions if necessary. If polycarboxylic acids of the formula (95) are reacted with primary fatty amines of the formula (98) or (99) in which $n'''$ is 1, it is advisable to prevent the formation of by-products by using an approximately equimolar amount (based on the primary fatty amine) of a weak nitrogen-containing base, for example pyridine, triethylamine, isoquinoline or preferably quinoline. If $R_1'''$, $R_1''''$, $R_2'''$ and $R_2''''$ in the formulae (96) to (99), (101) and (102) are an alkenyl radical of the specified type, or $A'''_1$ in the formula (95) is the formula (82), it is furthermore advantageous to carry out the reaction in an inert nitrogen atmosphere and/or in the presence of a polymerisation inhibitor, for example methylene blue, benzothiazine or preferably hydroquinone.

The reactions are generally carried out in one step. However, it is also possible to react in a first stage, for example, the polycarboxylic acid of the formula (95) with a secondary fatty amine of the formula (98) in which $n'''$ is 2 and then, in a second stage, with a primary fatty amine of the formula (99) in which $n'''$ is 1.

Before they are used as component (A) in the paper-sizing process of the invention, the sizing agents need generally not be purified or recrystallised after they have been prepared from (a), (b) and (c), from (a'), (b') and (c'), from (a''$_1$) and (b''$_1$), from (a''$_2$), (b''$_2$) and (c'') or from (a''') and (c''') components, and are thus, as a rule, directly used. This also applies to the intermediates from (a) and (b), (a') and (b') or (a''$_2$) and (b''$_2$) components which thus are, as a rule, not purified or recrystallized before they are further reacted with (c), (c') or (c'') components to obtain the sizing agents (A).

Especially if the sizing agent (A) and the retention aid (B) are added separately (in any order) to the dispersion of the fibres in the process of the invention for sizing paper or cardboard it is advantageous to use the sizing agent at least partly in salt form. If desired, such salts can be obtained after the reaction of components (a), (b) and (c); (a'), (b') and (c'); (a''$_1$) and (b''$_1$); (a''$_2$), (b''$_2$) and (c'') or (a''') and (b''') has ended by converting the resulting reaction products into the corresponding salts, at least partly if desired, by adding e.g. an alkylamine or alkanolamine having a total of at most 6 carbon atoms, for example trimethylamine, triethylamine, ethanolamine, diethanolamine, especially by adding ammonia or an alkali metal hydroxide, for example potassium hydroxide or especially sodium hydroxide, generally in an aqueous medium at room temperature (about 15° to about 25° C.). An alkali metal hydroxide, for example potassium hydroxide or especially sodium hydroxide, or in particular ammonia is advantageously used in the form of its dilute approximately 1 to approximately 10 percent by weight aqueous solution. It is generally advantageous to use at most 2 mols, especially at most 1 mol, preferably 0.1 to 0.9, in particular 0.2 to 0.7, mol of ammonia or alkali metal hydroxide per negative charge present in the anionic sizing agent. The sizing agents in the form of salts thus have e.g. —CH$_2$—,

—SO$_3$H or —COOH groups which are least partly converted into the

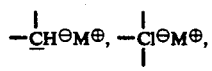

—SO$_3^\ominus$M$^\oplus$ or —COO$^\ominus$M$^\oplus$ groups in which M$^\oplus$ is the corresponding amine, ammonium or alkali metal cation.

Examples of compounds which are partly in the form of a salt and which are suitable for use as sizing agents (A) are especially those which can be obtained by reacting (a) 1 mol of triethanolamine or glycerol with (b) 2 mols of stearic acid, then with (c) 1 to 1.5 mols of chlorosulfonic acid or phosphorus pentoxide and finally with (d) 0.1 to 0.9 equivalent of an aqueous potassium or sodium hydroxide solution, based on the acidic protons of the acidic substituents of the sizing agent, i.e. in the present case of the mixture of acidic esters of (a), (b) and (c).

In addition to the monomeric to oligomeric anionic sizing agent (A) described above, the paper-sizing process of the invention always makes use of a polymeric cationic retention aid (B) which, as a rule, has a molecular weight of about 1,000, preferably about 5,000 to about 2,000,000. Retention aids having molecular weights within the range from 10,000 to 100,000 are particularly preferred. In principle, any commercially available retention aid can be used in the process of the invention. Examples of conventional retention aids (B) which are particularly suitable for use in the paper-sizing process of the invention together with the sizing agent (A) are polyalkyleneimines, epihalogenohydrin adducts of reaction products of polyalkylenepolyamines and aliphatic dicarboxylic acids or of reaction products of polyalkylenepolyamines, dicyanodiamide and free or alkanol-esterified organic dicarboxylic acids, reaction products of dicyanodiamide, formaldehyde, ammonium salts, strong organic acids and of alkylenediamines or polyalkylenepolyamines, cationically modified starches or carbohydrates from carob bean or guar bean flour, copolymers based on polyamide-amines and reaction products of epihalogenohydrins and polymerised diallylamines.

Preferred epichlorohydrin adducts of reaction products of polyalkylenepolyamines and aliphatic dicarboxylic acids have been described, for example, in British Patent 865,727, epichlorohydrin adducts of reaction products of diethylenetriamine and dicyanodiamide, for example, in German "Offenlegungsschrift" 2,710,061 and British Patent 1,125,486, epichlorohydrin adducts of reaction products of diethylenetriamine, dicyanodiamide and free or preferably lower alkanol-esterified dicarboxylic acids, in particular dimethyl adipate, for example in British Patent 1,125,486, and reaction products of dicyanodiamide, formaldehyde, ammonium salts, strong inorganic acids and of ethylenediamine or triethylenetetraamine, for example, in U.S. Pat. No. 3,491,064. Preferred cationically modified starches or carbohydrates from carob bean or guar bean flour are alkylene oxide adducts of these starches or carbohydrates, the alkylene oxide used having 2 or 3 carbon atoms in the alkylene radical and quaternary ammonium groups. Copolymers based on polyamide-amines have molecular weights of $10^3$ to $10^5$, preferably $10^3$ to $10^4$, and can be obtained from, for example, aliphatic saturated dicarboxylic acids having 2 to 10, preferably 3 to 6, carbon atoms, in particular adipic acid, and polyalkylenepolyamines, for example polypropylenepolyamine or polyethylenepolyamine, in particular dimethylaminohydroxypropyl diethylenetriamine.

They are described in, for example, the CTFA Cosmetic Ingredient Dictionary, 3rd edition, 1982, of the Cosmetic, Toiletry and Fragrance Association. Reaction products of epihalogenohydrins and polymerised diallylamines preferably have molecular weights of 1,000 to 2,000, and are described in, for example, U.S. Pat. Nos. 3,700,623 and 4,279,794.

A retention aid (B) which is to the fore of interest for use together with sizing agents (A) in the paper-sizing process of the invention is a corn or potato starch which contains quaternary ammonium groups, has been modified with 1,2-propylene oxide and whose 25% suspension in distilled water at 20° C. has pH 4.2 to 4.6, a polyethyleneimine which has a molecular weight of 10,000 to 100,000, an epichlorhydrin adduct of a reaction product of triethylenetetraamine and dicyanodiamide, an epichlorhydrin adduct of a reaction product of diethylene triamine, dicyanodiamide and dimethyladipate, a reaction product of dicyanodiamide, formaldehyde, ammonium chloride and ethylenediamine, an epichlorhydrin adduct of a poly-N-methyldiallylamine and a copolymer of adipic acid and dimethylamino hydroxypropyl diethylenetriamine.

The process is carried out with, as a rule, 0.02 to 3, preferably 0.1 to 3, in particular 0.2 to 0.8, % by weight of sizing agent (A) and 0.02 to 3, preferably 0.1 to 3, in particular 0.2 to 0.4, % by weight, of retention aid (B), each based on the dry matter in (A) and (B) and on the solids content of the dispersion of the fibres. 0.02 to less than 0.1% by weight of sizing agent (A) and of retention aid (B) are only sufficient for size press control, which is not detectable with conventional sizing tests (cf. for example the article "Control and understanding of size press pickup" by D. R. Dill in the journal TAPPI (Proceedings of the Technical Association of the Pulp and Paper Industry), Volume 57, No. 1, of January 1974, pages 97–100).

The dispersion of the fibres to which the sizing agents (A) and retention aids (B) are added has, as a rule, a solids content of 0.1 to 5, preferably 0.3 to 3, in particular 0.3 to 1% by weight and a Schopper-Riegler freeness of about 10° to about 90°, especially 20° to 60°, preferably 20° to 45°, in particular 25° to 35°. It contains as a rule cellulose, i.e. pulp, in particular from softwood, for example pinewood, or from hardwood, i.e. deciduous wood, for example beech wood, the pulp being prepared by conventional processes, for example the sulfite or especially the sulfate process. The dispersion of the fibres can also contain mechanical woodpulp. The dispersion of the fibres can even contain alum-containing waste paper. Suspensions of cellulose which are prepared by the CMP or CTMP process (Chemimechanical and chemithermomechanical pulping processes, cf. for example the article "Developments in refiner mechanical pulping" by S. A. Collicutt and coworkers in TAPPI, Volume 64, No. 6, of June 1981, pages 57 to 61) are also suitable.

The dispersions of the fibres can also contain organic or mineral fillers. Suitable organic fillers are inter alia synthetic pigments, for example polycondensation products of urea or melamine and formaldehyde which have large specific surface areas, are in a highly disperse form and have been described in, inter alia, British Patents 1,043,437 and 1,318,244, and suitable mineral fillers are, inter alia, montmorillonite, titanium dioxide, calcium sulfate and especially talc, kaolin and/or chalk (calcium carbonate). The dispersion of the fibres generally contains 0 to 40, preferably 5 to 25, in particular 15 to 20, % by weight, based on the solids content of the dispersions of the fibres, in dry matter of fillers of the specified type.

The pH of the dispersion of the fibres can vary within a wide range, for example between about 3.5 and about 10.

Adding calcium carbonate, for example, gives alkaline dispersions of the fibres with a pH of about 7 to about 9, preferably 7.5 to 8.5. Acid dispersions of the fibres with a pH of 3.5 to 7, preferably 5 to 7, in particular 5 to 6, can be obtained in the absence of calcium carbonate by adding acids, for example sulfuric or formic acid, or especially, for example, latent acidic sulfates, such as aluminium sulfate (alum).

Dispersions of the fibres which do not contain filler can exist within a broad pH range from, for example, 3.5 to 10. Those dispersions of the fibres are preferred which have a pH of about 7 to 9, possibly due to added chalk, and the reason they are advantageous is that corrosion on the sensitive paper machines is prevented.

The dispersions of the fibres can also contain additives which increase the fibre/fibre or fibre/filler bond, for example starch or its breakdown products.

High molecular weight polymers of the acrylic acid class, for example polyacrylamides, which have molecular weights above 1,000,000 can also be added to the dispersions of the fibres as auxiliaries for retaining very fine pulp fibre particles, very small amounts of about 0.005 to 0.02% by weight, based on the dry matter in the polymer and the solids content of the dispersions of the fibres being sufficient.

In the process of the invention the dispersion of the fibres is processed in a manner known per se into paper or cardboard on sheet formers or preferably in a continuous operation on paper machines of conventional design. Drying at about 100° to 140° C. for about 0.5 to 10 minutes can give, for example, papers of variable weight per unit area, for example from 50 to 200 g/m².

As mentioned above, the aqueous composition for carrying out the paper-sizing process of the invention contains the sizing agent (A) in addition to optional customary additives if the sizing agent and the retention aid (B) are added separately to the fibre-bearing liquid. In this case the preparation generally contains the sizing agent, as a rule, at least partly in the form of its salts (obtained by using e.g. ammonia, an alkylamine, an alkanolamine or an alkali metal hydroxide of the specified type in the above ratios). Such compositions generally contain 5 to 30, preferably 5 to 20, percent by weight in dry matter of the sizing agent, which is at least partly in form of the salt, based on the weight of the aqueous composition.

However, if the sizing agent (A) and the retention aid (B) are added simultaneously to the fibre-bearing liquid, the aqueous composition, in addition to optional customary additives, contains (A) 2 to 40, preferably 5 to 30, in particular 5 to 10, percent by weight of size (expressed as solids), based on the weight of the aqueous composition, where the size can be in the form of a salt, and (B) 0.1 to 20, preferably 0.5 to 10, in particular 3 to 8, percent by weight of retention agent (expressed as solids), based on the aqueous composition.

Aqueous compositions of the specified type can contain as customary additives surface-active compounds, for example dispersants or emulsifiers and/or water-soluble organic solvents. Examples of suitable dispersants and emulsifiers are conventional lignin sulfonates, ethylene oxide adducts of alkylphenols, fatty amines, fatty alcohols or fatty acids, fatty acid esters of polyhydric alcohols, substituted benzimidazoles or condensation products of aromatic sulfonic acids and formaldehyde. Other surface-active compounds preferably are anionic surfactants, in particular sulfate surfactants, for example diethanolaminelauryl sulfate or ethoxylated lauryl sulfates. Possible water-soluble organic solvents are aliphatic ethers having 1 to 10 carbon atoms, for example dioxane, methylene glycol n-butyl ether or diethylene glycol monobutyl ether or alcohols having 1 to 4 carbon atoms, for example isopropanol, ethanol or methanol.

The compositions are prepared in a customary manner by stirring the sizing agent (A) together with the retention aid (B) or the size (A) generally partly in the form of a salt on its own either in the molten state or preferably in the solid state, in particular in pulverulent form, as a rule in the presence of glass beads and if necessary emulsifiers (in the case of sizing agents in the molten state) or dispersants (in the case of sizing agents in pulverulent form) at most 90° C., preferably about 50° to about 85° C. in the case of emulsions, in particular at about 15° to about 25° C. in the case of dispersions, to give long-shelflife homogeneous emulsions or preferably dispersions. Since the sizing agents together with the retention aids or the sizing agents which are partly in salt form are, as a rule self-dispersing or self-emulsifying, the use of the dispersants or emulsifiers is generally not absolutely necessary. This also applies to the optional addition of solvents and/or surfactants which are only used if the dispersions or emulsions have an inadequate shelf life.

The advantage of the process of the invention is that widely differing dispersions of the fibres can be processed in a simple manner using relatively small amounts of sizing agent and retention aid into paper which has good size properties (ink flotation period and especially Cobb water absorption). The paper which is sized according to the present process has good mechanical properties, i.e. good strengths, in particular a good tear strength. In particular, dispersions of the fibres containing mechanical woodpulp or waste paper can be processed. Another advantage is that the sizing agents used in the invention are compatible with a wide variety of fillers, and also additives thereof, in particular kaolin and alum, in acid dispersions of the fibres. The sizing agents also have advantageous compatibility with fluorescent brightening agents. The whiteness of sized paper is hardly affected by the size, and can, in certain circumstances, even be increased. The generally surprisingly long shelf life of the dispersion of the sizing agents of the specified type, in particular, is of great advantage.

The parts and percentages given in the following methods and working examples are by weight.

METHODS FOR THE MANUFACTURE OF KNOWN COMPOUNDS FOR USE AS INTERMEDIATES

Method A 149 parts of triethanolamine (1 mol), 568 parts of stearic acid (2 mols) and 3.5 parts of p-toluenesulfonic acid as a catalyst are dissolved in 510 parts of p-xylene. This solution is heated to the reflux temperature of about 140° C. and is held at this temperature until the theoretical amount of water formed by the esterification reaction (2 mols) has been azeotropically removed by means of a water separator. The xylene is then distilled off. Left behind as residue are 680 parts of a waxy ester mixture which in addition to homologous monoesters and triesters, contains as main constituent the diester of the formula

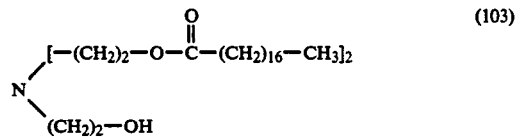

(103)

Melting point: 40°–44° C.

Method B 22 parts of pyrocatechol (0.2 mol) are dissolved in 200 parts of dimethyl sulfoxide, and then admixed with 44.8 parts of a 50% aqueous potassium hydroxide solution (0.4 mol). The reaction mixture is stirred at 20° C. for 30 minutes. 133.2 parts of octadecyl bromide (0.4 mol) are then added to the reaction mixture. The reaction mixture is heated to 50° C., is held at this temperature for 6 hours, is then diluted with 1,000 parts of water and, with an aqueous acetic acid solution is brought to a pH of 4–5, and the reaction product precipitates. The product is filtered off, washed with water and recrystallised from acetone. This gives 98.6 parts of the diether of the formula

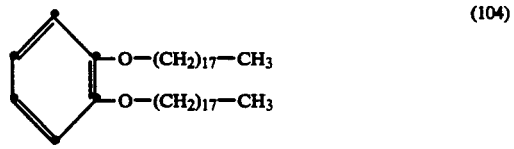

(104)

Melting point: 58°–61° C.

Method C

Method B is followed, except that 22 parts of resorcinol (in place of pyrocatechol) are used, affording 97 parts of the diether of the formula

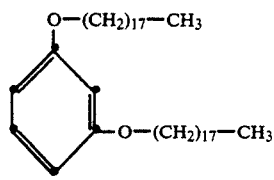

Melting point: 71°-73° C.

Method D 1,136 parts of stearic acid (4.0 mols) are melted at 100° C. 227 parts of diethylenetriamine (2.2 mols) are added in the course of 1 hour, during which the temperature of the reaction mixture rises to 110° C. of its own accord. The reaction mixture is then heated to 160° C. in the course of 2 hours and held at this temperature for 2 hours, during which a slow stream of nitrogen is used to help distill out of the reaction mixture the theoretical amount of water (4 mols) liberated by the reaction together with excess of diethylenetriamine. The reaction mixture is then cooled down to room temperature (15° to 25° C.). This gives 1,232 parts of an amide mixture which is in the form of a yellowish wax and contains as main constituent the diamide of the formula

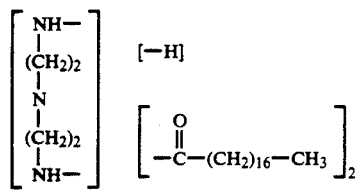

Melting point: 100°-105° C.

Method E

Method D is followed, except that 287 parts of dipropylenetriamine (2.2 mols) are used (in place of 277 parts of diethylenetriamine), affording 1,288 parts of an amide mixture which is in the form of a whitish wax and contains as main constituent the diamide of the formula

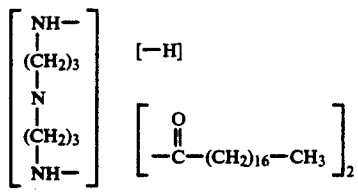

Melting point: 101°-104° C.

Method F

Method D is followed, except that 1,128 parts of oleic acid (4.0 mols) (in place of 1,136 parts of stearic acid) and 1 part of hydroquinone as a polymerisation inhibitor are used and the reaction mixture is held at 160° C. for 3 hours (not 2 hours), affording 1,225 parts of a amide mixture which is in the form of an amber-coloured oil and contains as main constituent the diamide of the formula

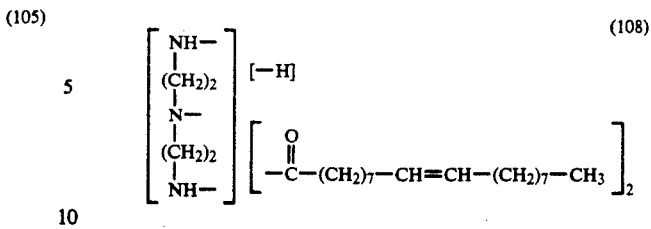

METHODS FOR THE MANUFACTURE OF KNOWN COMPOUNDS FOR USE AS A SIZING AGENT

Method G 624 parts of a technical mixture which, in addition to homologous monoesters and triesters, contains as main constituent 1,3- and 1,2-glycerol distearate (1 mol) are dissolved in 2,000 parts of carbon tetrachloride. Elsewhere, 142 parts of phosphorus pentoxide (1 mol) are dispersed in 500 parts of carbon tetrachloride. The solution of glycerol distearate is then added to the phosphorus pentoxide dispersion in the course of 20 minutes. The reaction mixture is then heated to the reflux temperature of about 76° C. and held at this temperature for 12 hours. The reaction solution is then clarified from impurities. The solvent is removed, and the crude product is recrystallised from methyl ethyl ketone. This gives 650 parts of an ester mixture which is in the form of a beige-coloured powder and contains as main constituent the acidic diester of the formula

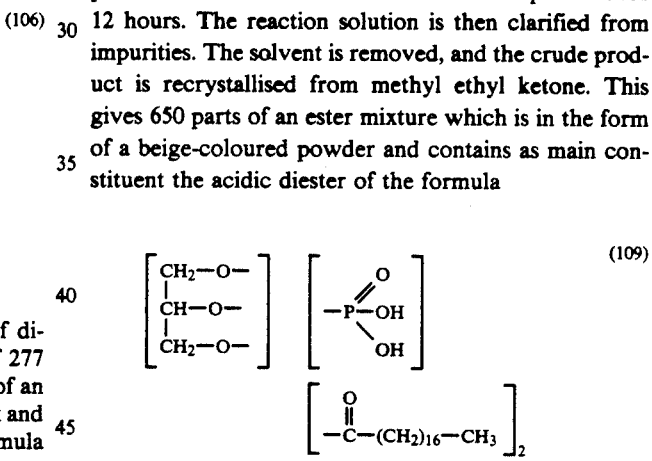

Melting point: 57°-59° C. Acid value: 112.

Method H 320 parts of the amide mixture obtained by Method D (0.5 mol) are suspended at 20° C. in 1,500 parts of chloroform. A solution of 74 parts of phthalic anhydride (0.5 mol) in 800 parts of acetone is added at 20° C. in the course of 35 minutes. The temperature of the reaction mixture rises to 25° C. of its own accord and is held at this temperature for one hour. The reaction mixture is then heated to the reflux temperature of about 57° C. and held at this temperature for one hour during which a clear solution forms. The solvent is then distilled out of the reaction mixture under reduced pressure. This gives 390 parts of a crude product which is in the form of a yellowish powder, can be recrystallised from acetone and contains as main constituent the reaction product of the formula

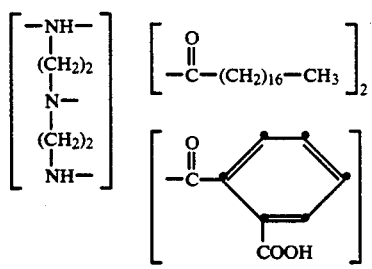
(110)

Melting point (recrystallised product): 77°–78° C.
Acid value (recrystallised product): 73.

Method I

Method H is repeated, except that 50 parts of succinic anhydride (0.5 mol) are used (in place of 74 parts of phthalic anhydride), affording 366 parts of a crude product which is in the form of an ochre-coloured powder, can be recrystallised from ethanol and contains as main constituent a reaction product of the formula

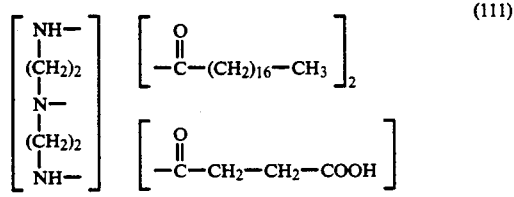
(111)

Melting point (recrystallised product) 108°–112° C.
Acid value (recrystallised product): 68.

Method J

Method H is repeated, except that 77 parts of hexahydrophthalic anhydride (0.5 mol) are used, affording 391 parts of a crude product which is in the form of an ochre-coloured powder, can be recrystallised from acetone and contains as main constituent the reaction product of the formula

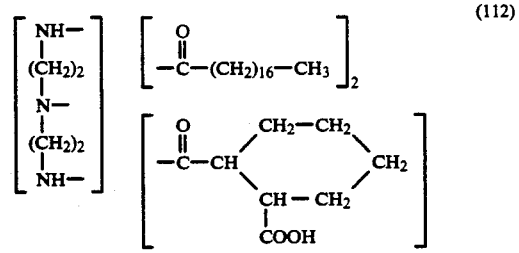
(112)

Melting point (recrystallised product): 66°–69° C.
Acid value (recrystallised product): 66.

Method K

Method H is repeated, except that 49 parts of maleic anhydride (0.5 mol) are used, affording 350 parts of a crude product which is in the form of a yellowish powder, can be recrystallised from acetone and contains as main constituent the reaction product of the formula

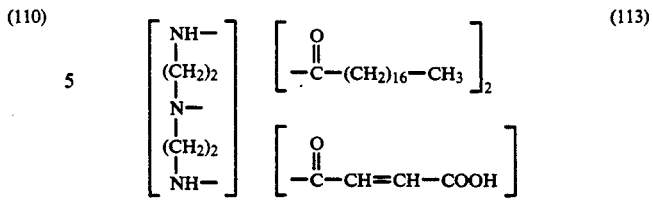
(113)

Melting point (recrystallised product): 82°–87° C.
Acid value (recrystallised product): 88.

Method L

Method H is repeated, except that 56 parts of citraconic anhydride (0.5 mol) are used, affording 360 parts of a crude product which is in the form of an ochre-coloured powder, can be recrystallised from acetone and contains as main constituent the reaction product of the formula

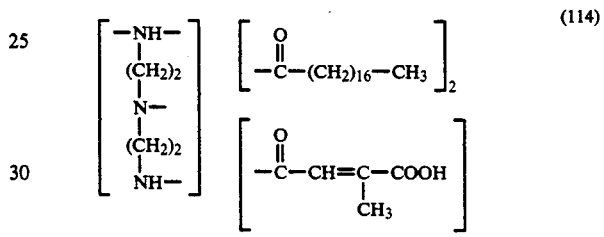
(114)

Melting point (recrystallised product): 71°–75° C.
Acid value (recrystallised product): 82.

Method M

Method H is repeated, except that 232 parts of the amide mixture obtained by Method B (0.5 mol) and 49 parts of maleic anhydride (0.5 mol) are used (in place of 320 parts of the amide mixture obtained by Method A and of 74 parts of phthalic anhydride), affording 370 parts of a crude product which is in the form of a whitish powder, can be recrystallised from acetone and contains as main constituent the reaction product of the formula

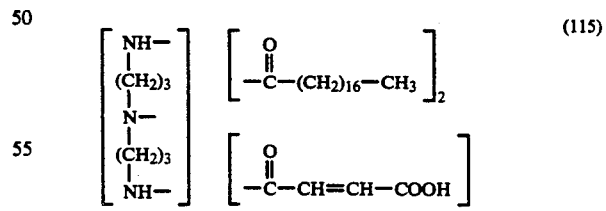
(115)

Melting point (recrystallised product): 89°–100° C.
Acid value (recrystallised product): 72.

Method N

Method H is repeated, except that 313 parts of the amide mixture obtained by Method C (0.5 mol) and 49 parts of maleic anhydride (0.5 mol) are used, affording 350 parts of a brown oil which contains as main constituent the reaction product of the formula

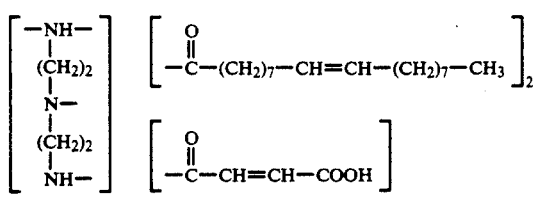

(116)

Acid value: 57.

Method O 320 parts of the amide mixture obtained by Method D (0.5 mol) are melted and heated to 110° C. 96 parts of trimellitic anhydride (0.5 mol) in freshly powdered form are added to this melt. The reaction mixture, which is in the form of a suspension, is heated to 160° C. At 120° to 125° C. an exothermic reaction sets in and the suspended trimellitic anhydride goes into solution. The reaction mixture is then held at 160° C. for 30 minutes and is then cooled down to room temperature (15°–25° C.). This gives 410 parts of a pale brown wax which contains as main constituent the reaction product of the formula

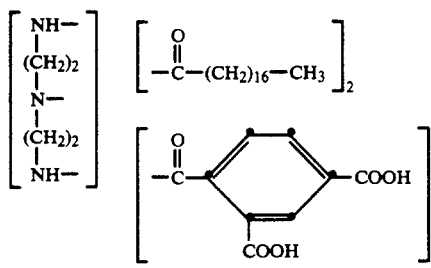

(117)

Melting point: 67°–70° C., acid value: 115.

Method P

Method O is repeated, except that 48 parts (in place of 96 parts) of trimellitic anhydride (0.25 mol) are used, affording 350 parts of a pale brown wax which contains as main constituent the reaction product of the formula (118)

$$\left\{ \begin{bmatrix} -NH- \\ | \\ (CH_2)_2 \\ | \\ N- \\ | \\ (CH_2)_2 \\ | \\ NH- \end{bmatrix}_2 \begin{bmatrix} O \\ \| \\ -C-(CH_2)_{16}-CH_3 \end{bmatrix}_2 \right\}_2$$ 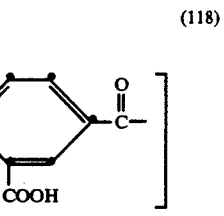

Melting point: 68°–71° C., acid value: 57.

Method Q 635 parts of the amide mixture obtained by Method D (1 mol) are suspended in 150 parts of chloroform. 116 parts of sodium chloroacetate (1 mol) and 102 parts of triethylamine (1 mol), as an acceptor for hydrochloric acid, are added. The reaction mixture is stirred at room temperature (15°–25° C.) for 1 hour, is then heated to the reflux temperature of about 62° C. and is held at this temperature for 1 hour. The solvent is then distilled out of the reaction mixture. The distillation residue is worked up by dissolving it in 500 parts of water, stirring the solution for 15 minutes and then filtering it. This gives 670 parts of a crude product which is in the form of a slightly yellow powder, can be recrystallised from dioxane and contains as main constituent the reaction product of the formula (119)

Melting point (recrystallised product): 103°–107° C.

Method R 52.3 parts of a technical mixture of ⅔ hexadecanol and ⅓ octadecanol (0.2 mol) are dissolved in 250 parts of toluene at 35° C. 13.9 parts of malonyl dichloride (0.1 mol) are added in the course of 30 minutes, during which the temperature of the reaction mixture rises to 40° C. of its own accord and hydrogen chloride gas is liberated. The reaction mixture is then heated to 40° C., is held at this temperature for 24 hours and is then cooled down to 10° C., and the reaction product precipitates. The crude product is filtered off and recrystallised from acetone. This gives 49 parts of colourless crystals of the reaction product of the formula $$R_o-O-\overset{O}{\underset{\|}{C}}-CH_2-\overset{O}{\underset{\|}{C}}-O-R_o \qquad (120)$$

$R_o$ = 67% —(CH_2)_{15}—CH_3
33% —(CH_2)_{17}—CH_3

Melting point: 54°–59° C.

Method S 19 parts of diethyl acetone dicarboxylate (0.1 mol) and 54.1 parts of octadecanol (0.2 mol) are heated to 100° C. and held at this temperature for 24 hours, during which the theoretical amount of ethanol liberated by the trans-esterification reaction (0.2 mol) is distilled out of the reaction mixture. The reaction mixture is then cooled down to 20° C., and the crude product is recrystallised from acetone. This gives 39 parts of a colourless powder of the reaction product of the formula

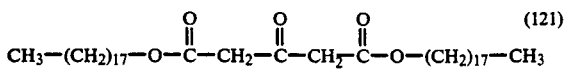

(121)

Melting point: 58°-60° C.

Method T 192 parts of trimellitic anhydride (1 mol) and 540 parts of octadecanol (2 mols) are heated to 160° C. and are held at this temperature for 60 minutes. The reaction mixture is cooled down to 15° to 25° C. to give 690 parts of a colourless waxy ester mixture which contains as main constituent the diester of the formula

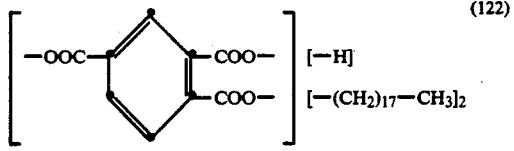

(122)

Melting point: 52°-60° C. Acid value: 90.

Method U

Method T is repeated, except that 218 parts of pyromellitic dianhydride (1 mol) are used (in place of 192 parts of trimellitic anhydride), affording 748 parts of a likewise colourless waxy ester mixture which contains as main constituent the diester of the formula

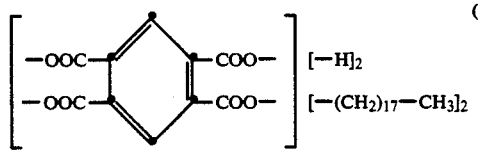

(123)

Melting point: 81°-90° C. Acid value: 135.

Method V

Method T is repeated, except that 218 parts of pyromellitic dianhydride (1 mol) and 484 parts of hexadecanol (2 mols) are used, affording 683 parts of a likewise colourless waxy ester mixture which contains as main constituent the diester of the formula

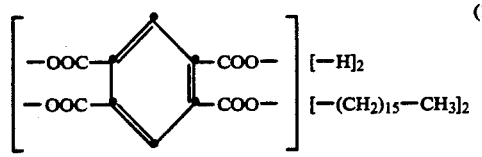

(124)

Melting point: 35°-46° C. Acid value: 132.

Method W

Method T is repeated, except that 218 parts of pyromellitic dianhydride (1 mol) and 810 parts (in place of 540 parts) of octadecanol (3 mols) are used, affording 1,011 parts of a likewise colourless waxy ester mixture which contains as main constituent the triester of the formula

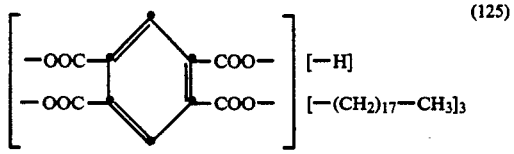

(125)

Melting point: 74°-82° C. Acid value: 51.

Method X 218 parts of pyromellitic dianhydride (1 mol) and 536 parts of oleyl alcohol (2 mols) are heated to 160° C. in an inert nitrogen atmosphere in the presence of 2 parts of hydroquinone as a polymerisation inhibitor and are held at this temperature for one hour. The reaction mixture is cooled down to 15° to 25° C. to give 743 parts of a pale brown liquid creamy ester mixture which contains as main constituent the diester of the formula

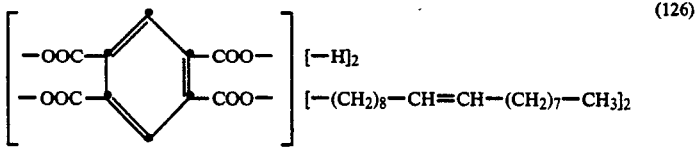

(126)

Acid value: 145.

Method Y 109 parts of pyromellitic dianhydride (0.5 mol) and 521 parts of dioctadecylamine (1 mol) are heated to 160° C. and held at this temperature for 5 hours. The reaction mixture is cooled down to 15° to 25° C. to give 627 parts of an ochre-coloured waxy amide mixture which contains as main constituent the diamide of the formula

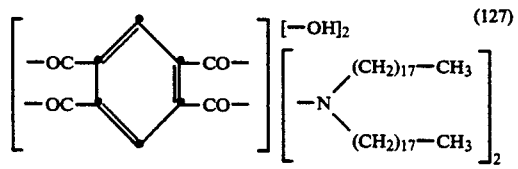

(127)

Melting point: 45°-55° C.
Acid value: 94.

Method Z

A solution of 53.8 parts of octadecylamine (0.2 mol) and 25.8 parts of quinoline (0.2 mol) in 300 parts of acetone is admixed with a solution of 21.8 parts of pyromellitic dianhydride (0.1 mol) in 300 parts of acetone in the course of 30 minutes, during which the temperature of the reaction mixture rises to 40° to 50° C. of its own accord and a white precipitate settles out. The reaction mixture is then stirred for 3 hours, during which the temperature falls from initially 40° to 50° C. to 15° to 35° C. after 3 hours. The reaction mixture is then admixed with 35 parts of an aqueous 38% hydrochloric acid solution and 100 parts of water, and then held at 15° to 25° C. for 30 minutes. The white precipitate formed is filtered off and washed with water until the wash water has pH 6.0. The product is dried at 50° C. under reduced pressure to give 71 parts of an amide mixture which is in the form of a white powder and contains as main constituent the diamide of the formula

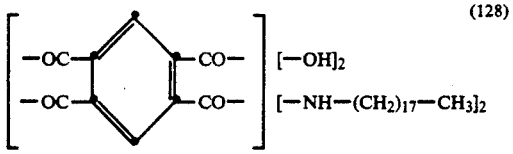
(128)

Melting point: 175°-180° C. Acid value: 150.

Method AA

Method Y is repeated, except that 161 parts of benzophenonetetracarboxylic dianhydride (0.5 mol) are used (in place of 109 parts of pyromellitic dianhydride), affording 664 parts of a likewise ochre-coloured semisolid waxy amide mixture which contains as main constituent the diamide of the formula

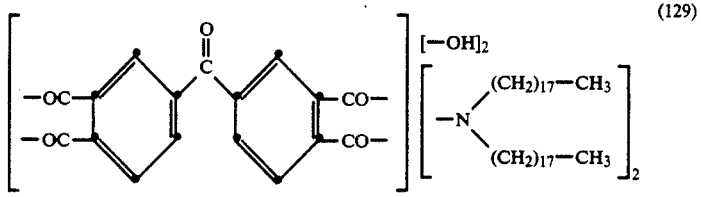
(129)

Acid value: 88.

Method BB

A solution of 315 parts of the amide mixture obtained by Method Y (0.25 mol) and 46 parts of dodecylamine (0.25 mol) in 1,500 parts of toluene is heated to the reflux temperature of about 111° C. and is held at this temperature for 10 hours, during which the water liberated by the reaction is removed by means of a water separator. The toluene is then distilled off under reduced pressure and the product obtained as residue is dried. This gives 343 parts of an ochre-coloured waxy amide mixture which contains as main constituent the triamide of the formula

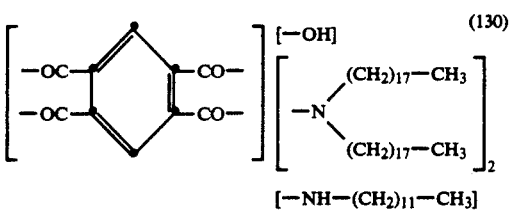
(130)

Melting point: 81°-85° C. Acid value: 41.

Method CC

Method Y is repeated, except that 105 parts of hemimellitic acid (0.5 mol) are used (in place of 109 parts of pyromellitic dianhydride), affording 580 parts of a pale brown waxy amide mixture which contains as main constituent the diamide of the formula

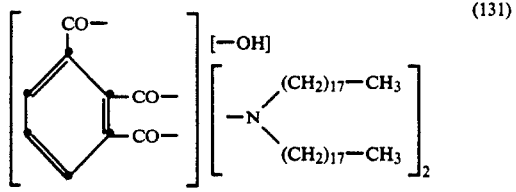
(131)

Melting point: 46°-50° C. Acid value: 44.

Method DD

Method T is repeated, except that 210 parts of citric acid monohydrate (1 mol) are used (in place of 192 parts of trimellitic anhydride) and the length of reaction at 160° C. is 90 minutes (not 60 minutes), affording 672 parts of a colourless waxy ester mixture which contains as main constituent the diester of the formula

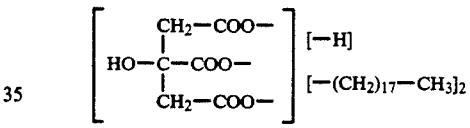
(132)

Melting point: 48°-50° C. Acid value: 83.

Method EE

Method T is repeated, except that 210 parts of citric acid monohydrate (1 mol) (in place of 192 parts of trimellitic anhydride) and 507 parts of a technical mixture of ⅔ hexadecanol and ⅓ octadecanol (2 mols) (in place of 540 parts of octadecanol) are used and the length of reaction at 160° C. is 90 minutes (not 60 minutes), affording 635 parts of a yellowish waxy ester mixture which contains as main constituent the diester of the formula

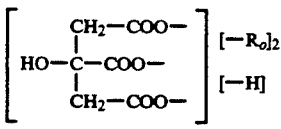
(133)

$R_o$ = 67% —(CH$_2$)$_{15}$—CH$_3$
 33% —(CH$_2$)$_{17}$—CH$_3$

Melting point: 44°-46° C. Acid value: 87.

Method FF

Method T is repeated, except that 210 parts of citric acid monohydrate (1 mol) (in place of 192 parts of trimellitic anhydride) and 1,042 parts of dioctadecylamine (2 mols) (in place of 540 parts of octadecanol) are used and the length of reaction at 160° C. is 70 minutes (not 60 minutes), affording 1,150 parts of a yellowish waxy amide mixture which contains as main constituent the diamide of the formula

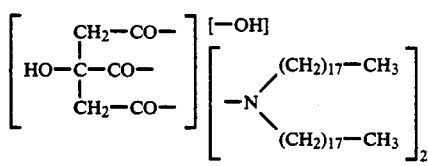

Melting point: 49°–56° C. Acid value: 45.

Method GG 284 parts of stearic acid (1 mol), 67 parts of 2,2-bis(hydroxymethyl)propionic acid (0.5 mol) and 2.5 parts of p-toluenesulfonic acid as a catalyst are dissolved in 200 parts of p-xylene. This solution is heated to the reflux temperature of about 140° C. and is held at this temperature until the theoretical amount of water (1 mol) formed by the esterification reaction has been azeotropically removed by means of a water separator. The p-xylene is then distilled off under reduced pressure, and the product obtained as the residue is dried. This gives 306 parts of a yellowish waxy ester mixture which contains as main constituent the diester of the formula

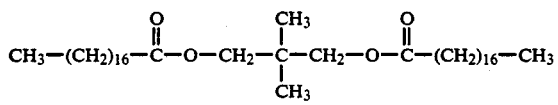

Melting point: 39°–42° C. Acid value: 92.

Method HH 222.3 parts (0.5 mol) of the sodium salt of bis-2-ethylhexyl sulfosuccinate and 270 parts (1.0 mol) of stearyl alcohol are heated to 165°–170° C. together with 2.2 parts (0.04 mol) of sodium methylate. The resulting melt is stirred at this temperature for 3 hours and then allowed to cool down to 90°–95° C., and the 2-ethylhexyl alcohol formed is distilled off under reduced pressure.

This gives as residue of the distillation 360 parts of the sodium salt of bis-octadecyl sulfosuccinate of the formula

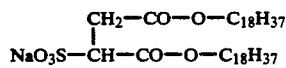

in the form of a yellow waxy product.

EXAMPLES FOR THE MANUFACTURE OF NOVEL COMPOUNDS FOR USE AS INTERMEDIATES

Example 1

Method A is repeated, except that 284 parts of stearic acid (1 mol) and 256 parts of palmitic acid (1 mol) are used (in place of 568 parts of stearic acid), affording 650 parts of a waxy ester mixture which, in addition to homologous monoesters and triesters, contains as main constituent the diester mixture of the formula

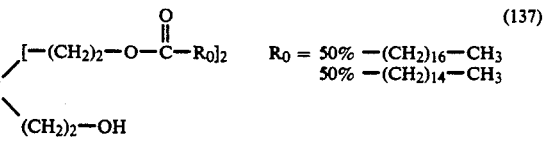

Melting point: 38°–42° C.

Example 2

Method A is repeated, except that 136 parts of pentaerythritol (1 mol), 852 parts of stearic acid (3 mols), 5 parts of p-toluenesulfonic acid and 1,000 parts of p-xylene are used and 3 mols of water are azeotropically removed, affording 930 parts of a waxy ester mixture which, in addition to homologous monoesters, diesters and tetraesters, contains as main constituent the triester of the formula

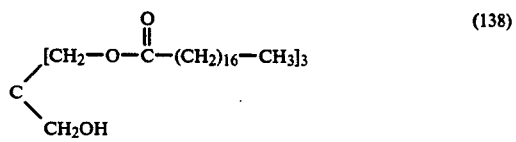

Melting point: 54°–58° C.

Example 3

Method A is repeated, except that 121 parts of tris(-hydroxymethyl)aminomethane (1 mol), 568 parts of stearic acid (2 mols), 3.4 parts of p-toluenesulfonic acid and 600 parts of p-xylene are used and the theoretical amount of 3 mols of water formed by the esterification reaction under ring closure is azeotropically removed, affording 630 parts of a waxy mixture which, in addition to homologous ring-shaped monoesters and triesters, contains as main constituent the diester of the formula

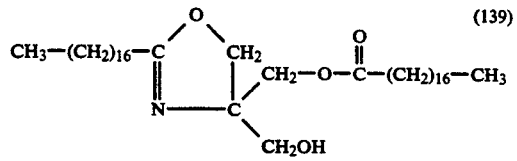

Melting point: 75°–78° C.

Example 4

Method A is repeated, except that 273 parts of laurylamine diethoxylate (1 mol) (prepared from 1 mol of laurylamine and 2 mols of ethylene oxide), 340 parts of behenic acid (1 mol), 2.3 parts of p-toluenesulfonic acid and 625 parts of p-xylene are used and 1 mol of water is azeotropically removed, affording 593 parts of a pale yellow waxy ester mixture which, in addition to the homologous diester, contains as main constituent the monoester of the formula

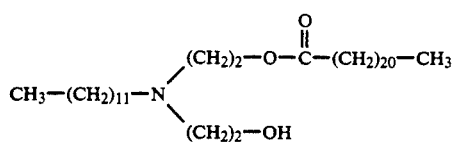
(140)

Melting point: 35°–37° C.

Example 5

Method A is repeated, except that 292 parts of N,N,N',N'-tetrakis(2-hydroxypropyl)ethylenediamine (1 mol), 852 parts of stearic acid (3 mols), 6 parts of p-toluenesulfonic acid and 933 parts of p-xylene are used and 3 mols of water are azeotropically removed, affording 1,085 parts of a waxy ester mixture which, in addition to the homologous monoesters, diesters and tetraesters, contains as main constituent the triester of the formula

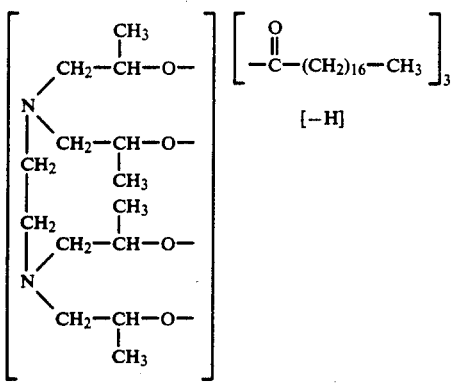
(141)

Melting point: 35°–40° C.

Example 6

Method A is repeated, except that 42.4 parts of 1,2,4-butanetriol (0.4 mol), 227.2 parts of stearic acid (0.8 mol), 1.3 parts of p-toluenesulfonic acid and 270 parts of p-xylene are used and 0.8 mol of water is azeotropically removed, affording 240 parts of a waxy ester mixture which contains as main constituent the diester of the formula

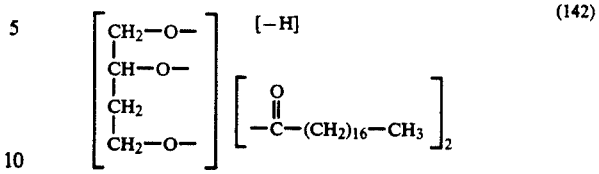
(142)

Melting point: 46°–48° C.

Example 7

Method A is repeated, except that 65.25 parts of tris(-hydroxyethyl) isocyanurate (0.25 mol), 142 parts of stearic acid (0.5 mol), 1,2 parts of p-toluenesulfonic acid and 170 parts of p-xylene are used, 0.5 mol of water is azeotropically removed and the resulting crude product is recrystallised from acetone, affording 150 parts of an ester mixture which is in the form of a white powder and contains as main constituent the diester of the formula

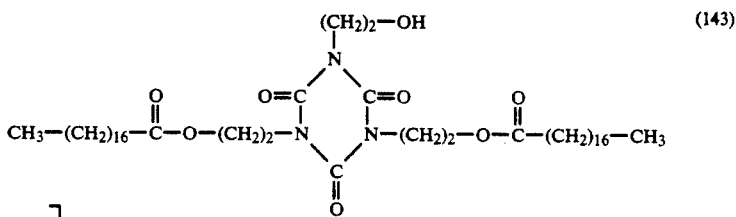
(143)

Melting point: 67°–69° C.

Example 8

201.8 parts of stearylamine (0.75 mol) are dissolved at 50° C. in 700 parts of isopropanol. 74.3 parts of isocyanuric acid triglycide (0.25 mol) (prepared from 1 mol of isocyanuric acid and 3 mols of epichlorohydrin) are introduced into this solution. The reaction mixture is heated to 80° C. and is stirred at this temperature for 5 hours, during which a slightly turbid solution forms. This solution is filtered at 80° C. The reaction product precipitates as the filtrate cools down. The product is filtered off, washed with 200 parts of isopropanol a little at a time and is dried at 35° C. under reduced pressure. This gives 223 parts of a compound of the formula

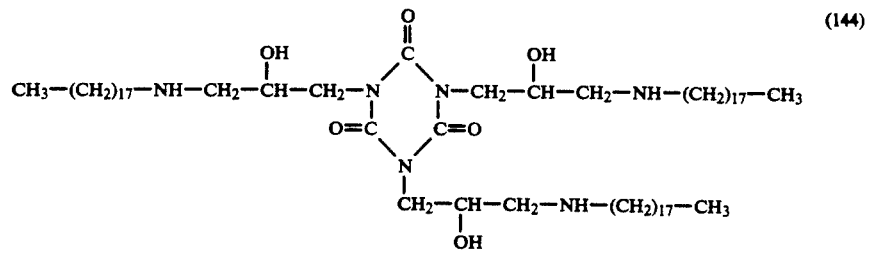
(144)

Melting point: 78°–83° C.

Example 9

167 parts of isocyanuric acid triglycide (0.5 mol), 427 parts of stearic acid (1.5 mols) and 1.5 parts of sodium stearate as a catalyst are heated to 135° C. The heating bath is removed at this temperature. The temperature of the reaction mixture then increases to 160° C. of its own accord. When the exothermic reaction has died down, the reaction mixture is stirred at 150° C. for 3 hours. The melt is then allowed to cool down and solidifies. This gives 594 parts of the compound of the formula is then cooled down to 60° C. and is split into two equal parts. The toluene is distilled out of one half of the reaction mixture at 60° C. under reduced pressure. This gives as distillation residue 34 parts of an amide mixture which is in the form of a beige powder and which con-

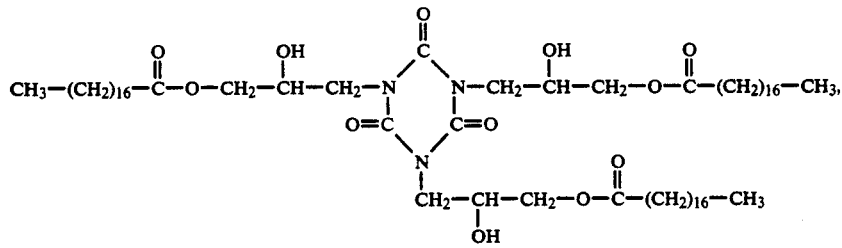
(145)

which is in the form of a pale beige crude product. A sample of the crude product is recrystallised from methanol. The recrystallised product is colourless.

Melting point: 58°-62° C.

Example 10

139 parts of stearylamine (0.5 mol) are dissolved at 75° C. in 400 parts of isopropanol. 50.5 parts (0.25 mol) of butanediol diglycide (prepared from 1 mol of 1,4-butanediol and 2 mols of epichlorohydrin) are added. The reaction solution is heated to 80° C. and is stirred at 80° C. for 4 hours. The solvent is distilled out of the clear solution under reduced pressure. The distillation residue is recrystallised from methanol. This gives 163 parts of a compound of the formula tains as main constituent the reaction product of the formula

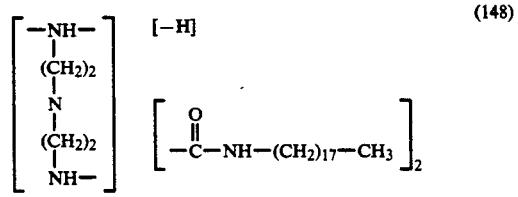
(148)

Melting point: 138°-141° C.

Example 13

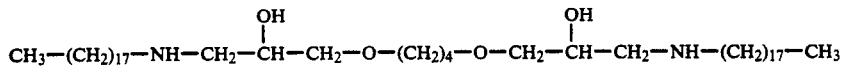
(146)

Melting point: 85°-88° C.

Example 11

76.02 parts of the formula (146) compound obtained in Example 10 (0.1 mol) are dissolved in 200 parts of oxylene at 60° C. 56.9 parts of stearic acid (0.2 mol) are added. This solution is heated to the reflux temperature of about 145° C. and is held at this temperature for about 8 hours until the theoretical amount of water (0.2 mol) formed by the esterification reaction has been azeotropically removed by means of a water separator. The solvent is distilled out of the clear solution under reduced pressure. This gives as distillation residue 128 parts of the compound of the formula 106.7 parts of a technical commercially available mixture which contains as main constituent $N_1$-stearyl-diethylenetetraamine (0.3 mol) are dissolved at room temperature (15°-25° C.) in 300 parts of toluene. A solution of 88.8 parts of octadecyl isocyanate (0.3 mol) in 200 parts of toluene is added, the resulting mixture needing to be cooled to 25° C. and being held at this temperature for 6 hours. The reaction mixture is then heated to 50° C. and is held at this temperature for 2 hours. The toluene is then distilled out of the reaction mixture at 50° C. under reduced pressure, and the reaction residue is recrystallised from methanol. This gives 163 parts of a product mixture which is in the form of a

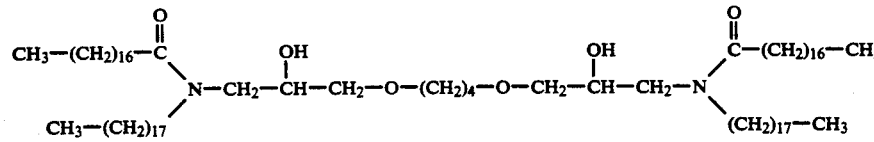
(147)

Melting point: 82°-84° C.

Example 12

A solution of 10.4 parts of diethylenetriamine (0.1 mol) in 80 parts of toluene is admixed at room temperature (15° to 25° C.) with a solution of 59 parts of octadecyl isocyanate (0.2 mol) in 240 parts of toluene in the course of 20 minutes. The temperature of the reaction mixture rises to 50° C. of its own accord. The reaction mixture is then heated to the reflux temperature of about 111° C., is held at this temperature for 15 minutes, colourless powder and which contains as main constituent the reaction product of the formula

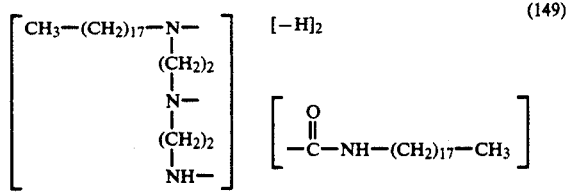 (149)

Melting point: 86°-92° C.

Example 14

177.9 parts of the mixture used in Example 13, which contains as main constituent $N_1$-stearyldiethylenetetraamine (0.5 mol), are melted at 60° C. together with 199.3 parts of methyl stearate (0.5 mol). This melt is heated to 190° C. and held at this temperature until the theoretical amount of methanol liberated by the reaction (0.5 mol) has been distilled out of the reaction mixture. The resulting crude product is recrystallised from ethyl acetate. This gives 296 parts of a product mixture which is in the form of a pale yellow wax and which contains as main constituent the reaction product of the formula

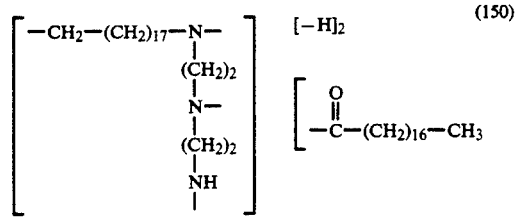 (150)

Melting point: 66°-70° C.

Example 15

53 parts of octadecylamine (0.2 mol) are melted at 35° C. 22.6 parts of ethyl cyanoacetate (0.2 mol) are added at 40° C. The reaction mixture is then held at 40° C. for 2 hours and is then cooled down to room temperature (15°-25° C.), and the reaction product precipitates. The crude product is filtered off, washed with ethanol and recrystallised from toluene. This gives 65 parts of a reaction product which is in the form of a white powder and has the formula

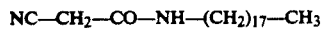

Melting point: 79°-80° C.

EXAMPLES FOR THE MANUFACTURE OF NOVEL COMPOUNDS FOR USE AS SIZING AGENTS

Example 16

681 parts of the ester mixture prepared by Method A (1 mol) are dissolved in 1,000 parts of dichloromethane. 128 parts of chlorosulfonic acid (1.1 mols) are added in the course of 45 minutes, during which the temperature is held between 25° and 35° C. by cooling and escaping hydrogen chloride gas is driven off with nitrogen. When all of the chlorosulfonic acid has been added, the reaction mixture is held at 35° C. for 1 hour. The dichloromethane is then distilled off. The crude product obtained as a residue is recrystallised from methyl ethyl ketone. This gives 620 parts of an ester mixture which is in the form of white powder and which contains as main constituent the acid ester of the formula

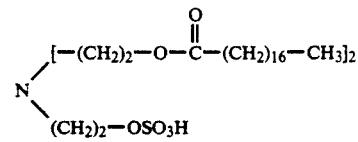 (152)

Melting point: 80°-83° C., acid value: 122.

Example 17

Example 16 is repeated, except that 653 parts of the ester mixture prepared as in Example 1 (1 mol) are used in place of 681 parts of the ester mixture prepared by Method A (1 mol), affording 613 parts of a mixture likewise recrystallised from methyl ethyl ketone, in the form of a white powder and containing as main constituent the acid ester of the formula

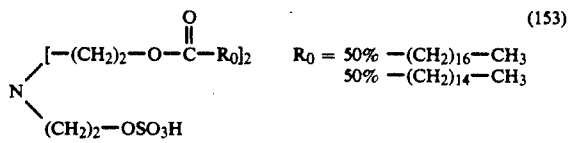 (153)

Melting point: 70°-75° C., acid value: 105.

Example 18

Method D is repeated, except that 681 parts of the ester mixture prepared by Method A (1 mol) are used in place of 624 parts of the ester mixture which contains glycerol distearate as the main component (1 mol), and the crude product is recrystallised from methyl ethyl ketone, affording 600 parts of an ester mixture which is in the form of a white powder and which contains as main constituent the acid ester of the formula

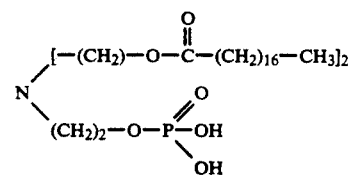 (154)

Melting point: 78°-83° C., acid value: 95.

Example 19

681 parts of the ester mixture prepared by Method A (1 mol), 147 parts of maleic anhydride (1.5 mols), 4 parts of p-toluenesulfonic acid as a catalyst and 0.33 part of hydroquinone as a polymerisation inhibitor are dissolved in 1,000 parts of toluene. This solution is heated to the reflux temperature of about 110° C. and is held at this temperature for 12 hours. The reaction solution is then clarified from impurities. The solvent is distilled off, and the crude product is recrystallised from acetone. This gives 662 parts of an ester mixture which is in the form of a white powder and which contains as main constituent the acid ester of the formula

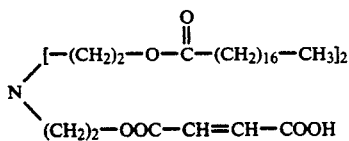
(155)

Melting point: 53°–55° C., acid value: 69.

Example 20

Example 16 is repeated, except that 934 parts of the ester mixture prepared in Example 2 (1 mol), 126.8 parts of chlorosulfonic acid (1.088 mol) and 1,555 parts of dichloromethane are used, the chlorosulfonic acid is added in the course of 30 minutes and the reaction mixture is then held at the reflux temperature of 35° C. for 4 hours, affording 867 parts of an ester mixture likewise recrystallised from methyl ethyl ketone, in the form of a pale beige powder and containing as main constituent the acid ester of the formula

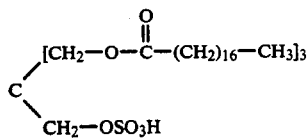
(156)

Melting point: 60°–64° C., acid value: 49.5.

Example 21

Example 16 is repeated, except that 635 parts of the ester mixture prepared in Example 3 (1 mol), 128 parts of chlorosulfonic acid (1.1 mol) and 1,500 parts of dichloromethane are used, the chlorosulfonic acid is added in the course of 30 minutes and the crude product is recrystallised from acetone, affording 622 parts of an ester mixture which is in the form of a white powder and which contains as main constituent the acid ester of the formula

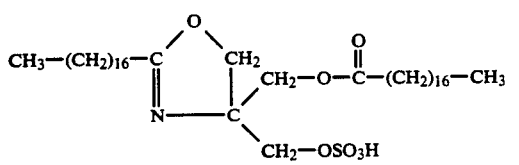
(157)

Melting point: 66°–71° C., acid value: 75.

Example 22

Example 19 is repeated, except that 635 parts of the ester mixture prepared in Example 3 (1 mol), 98 parts of maleic anhydride (1 mol), 18 parts of p-toluenesulfonic acid, 1 part of hydroquinone and 1,500 parts of p-xylene are used and the reaction mixture is held at 110° C. for 8 hours, affording 681 parts of an ester mixture likewise recrystallised from acetone, and containing as main constituent the acid ester of the formula

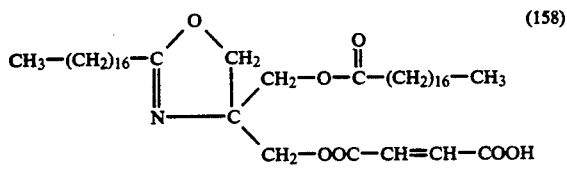
(158)

Melting point: 53°–55° C., acid value: 53.

Example 23

Example 16 is repeated, except that 624 parts of the 1,3- and 1,2-glycerol distearate mixture used in Method D (1 mol), 128 parts of chlorosulfonic acid (1.1 mol) and 666 parts of dichloromethane are used, the chlorosulfonic acid is added in the course of 30 minutes and the crude product is recrystallised from acetone, affording 616 parts of an ester mixture which contains as main constituent the acid ester of the formula

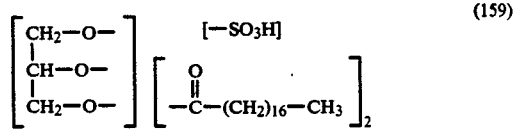
(159)

Melting point: 54°–56° C., acid value: 71.

Example 24

Example 16 is repeated, except that 595 parts of the ester mixture prepared in Example 4 (1 mol), 128 parts of chlorosulfonic acid (1.1 mol) and 800 parts of dichloromethane are used, the chlorosulfonic acid is added in the course of 30 minutes and the crude product is recrystallised from acetone, affording 618 parts of an ester mixture which is in the form of a white powder and which contains as main constituent the acid ester of the formula

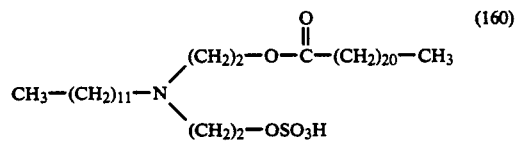
(160)

Melting point: 65°–70° C., acid value: 79.

Example 25

Example 19 is repeated, except that 1,090 parts of the ester mixture prepared in Example 5 (1 mol), 98 parts of maleic anhydride (1 mol), 20 parts of p-toluenesulfonic acid and 2.2 parts of hydroquinone are used in 3,333 parts of toluene, affording 1,027 parts of a waxy ester mixture likewise recrystallised from acetone and containing as main constituent the acid ester of the formula

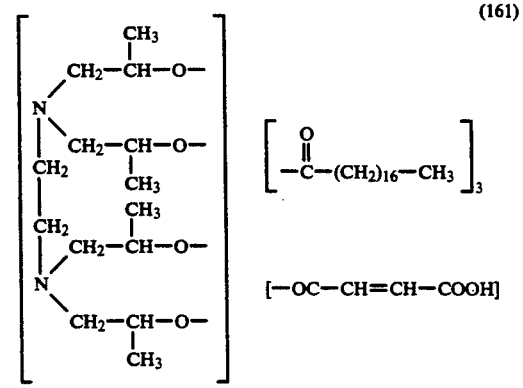
(161)

Melting point: 37°–38° C., acid value: 35.6.

Example 26

Example 16 is repeated, except that 1,090 parts of the ester mixture prepared in Example 5 (1 mol), 116 parts of chlorosulfonic acid (1 mol), and 2,500 parts of dichloromethane are used and the crude product is recrystallised from acetone, affording 1,006 parts of an ester mixture which is in the form of a white powder and which contains as main constituent the acid ester of the formula

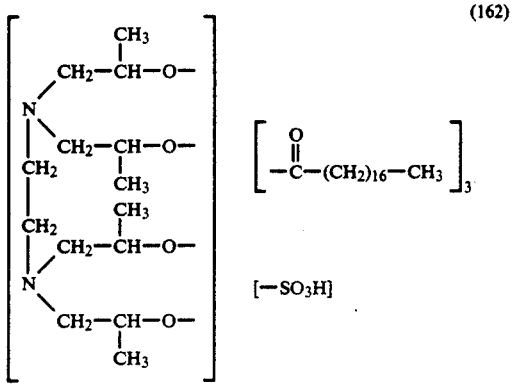
(162)

Melting point: 65°-70° C., acid value: 55.

Example 27

Example 16 is repeated, except that 92.1 parts of the diether obtained by Method B (0.15 mol), 17.5 parts of chlorosulfonic acid (0.15 mol) and 350 parts of dichloromethane are used and the crude product is recrystallised from ethyl acetate, affording 85.3 parts of a sulfonated compound of the formula

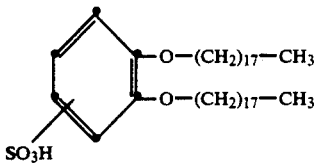
(163)

Melting point: 78°-82° C., acid value: 90.

Example 28

Example 16 is repeated, except that 61.4 parts of the diether obtained by Method C (0.1 mol), 11.56 parts of chlorosulfonic acid (0.1 mol) and 300 parts of dichloromethane are used and the crude product is recrystallised from ethyl acetate, affording 61.8 parts of a sulfonated compound of the formula

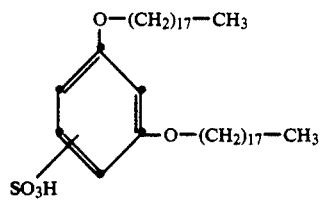
(164)

Melting point 71°-73° C., acid value: 106.

Example 29

95.9 parts of the ester mixture obtained in Example 6 (0.15 mol) and 21.3 parts of phosphorus pentoxide (0.15 mol) are dissolved in 380 parts of toluene. This solution is heated up to 85° C. and stirred at this temperature for 6 hours. The turbid reaction solution is then filtered. The solvent is distilled out of the filtrate under reduced pressure. The crude product obtained as distillation residue is recrystallised from acetone. This gives 103 parts of an ester mixture which is in the form of a beige powder and which contains as main constituent the acid ester of the formula

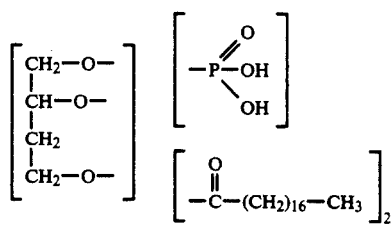
(165)

Melting point: 48°-50° C., acid value: 65.

Example 30

Example 19 is repeated, except that 158.6 parts of the ester mixture prepared in Example 7 (0.2 mol), 19.6 parts of maleic anhydride (0.2 mol), 1.5 parts of p-toluenesulfonic acid and 0.5 part of hydroquinone are used in 150 parts of p-xylene, affording 109 parts of an ester mixture likewise recrystallised from acetone, in the form of a white powder and containing as main constituent the acid diester of the formula

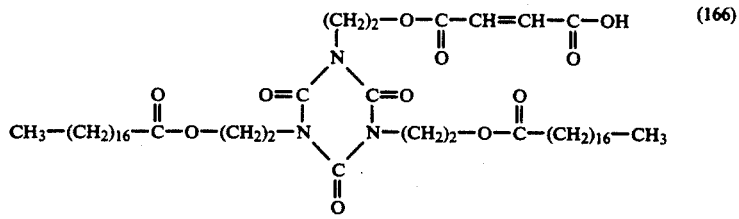
(166)

Melting point: 65°-67° C., acid value: 53.

Example 31

332 parts of the formula (144) compound obtained in Example 8 (0.3 mol) are dissolved in 1,000 parts of isopropanol at 60° C. A solution of 29.4 parts of maleic anhydride (0.3 mol) in 500 parts of methyl ethyl ketone is added while the temperature of the reaction mixture is held at 60° C. The reaction mixture is then held at this temperature for 3 hours and is then cooled down to 15° C., and the reaction product precipitates. The product is filtered off with suction and dried at 35° C. in vacuo. This gives 319 parts of a colourless ester mixture which contains as main constituent the acid ester of the formula

Example 34

Method H is repeated, except that 63 parts of dimethylmaleic anhydride (0.5 mol) are used, affording 360

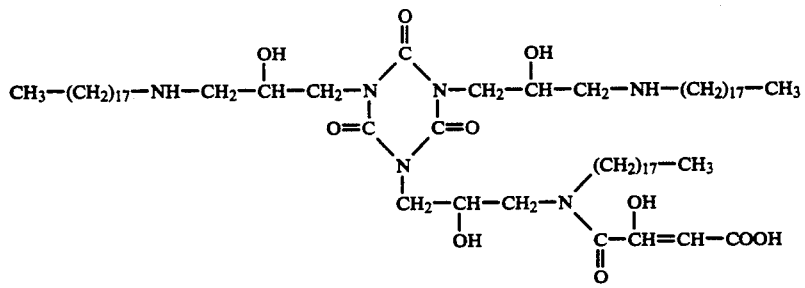
(167)

Melting point: 62°-65° C., acid value: 47.

Example 32

Method D is repeated, except that 229.5 parts of the formula (145) compound obtained in Example 9 (0.2 mol) dissolved in 1,800 parts of carbon tetrachloride and a suspension of 19 parts of phosphorus pentoxide (0.13 mol) in 500 parts of carbon tetrachloride are used and the reaction is carried out at 50° C. for 3 hours, affording 179 parts of a pale beige ester mixture likewise recrystallised from methyl ethyl ketone and containing as main constituent the acid ester of the formula parts of a crude product which is in the form of a whitish powder, can be recrystallised from ethyl acetate and contains as main constituent the acid amide of the formula

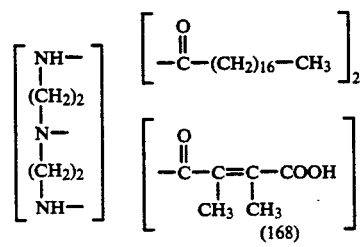
(170)

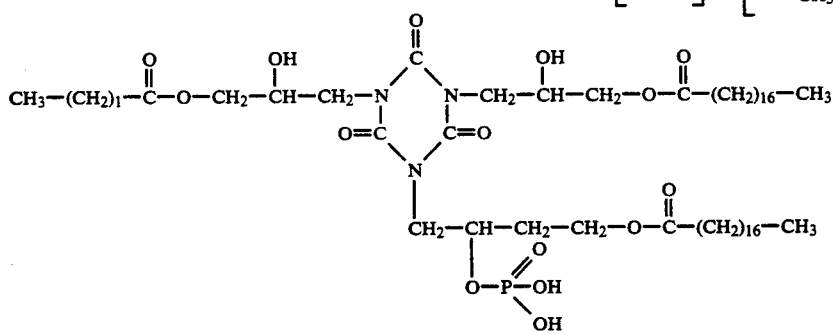

Melting point: 48°-55° C., acid value: 91.

Example 33

153.8 parts of the formula (147) compound (0.1 mol) obtained in Example 11 are mixed with 10 parts of succinic anhydride (0.1 mol), and the mixture is melted at 180° C. and held at this temperature for 6 hours. The resulting crude product is recrystallised from ethyl acetate and dried at 45° C. under reduced pressure. This gives 121.1 parts of a colourless ester mixture which contains as main constituent the acid ester of the formula Melting point (recrystallised product): 66°-72° C. Acid value (recrystallised product): 67.

Example 35

Method H is repeated, except that 56 parts of itaconic anhydride (0.5 mol) are used, affording 360 parts of a crude product which is in the form of a cream-coloured powder, can be recrystallised from acetone and contains as main constituent the reaction product of the formula

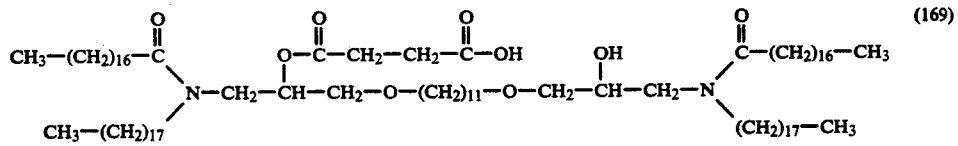
(169)

Melting point: 62°-65° C., acid value: 41.

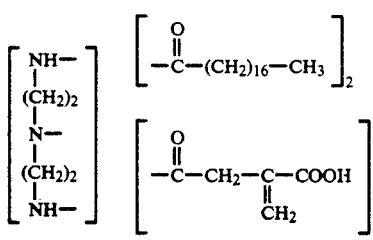 (171)

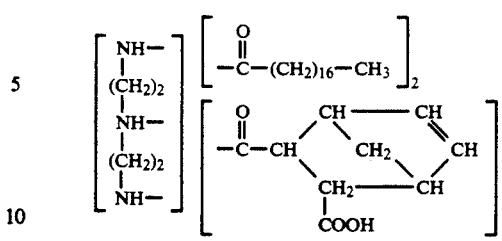 (174)

Melting point (recrystallised product): 79°–83° C.
Acid value (recrystallised product): 87.

Melting point: 63°–64° C., acid value: 61.

Example 36

Method H is repeated, except that 55 parts of pyromellitic anhydride (0.25 mol) are used, affording 360 parts of a crude product which is in the form of a white powder, can be recrystallised from ethyl acetate and contains as main constituent the reaction product of the formula

Example 39

A solution of 49 parts of maleic anhydride (0.5 mol) in 40 parts of toluene is added to 347 parts of the reaction product obtained in Example 12 (0.5 mol), which is in the form of a solution in 160 parts of toluene at 60° C., in the course of 15 minutes, during which the temperature of the reaction mixture rises to 70° C. of its own accord. The reaction mixture is then heated to the reflux temperature of about 111° C., is held at this temperature for 2 hours and is then cooled down to 60° C. The solvent is then distilled out of the reaction mixture under reduced pressure. The distillation residue constitutes 384 parts of a crude product which is in the form of a beige powder, can be recrystallised from dioxane and contains as main constituent the acid amide of the formula

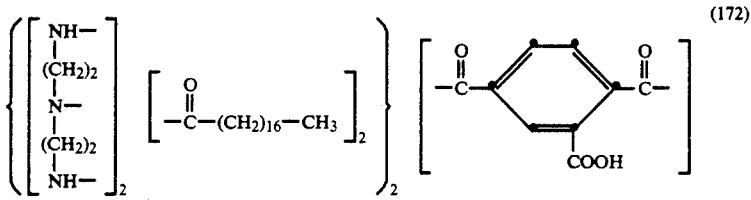 (172)

Melting point (recrystallised product): 124°–130° C.
Acid value: (recrystallised product): 80.

Example 37

Method H is repeated, except that 41 parts of propanesultone (0.5 mol) are used, affording 260 parts of a crude product which is in the form of an ochre-coloured powder, can be recrystallised from ethanol and contains as main constituent the reaction product of the formula

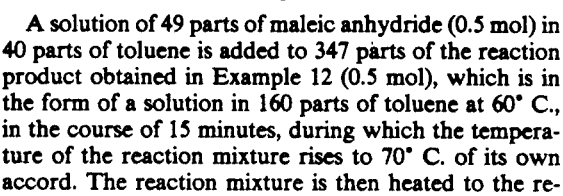 (173)

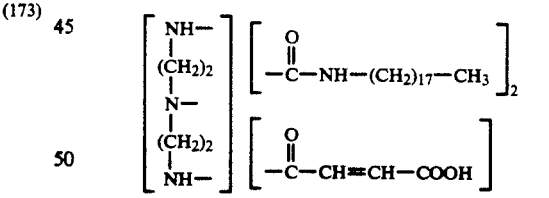 (175)

Melting point (recrystallised product): 96°–99° C.
Acid value (recrystallised product): 49.

Melting point (recrystallised product): 112°–130° C.
Acid value (recrystallised product): 64.

Example 38

320 parts of the amide mixture obtained by Method D (0.5 mol) are melted at 100° C. 82 parts of bicyclo(2,2,1)-hept-5-ene-2,3-dicarboxylic anhydride (0.5 mol) are added. The reaction mixture is stirred, the anhydride goes into solution after 2 to 3 minutes, and the temperature of the reaction mixture rises in the course of about 10 minutes to 115° to 120° C. of its own accord. The reaction mixture is held at 120° C. for 30 minutes and is then cooled down to room temperature (15°–25° C.). This gives 380 parts of a pale brown wax which contains as main constituent the reaction product of the formula

Example 40

195 parts of the product mixture obtained in Example 13 (0.3 mol) are dissolved in 900 parts of toluene. A solution of 30 parts (0.3 mol) of succinic anhydride in 300 parts of methyl ethyl ketone is added at 50° C. The reaction mixture is then heated to 65° C. and held at this temperature for 3 hours. The solvent is then distilled out of the reaction mixture under reduced pressure. The crude product resulting as distillation residue is recrystallised from ethyl acetate. This gives 175 parts of an amide mixture which is in the form of a beige powder and which contains as main constituent the reaction product of the formula

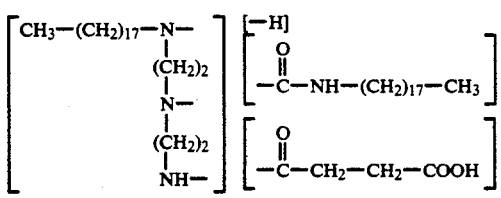 (176)

Melting point: 55°-58° C., acid value: 74.

Example 41

Example 40 is repeated, except that 444 parts of phthalic anhydride (0.3 mol) are used (in place of 30 parts of succinic anhydride), affording 192 parts of an amide mixture which is in the form of a beige powder and which contains as main constituent the reaction product of the formula

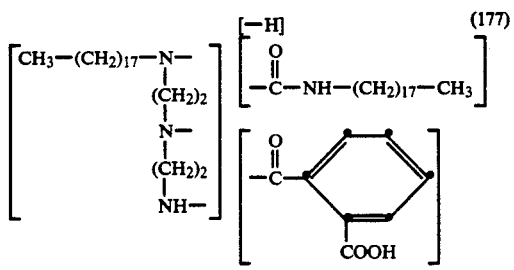 (177)

Melting point 65°-70°, acid value: 70.

Example 42

Example 40 is repeated, except that 34.2 parts of glutaric anhydride (0.3 mol) are used, affording 166 parts of an amide mixture which is in the form of a beige powder and which contains as main constituent the reaction product of the formula

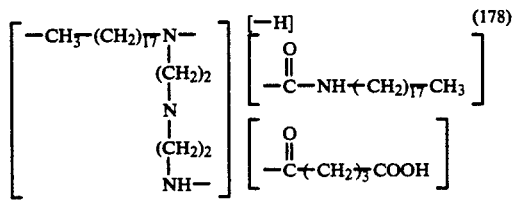 (178)

Melting point: 53°-56° C., acid value: 73.

Example 43

Example 40 is repeated, except that 186.6 parts of the product mixture obtained in Example 3 (0.3 mol) and 29.4 parts of maleic anhydride (0.3 mol) are used and the maleic anhydride is dissolved in 300 parts of toluene (in place of methyl ethyl ketone), affording 182 parts of an amide mixture which is in the form of a beige powder and which contains as main constituent the reaction product of the formula

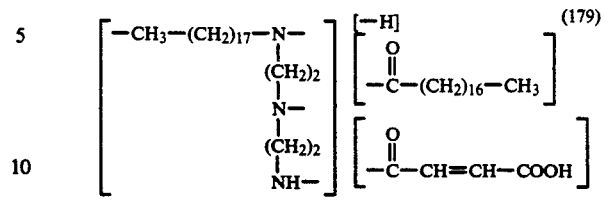 (179)

Melting point: 62°-67° C., acid value: 78.

Example 44

116 parts of triethyl methanetricarboxylate (0.5 mol) and 406 parts of octadecanol (1.5 mols) are heated to 140° C. and held at this temperature for 17 hours, during which the theoretical amount of ethanol liberated by the trans-esterification reaction (1.5 mols) is distilled out of the reaction mixture. The reaction mixture is then cooled down to 20° C., and the crude product is recrystallised from acetone. This gives 300 parts of a reaction product which is in the form of a colourless powder and which has the formula

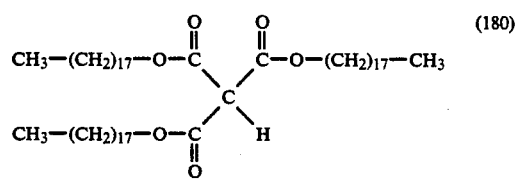 (180)

Melting point: 50°-54° C.

Example 45

67.2 parts of the intermediate obtained in Example 15 (0.2 mol) are dissolved at room temperature (15°-25° C.) in 300 parts of dimethylformamide, and the solution is admixed mixed with 16 parts of a 50% sodium hydroxide solution (0.2 mol) to give a solution of the corresponding sodium salt. 16.8 parts of 1,6-n-hexane diisocyanate (0.1 mol) are then added at 30° C. in the course of 15 minutes. The reaction mixture is then held at 30° C. for 4 hours, is diluted with 1,000 parts of water and is adjusted to pH 4.5 by means of aqueous acetic acid solution, and the reaction product precipitates in the form of a free acid. The crude product is filtered off and recrystallised from ethyl acetate. This gives 61.3 parts of a reaction product which is in the form of a white powder and which has the formula

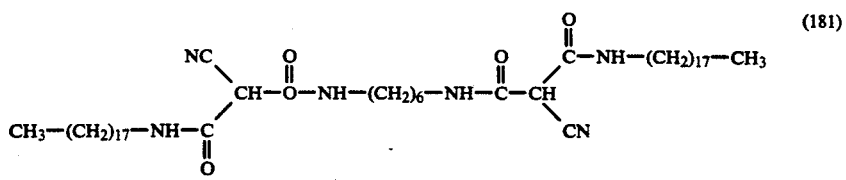 (181)

Melting point: 116°-120° C.

Example 46

Example 45 is repeated, except that the intermediate obtained in Example 15 is dissolved in 200 parts of dimethyl sulfoxide (in place of 300 parts of dimethylformamide) and 17.4 parts of toluylene diisocyanate (0.1 mol) are used in the form of a technical mixture of about 80% of 1-toluylene 2,4-diisocyanate and about 20% of 1-toluylene 2,6-diisocyanate (in place of 16.8 parts of 1,6-n-hexane diisocyanate), affording 68 parts of a reaction product mixture which is in the form of a pale yellow powder and which contains about 80% of the reaction product of the formula

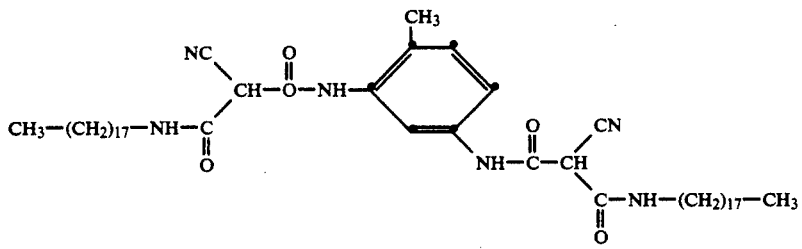

and about 20% of reaction product of the formula

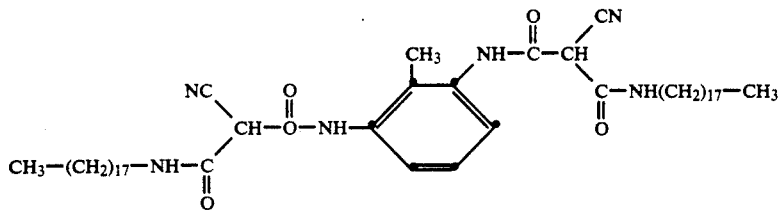

Melting point: 116°-120° C.

Example 47

Method T is repeated, except that 322 parts of benzophenonetetracarboxylic dianhydride (1 mol) are used (in place of 192 parts of trimellitic anhydride), affording 823 parts of a likewise colourless waxy ester mixture which contains as main constituent the diester of the formula

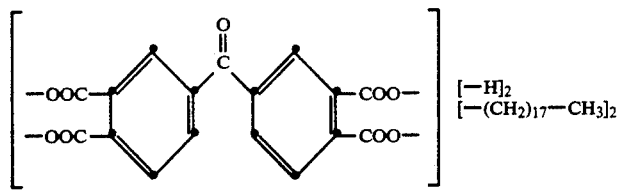

Melting point: 46°-47° C. Acid value: 110.

Example 48

Method T is repeated, except that 176 parts of tricarballylic acid (1 mol) are used (in place of 192 parts of trimellitic anhydride), affording 650 parts of a colourless waxy ester mixture which contains as main constituent the diester of the formula

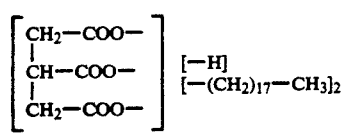
(185)

Melting point: 43°-45° C. Acid value: 85.

Example 49

Method T is repeated, except that 210 parts of citric acid monohydrate (1 mol) (in place of 192 parts of trimellitic anhydride), 270 parts of octadecanol (1 mol) and 521 parts of dioctadecylamine (1 mol) (in place of 540 parts of octadecanol) are used, affording 909 parts (182)

of a yellowish waxy amide and ester mixture which (183)

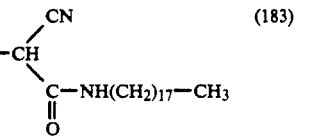

contains as main constituent the amide-ester of the formula

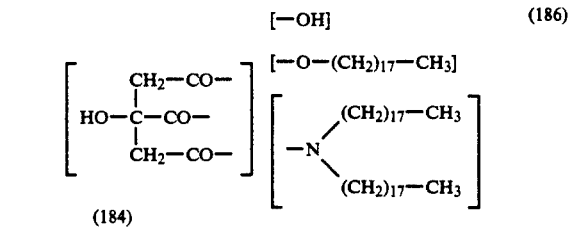
(184)

(186)

Melting point: 54°-67° C. Acid value: 63.

Example 50

Method T is repeated, except that 174 parts of tranaconitic acid (1 mol) are used (in place of 192 parts of trimellitic anhydride), the reaction is carried out in the presence of 1 part of hydroquinone as a polymerisation inhibitor and the length of reaction at 160° C. is 30 minutes (not 60 minutes), affording 650 parts of a colourless waxy ester mixture which contains as main constituent the diester of the formula

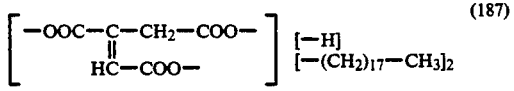

Melting point: 42°-43° C. Acid value: 83.

Example 51

Method T is repeated, except that 87 parts of transaconitic acid (0.5 mol) (in place of 192 parts of trimellitic anhydride) and 521 parts of dioctadecylamine (1 mol) (in place of 540 parts of octadecanol) are used and the reaction is carried out in the presence of 1 part of hydroquinone as a polymerisation inhibitor, affording 560 parts (98% of theory) of a yellowish waxy amide mixture which contains as main constituent the diamide of the formula

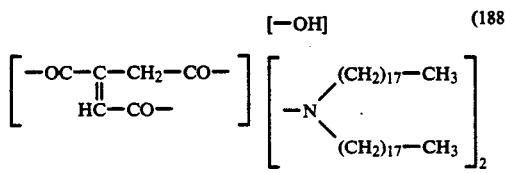

Melting point: 52°-57° C. Acid value: 47.

Example 52

Method GG is repeated, except that 170.4 parts (in place of 284 parts) of stearic acid (0.6 mol), 48.9 parts of N,N-bis(2-hydroxyethyl)glycine (0.3 mol) (in place of 67 parts of 2,2-bis(hydroxymethyl)propionic acid), 1.2 parts (in place of 2.5 parts) of p-toluenesulfonic acid and 170 parts (in place of 200 parts) of p-xylene are used and 0.6 mol (in place of 1 mol) of water is azeotropically removed, affording 208 parts of a yellowish waxy ester mixture which contains as main constituent the diester of the formula

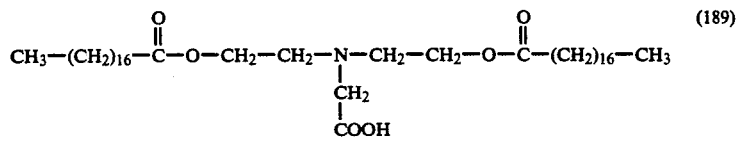

Melting point: 64°-68° C. Acid value: 106.

Example 53

95.6 parts of nitrilotriacetic acid (0.5 mol) and 522 parts of dioctadecylamine (1 mol) are heated to 160° C. and held at this temperature for 6 hours. The reaction mixture is cooled down to 15° to 25° C. to give 565 parts of an ochre-coloured waxy amide mixture which contains as main constituent the diamide of the formula

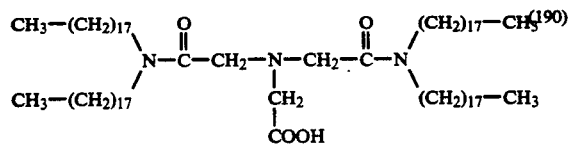

Melting point: 44°-51° C. Acid value: 49.

APPLICATION EXAMPLES

Examples 54 to 75

A dispersion of fibres containing bleached birch sulfate pulp and pine sulfate pulp in a weight ratio of 1:1 in 10° (German degrees of hardness) hard water and having a Schopper-Riegler freeness of 35° and a solids content of 0.5% can be mixed with 20% of the filler given in Table I below and then is mixed with 0.01% of PERCOL 292 ® (cationic high molecular weight (molecular weight $>1\cdot10^7$) polyacrylamide) as an auxiliary for retaining very fine pulp fibre particles, and pH of the dispersion of the fibres which is likewise given in Table I becomes established. The percentages are based on the dry matter in auxiliary and filler and in turn on the solids content of the dispersion of the fibres.

The sizing agent formulations likewise given in Table I below are prepared by stirring the specified sizing agents in powder form or in the form of reaction mixtures as obtained after their manufacture, in the presence of deionised water and of glass beads having a diameter of 2 mm at room temperature (15° to 25° C.), together with the particular retention aid described below. The resulting dispersions are pourable and homogeneous and have a long shelf life. The percentages in the formulations are based on the dry matter in sizing agent and retention aid and in turn on the total weight of the formulation. Retention aid No. 1 is POLYMIN P ® (a polyethyleneimine with a molecular weight of 10,000 to 100,000). Retention aid No. 2 is CATO 110 ® cationically modified starch which has been modified with a propylene oxide containing quaternary ammonium groups and whose pH of 25% suspension in distilled water at 20° C. is 4.2 to 4.6). Retention aid No. 3 is a condensation product of dicyanodiamide and triethylenetetraamine, which has been reacted with epichlorohydrin and is prepared as in Example 2 of German "Offenlegungsschrift" 2,710,061.

The aqueous formulation of the sizing agent and the retention aid is then added to the dispersion of the fibres in such a way that the result is an amount of the sizing agent of 0.5% in dry matter, based on the solids content of the dispersion of the fibres. The dispersion of the fibres is then processed in a Formette Dynamique Laboratory sheet former supplied by Allimand, Grenoble, France, into sheets of paper which on drying at 130° C. for 3 minutes have a weight per unit area of 80 g/m². The sheet of paper thus obtained is subjected to an additional heat treatment, at 140° C., for 3 minutes.

The two surfaces of the sheets of paper obtained, i.e. the surface obtained against the sieve face of the sheet former and the opposite surface, are tested for their size properties. For this purpose, the Cobb water absorption after a 30 second treatment (WA Cobb$_{30}$) is measured in accordance with DIN 53,132. The results of the WA Cobb$_{30}$ measurements on the sieve side (SS) and the opposite side (OS) before and after the heat treatment at 140° C. and before and after one day storage at 20° C. are given in g/m² in Table I below. The lower the water absorption, the better the sizing of the paper. WA Cobb$_{30}$ values above 100 correspond to a completely unsatisfactory sizing of the paper.

TABLE I

| Example No. | Formulation | Filler | pH of the dispersion of the fibres | WA Cobb$_{30}$ (g/m$^2$) | | | | | | | |
|---|---|---|---|---|---|---|---|---|---|---|---|
| | | | | After drying | | | | After heat treatment | | | |
| | | | | immediately | | after 1 day storage | | immediately | | after 1 day storage | |
| | | | | SS | OS | SS | OS | SS | OS | SS | OS |
| 54 | 7% of sizing agent of Example 16 3.5% of retention aid No. 1 | chalk | 8.4 | 21 | 11 | 17 | 11 | 16 | 12 | 14 | 11 |
| 55 | 7% of sizing agent of Example 16 3.5% of retention aid No. 2 3.5% of retention aid No. 3 | chalk | 8.3 | 26 | 15 | 24 | 13 | 14 | 11 | 15 | 13 |
| 56 | 7% of sizing agent of Example 17 3.5% of retention aid No. 2 3.5% of retention aid No. 3 | chalk | 7.8 | 51 | 19 | 46 | 19 | 17 | 30 | 13 | 15 |
| 57 | 7% of sizing agent of Example 18 3.5% of retention aid No. 1 | chalk | 8.2 | 21 | 13 | 15 | 10 | 18 | 14 | 15 | 8 |
| 58 | 7% of sizing agent of Example 19 3.5% of retention aid No. 1 | chalk | 8.4 | 84 | 28 | 15 | 15 | 47 | 20 | 43 | 12 |
| 59 | 7% of sizing agent of Example 20 3.5% of retention aid No. 1 | chalk | 9.0 | 24 | 13 | 22 | 11 | 19 | 12 | 17 | 13 |
| 60 | 7% of sizing agent of Example 21 3.7% of retention aid No. 1 | chalk | 9.0 | 16 | 13 | 14 | 11 | 18 | 14 | 17 | 14 |
| 61 | 7% of sizing agent of Example 22 3.5% of retention aid No. 1 | chalk | 8.4 | 18 | 13 | 15 | 9 | 16 | 12 | 13 | 9 |
| 62 | 7% of sizing agent of Example 23 3.5% of retention aid No. 1 | chalk | 8.0 | 39 | 14 | 28 | 10 | 19 | 14 | 17 | 11 |
| 63 | 7% of sizing agent of Example 24 3.5% of retention aid No. 1 | chalk | 8.8 | 38 | 22 | 37 | 23 | 37 | 21 | 30 | 23 |
| 64 | 7% of sizing agent of Example 25 3.5% of retention aid No. 1 | chalk | 8.7 | 49 | 26 | 44 | 14 | 29 | 14 | 31 | 17 |
| 65 | 7% of sizing agent of Example 26 3.5% of retention aid No. 1 | chalk | 8.5 | 20 | 13 | 23 | 13 | 15 | 13 | 17 | 16 |
| 66 | 7% of sizing agent of Example 27 3.5% of retention aid No. 1 | chalk | 8.7 | 16 | 12 | 15 | 12 | 17 | 13 | 19 | 16 |
| 67 | 7% of sizing agent of Example 28 3.5% of retention aid No. 1 | chalk | 8.8 | 20 | 13 | 22 | 11 | 20 | 16 | 21 | 18 |
| 68 | 7% of sizing agent of Example 29 3.5% of retention aid No. 1 | chalk | 8.9 | 27 | 14 | 27 | 13 | 34 | 16 | 37 | 18 |
| 69 | 7% of sizing agent of Example 30 3.5% of retention aid No. 1 | chalk | 8.3 | 37 | 16 | 38 | 17 | 29 | 18 | 32 | 18 |
| 70 | 7% of sizing agent of Example 31 3.5% of retention aid No. 1 | chalk | 8.3 | 38 | 16 | 16 | 12 | 28 | 14 | 16 | 11 |
| 71 | 7% of sizing agent of Example 32 3.5% of retention aid No. 1 | chalk | 8.4 | 25 | 13 | 25 | 13 | 25 | 15 | 23 | 14 |
| 72 | 7% of sizing agent of Example 33 3.5% of retention aid No. 1 | chalk | 9.1 | 39 | 23 | 23 | 13 | 38 | 19 | 24 | 15 |
| 73 | 7% of sizing agent of Example 16 3.5% of retention aid No. 1 | —* | 5.6 | 27 | 16 | 25 | 14 | 24 | 15 | 21 | 12 |
| 74 | 24% of sizing agent of Example 10 4% of retention aid No. 1 | chalk | 8.2 | 56 | 26 | 36 | 14 | 22 | 16 | 21 | 13 |
| 75 | 7% of sizing agent of Example 34 3.5% of retention aid No.1 | chalk | 8.7 | 23 | 14 | 23 | 13 | — | — | — | — |

*no filler

Examples 76 to 79

The method of Examples 54 to 75 is repeated, except that a formulation of 7% of sizing agent of Method G and 3.5% of retention aid No. 1 is used. In addition, there is used, besides a dispersion of the fibres which is free of mechanical wood pulp, also a dispersion of the fibres which contains bleached birch sulfate pulp, bleached pine sulfate pulp and bleached mechanical wood pulp in a weight ratio of 1:1:2. The sizing results are shown in Table II below.

TABLE II

| Example No. | Mechanical wood pulp * | Filler | pH of the dispersion of the fibres | WA Cobb$_{30}$ (g/m$^2$) | | | | |
|---|---|---|---|---|---|---|---|---|
| | | | | After drying | | | | |
| | | | | immediately | | after 1 day storage | | after 1 week storage |
| | | | | SS | OS | SS | OS | SS |
| 76 | — | chalk | 7.5 | 15 | 13 | 15 | 12 | 16 |
| 77 | — | kaolin | 6 | 17 | 13 | 18 | 13 | 31 |
| 78 | — | ** | 5.6 | 17 | 17 | 18 | 13 | 20 |
| 79 | + | ** | 6.6 | 16 | 14 | 12 | 10 | 10 |

*dispersions of the fibres which are free of mechanical wood pulp + dispersion of the fibres containing mechanical wood pulp
**no filler

Examples 80 to 83

The method of Examples 54 to 75 is repeated, except that only 0.3% (not 0.5%) of dry matter of the sizing agent is used, based on the solids content of the dispersion of the fibres. The sizing results are summarised in Table III below.

TABLE III

| Example No. | Formulation | Filler | pH of the dispersion of the fibres | WA Cobb$_{30}$ (g/m$^2$) After drying | | | |
|---|---|---|---|---|---|---|---|
| | | | | immediately | | after 1 day storage | |
| | | | | SS | OS | SS | S |
| 80 | 7% of sizing agent of Example 16 3.5% of retention aid No. 1 | chalk | 8.2 | 34 | 19 | 35 | 17 |
| 81 | 7% of sizing agent of Example 20 3.5% of retention aid No. 1 | chalk | 8.2 | 41 | 15 | 32 | 13 |
| 82 | 7% of sizing agent of Example 21 3.5% of retention aid No. 1 | chalk | 8.2 | 40 | 23 | 30 | 18 |
| 83 | 7% of sizing agent of Method G 3.5% of retention aid No. 1 | chalk | 8.0 | 23 | 14 | 20 | 13 |

Examples 84 and 85

The method of Examples 54 to 75 is repeated, except that the following formulations of the sizing agent, which is in each case emulsified in the molten state at 80° C. in the presence of water, are used:

Formulation made up in Example 84:
 7% of sizing agent of Example 16
 3.5% of retention aid No. 1
 0.7% of sorbitan monostearate (oil-in-water
 0.7% of an adduct of ethylene oxide and sorbitan monostearate (water-in-oil emulsifier).

Formulation made up in Example 85:
 30% of sizing agent of Example 23
 15% of retention aid No. 1

The two formulations are homogeneous and have a long shelf life.

The sizing results are shown in Table IV below.

TABLE IV

| Example No. | Filler | pH of the dispersion of the fibres | WA Cobb$_{30}$ (g/m$^2$) | | | | | | |
|---|---|---|---|---|---|---|---|---|---|
| | | | After drying | | | | After heat treatment | | | |
| | | | immediately | | after 1 day storage | | immediately | | after 1 day storage | |
| | | | SS | OS | SS | OS | SS | OS | SS | OS |
| 84 | chalk | 8.1 | 19 | 10 | 20 | 13 | 17 | 11 | 15 | 14 |
| 85 | chalk | 8.4 | 58 | 17 | 54 | 19 | 31 | 17 | 29 | 18 |

Examples 86 to 93

The method of Examples 54 to 75 is repeated, except that the sizing agent and the retention aid are added separately to the dispersion of the fibres, the sizing agent in the form of a powder being stirred with an aqueous 5% sodium hydroxide or potassium hydroxide solution in the presence of water and of glass beads to give self-emulsifying likewise homogeneous and long-shelf-life sizing agent formulations as given in Table V below. The Val % indicated denote the number of equivalents of sodium hydroxide or potassium hydroxide for 100 equivalents based on the number of negative charges of acid groups of the particular acid ester used as sizing agent. 10 seconds before or after the sizing agent has been added, the dispersion of fibres is admixed in either case with 0.25% in dry matter of retention aid No. 1, based on the solids content of the dispersion of the fibres. The sizing results are also shown in Table V.

TABLE V

| Example No. | Order in which retention aid is added | Size formulation | Filler | pH of the dispersion of the fibres | WA Cobb$_{30}$ After drying | | | |
|---|---|---|---|---|---|---|---|---|
| | | | | | immediately | | after 1 day storage | |
| | | | | | SS | OS | SS | OS |
| 86 | Before sizing agent | 7% of sizing agent of Ex. 16 10 val % of sodium hydroxide | chalk | 8.1 | 16 | 15 | 18 | 14 |
| 87 | After sizing agent | 7% of sizing agent of Ex. 16 10 val % of sodium hydroxide | chalk | 8.1 | 17 | 15 | 19 | 15 |
| 88 | Before sizing agent | 7% of sizing agent of Ex. 16 90 val % of sodium hydroxide | chalk | 8.2 | 25 | 15 | 46 | 18 |
| 89 | After sizing agent | 7% of sizing agent of Ex. 16 90 val % of sodium hydroxide | chalk | 8.2 | 21 | 18 | 36 | 27 |
| 90 | Before sizing agent | 7% of sizing agent of Method G 90 val % of sodium hydroxide | chalk | 8.2 | 17 | 16 | 14 | 12 |
| 91 | After sizing agent | 15% of sizing agent of Method G 70 val % of potassium hydroxide | chalk | 8.3 | 30 | 17 | 17 | 12 |
| 92 | After sizing agent | 15% of sizing agent of Method G 70 val % of potassium hydroxide | —* | 6.0 | 18 | 14 | 16 | 12 |
| 93 | After sizing | 15% of sizing agent of Method G | — | 7.0 | 19 | 14 | 11 | 18 |

TABLE V-continued

| Example No. | Order in which retention aid is added | Size formulation | Filler | pH of the dispersion of the fibres | WA Cobb30 After drying immediately SS OS | after 1 day storage SS OS |
|---|---|---|---|---|---|---|
| | agent | 70 val % of potassium hydroxide | (mechanical wood pulp)** | | | |

*no filler
**the dispersion of the fibres used in Example 93 contains bleached birch sulfate pulp, bleached pine sulfate pulp and bleached mechanical wood pulp in a weight ratio of 1:1:2 but no filler.

Examples 94 to 111

The method of Examples 54 to 75 is repeated, except that the sizing agent and retention aid are added separately to the dispersion of the fibres, the sizing agent being added 10 seconds after the filler provided a filler has been added. The retention aid is added 10 seconds after the sizing agent and PERCOL 292 ® is added 10 seconds after the retention aid. The dispersion of the fibres used contains 0.3% of alum (calculated as dry $Al_2(SO_4)_3$), based on the solids content of the dispersion, and 1.5 g of sodium sulfate per liter of dispersion. In addition, there is used besides dispersions of the fibres which are free of mechanical wood pulp also dispersion of the fibres which contain bleached birch sulfate pulp, bleached pine sulfate pulp and bleached mechanical wood pulp in a weight ratio of 1:1:2. Some of these dispersions of the fibres are admixed with the amounts of sulfuric acid or sodium hydroxide specified in Tables VI and VII below (as pure substance, based on the solids content of the dispersion of the fibres), the sulfuric acid and the sodium hydroxide being added in the form of dilute aqueous solutions. The sizing agent used is a 15.3% dilutable, homogeneous and stable formulation of a powder of the ester mixture obtained in Example 22 which is dispersed with 65 val % of ammonia in the presence of water and glass beads. Based on the solids content of the dispersions of the fibres, the amounts used are 0.5% of the specified sizing agent (expressed as solids) and 0.25% of retention aid No. 1 (also expressed as solids). The sizing results can be seen from Tables VI and VII.

TABLE VI

Dispersions of the fibres free of mechanical wood pulp

| Example No. | Filler | Sulfuric acid added (%) | Sodium hydroxide added (%) | pH of the dispersion of the fibres | WA Cobb30 (g/m²) after drying immediately SS | OS | after 1 day storage SS | OS | after 2 wks storage SS |
|---|---|---|---|---|---|---|---|---|---|
| 94 | — | 0.74 | — | 3.4 | 39 | 15 | 35 | 14 | 27 |
| 95 | — | — | — | 6.0 | 17 | 15 | 16 | 13 | 17 |
| 96 | — | — | 1 | 9.7 | 18 | 15 | 17 | 13 | 18 |
| 97 | — | — | 4 | 10.7 | 27 | 20 | 27 | 13 | 35 |
| 98 | chalk | — | — | 8.3 | 15 | 14 | 13 | 11 | 14 |
| 99 | kaolin | — | — | 6.5 | 18 | 15 | 18 | 11 | 29 |
| 100 | talc | — | — | 7.5 | 14 | 14 | 14 | 12 | 13 |
| 101 | kaolin | — | 1.02 | 9.5 | 21 | 15 | 18 | 12 | 43 |
| 102 | talc | — | 1.02 | 9.9 | 16 | 12 | 17 | 10 | 22 |

TABLE VII

Dispersions of the fibres containing mechanical wood pulp

| Example No. | Filler | Sulfuric acid added (%) | Sodium hydroxide added (%) | pH of the dispersion of the fibres | WA Cobb30 (g/m²) after drying immediately SS | OS | after 1 day storage SS | OS | after 2 wks storage SS |
|---|---|---|---|---|---|---|---|---|---|
| 103 | — | 0.74 | — | 3.2 | 32 | 13 | 15 | 11 | 13 |
| 104 | — | — | — | 5.9 | 23 | 12 | 13 | 11 | 14 |
| 105 | — | — | 1 | 7.6 | 19 | 12 | 12 | 10 | 12 |
| 106 | — | — | 4 | 10.1 | 29 | 14 | 17 | 12 | 18 |
| 107 | chalk | — | — | 8.6 | 18 | 11 | 12 | 10 | 14 |
| 108 | kaolin | — | — | 6.5 | 34 | 12 | 15 | 9 | 20 |
| 109 | talc | — | — | 6.6 | 23 | 11 | 13 | 9 | 14 |
| 110 | kaolin | — | 1.02 | 7.8 | 20 | 12 | 13 | 10 | 15 |
| 111 | talc | — | 1.02 | 8.1 | 16 | 11 | 12 | 10 | 13 |

Examples 112 to 116

The method of Examples 54 to 75 is repeated, except that sizing agent and retention aid are added separately to the disperion of the fibres and the dispersion of the fibres used contains pine sulfate pulp and bleached mechanical wood pulp in a weight ratio of 1:4. 30% of chalk is added as a filler to the disperion of the fibres. The sizing agent is added 10 seconds after the chalk, the retention aid 10 seconds after the sizing agent and PERCOL 292 ® seconds after the retention aid. The sizing agent used is a 35% dilutable, homogeneous and stable formulation of a melt of the ester mixture obtained in Example 22 which is emulsified at 80° C. with 18 val % of sodium hydroxide in the presence of water. Retention aid No. 4 or No. 5 is used in place of retention aids Nos. 1 to 3. Retention aid No. 4 is a reaction product of dicyanodiamide, formaldehyde, ammonium chloride and ethylenediamine, which is prepared as in Example 1 of U.S. Pat. No. 3,491,064. Retention aid No. 5 is RETAMINOL K ® (a polyethyleneimine with a molecular weight of 20,000 to 40,000). The amounts of sizing agent and retention aid used are given in Table VIII below, these amounts and the amount of filler (30% of chalk) being based on the dry matter in sizing agent, retention aid and filler and on the solids content of the dispersion of the fibres. The sizing results can also be seen from Table VIII below.

No. 1 are added, likewise pourable, homogeneous and long-shelf-life dispersions being obtained and the dispersions of the sizing agents and retention aids being added to the dispersions of the fibres in such a way, that the result is an amount of the sizing agent of 0.5 or 1.0% in dry matter, based on the solids content of the dispersion of the fibres. The sizing results can be seen from Table IX below.

TABLE IX

| Example No. | Sizing agent | Amount (%) | pH of the dispersion of the fibres | WA Cobb (g/m$^2$) | | | |
|---|---|---|---|---|---|---|---|
| | | | | after drying | | after 1 day storage | |
| | | | | SS | OS | SS | OS |
| 117 | Reaction product of Method H | 0.5 | 9.0 | 74 | 56 | 78 | 64 |
| 118 | Reaction product of Method H | 1.0 | 9.2 | 68 | 39 | 77 | 41 |
| 119 | Reaction product of Method K | 0.5 | 8.7 | 19 | 12 | 20 | 13 |
| 120 | Reaction product of Method L | 0.5 | 9.1 | 42 | 22 | 30 | 16 |
| 121 | Reaction product of Method L | 1.0 | 9.2 | 25 | 11 | 23 | 14 |
| 122 | Reaction product of Method M | 0.5 | 9.2 | 27 | 16 | 26 | 15 |
| 123 | Reaction product of Method O | 0.5 | 9.1 | 19 | 15 | 17 | 13 |
| 124 | Reaction product of Method P | 0.5 | 9.2 | 59 | 24 | 42 | 15 |
| 125 | Reaction product of Method P | 1.0 | 9.2 | 47 | 15 | 23 | 12 |
| 126 | Reaction product of Method Q | 1.0 | 9.2 | 59 | 58 | 70 | 68 |
| 127 | Reaction product of Example 35 | 0.5 | 9.2 | 72 | 46 | 81 | 64 |
| 128 | Reaction product of Example 35 | 1.0 | 9.2 | 24 | 13 | 20 | 14 |
| 129 | Reaction product of Example 36 | 0.5 | 9.2 | 23 | 14 | 20 | 12 |
| 130 | Reaction product of Example 38 | 0.5 | 9.4 | 90 | 77 | 16 | 12 |
| 131 | Reaction product of Example 38 | 1.0 | 9.2 | 75 | 66 | 15 | 12 |
| 132 | Reaction product of Example 39 | 0.5 | 8.9 | 65 | 19 | 61 | 14 |
| 133 | Reaction product of Example 40 | 0.5 | 8.9 | 19 | 15 | 17 | 12 |
| 134 | Reaction product of Example 41 | 0.5 | 8.9 | 34 | 16 | 37 | 14 |
| 135 | Reaction product of Example 42 | 0.5 | 8.9 | 28 | 17 | 24 | 15 |
| 136 | Reaction product of Example 43 | 0.5 | 8.8 | 20 | 13 | 16 | 11 |

Similar results are obtained when the amide mixture of Method I, J or N or of Example 34 or 37 is used.

Examples 137 to 141

The method of Examples 54 to 75 is repeated in which 20% of chalk is added as a filler, except that formulations of 7% of the sizing agents which are specified in the Table X below and 3.5% of retention aid No. 1 or No. 2 are added, likewise pourable, homogeneous and long-shelf-life dispersions being obtained and the dispersions of the sizing agents and retention aids being added to the dispersions of the fibres in such a way, that the result is an amount of the sizing agent of 0.4 or 0.5% in dry matter, based on the solids content of the dispersion of the fibres. The sizing results can be seen from Table X below.

TABLE VIII

| Example No. | Amount of the sizing agent (%) | Retention aid | Amount of the Retention aid (%) | pH of the dispersion of the fibres | WA Cobb$_{30}$ (g/m$^2$) after drying | | | |
|---|---|---|---|---|---|---|---|---|
| | | | | | immediately | | after 1 day storage | |
| | | | | | SS | OS | SS | OS |
| 112 | 0.5 | No. 4 | 1 | 8.4 | 63 | 15 | 55 | 19 |
| 113 | 1 | No. 5 | 0.02 | 7.9 | 40 | 11 | 38 | 9 |
| 114 | 1 | No. 5 | 0.25 | 8.0 | 14 | 10 | 11 | 8 |
| 115 | 0.2 | No. 5 | 0.5 | 8.2 | 46 | 20 | 38 | 13 |
| 116 | 1 | No. 5 | 0.5 | 8.2 | 13 | 10 | 11 | 7 |

Examples 117 to 136

The method of Examples 54 to 75 is repeated, in which 20% of chalk is added as a filler, except that formulations of 7% of the sizing agents which are specified in the Table IX below and 3.5% of retention aid

TABLE X

| Example No. | Sizing agent | Retention aid | Amount of the sizing agent (%) | pH of the dispersion of the fibres | WA Cobb$_{30}$ (g/m$^2$) | | | | | | | |
|---|---|---|---|---|---|---|---|---|---|---|---|---|
| | | | | | Before heat treatment | | | | After heat treatment | | | |
| | | | | | immediately | | after 1 day storage | | immediately | | after 1 day storage | |
| | | | | | SS | OS | SS | OS | SS | OS | SS | OS |
| 137 | Reaction product of Method R | No. 2 | 0.5 | 7.4 | 31 | 20 | 37 | 17 | 15 | 12 | 15 | 9 |
| 138 | Reaction product of Method S | No. 1 | 0.5 | 8.4 | 21 | 13 | 19 | 12 | 18 | 12 | 19 | 9 |
| 139 | Reaction product of Example 44 | No. 1 | 0.5 | 8.0 | 49 | 17 | 40 | 17 | 21 | 14 | 18 | 12 |
| 140 | Reaction product of Example 45 | No. 2 | 0.4 | 7.9 | 36 | 22 | 14 | 14 | 16 | 15 | 15 | 12 |

TABLE X-continued

| Example No. | Sizing agent | Retention aid | Amount of the sizing agent (%) | pH of the dispersion of the fibres | WA Cobb30 (g/m²) | | | | | | | |
|---|---|---|---|---|---|---|---|---|---|---|---|---|
| | | | | | Before heat treatment | | | | After heat treatment | | | |
| | | | | | immediately | | after 1 day storage | | immediately | | after 1 day storage | |
| | | | | | SS | OS | SS | OS | SS | OS | SS | OS |
| 141 | Reaction product of Example 46 | No. 2 | 0.4 | 7.9 | 62 | 24 | 17 | 14 | 18 | 15 | 16 | 12 |

Examples 142 to 167

The method of Examples 54 to 75 is repeated in which 20% of chalk is added as a filler, except that formulations of 7% of the sizing agents which are specified in the Table XI below and 3.5% of retention aid No. 1 are added, likewise pourable, homogeneous and long-shelf-life dispersions being obtained and the dispersions of the sizing agents and retention aids being added to the dispersions of the fibres in such a way, that the result is an amount of the sizing agent of 0.25, 0.35, 0.5 or 1.0% in dry matter, based on the solids content of the dispersion of the fibres. The sizing results can be seen from Table XI below.

Examples 168 to 172

The method in Examples 54 to 75 is repeated, except that sizing agent and retention aid are added separately to the dispersion of the fibres, 7% of sizing agent in the liquid or molten state being stirred at 80° C. together with an aqueous 5% ammonia solution in the presence of water to give a self-emulsifying, likewise pourable, homogeneous and long-shelf-life emulsion and the sizing agent formulations given in Table XII below being formed. The val % shown denote the number of equivalents of ammonia for 100 equivalents based on the number of —COOH groups present in the particular ester or amide mixture used as sizing agent. 10 seconds after 0.5% or 1% in dry matter of sizing agent have been added, the dispersion of the fibres is admixed with respectively half the amount, i.e. 0.25% or 0.5%, in dry matter of retention aid No. 1, the amounts of sizing agent and retention aid being based on the solids content of the dispersion of the fibres. The sizing results can also be seen from Table XII.

TABLE XI

| Example No. | Sizing agent | Amount (%) | pH of the dispersion of the fibres | WA Cobb30 (g/m²) | | | | After 2 weeks storage |
|---|---|---|---|---|---|---|---|---|
| | | | | After drying | | After 1 day storage | | |
| | | | | SS | OS | SS | OS | SS |
| 142 | Ester mixture of Method T | 0.5 | 8.4 | 21 | 12 | 18 | 11 | 23 |
| 143 | Ester mixture of Method U | 0.5 | 8.1 | 22 | 12 | 19 | 12 | 22 |
| 144* | Ester mixture of Method V | 0.5 | 8.1 | 26 | 12 | 22 | 12 | 32 |
| 145 | Ester mixture of Method W | 0.5 | 8.9 | 16 | 12 | 15 | 11 | 22 |
| 146 | Amide mixture of Method X | 0.5 | 8.3 | 16 | 11 | 15 | 10 | 14 |
| 147 | Amide mixture of Method Y | 0.5 | 8.7 | 19 | 11 | 15 | 11 | 15 |
| 148 | Amide mixture of Method Z | 0.5 | 8.1 | 75 | 41 | 78 | 45 | 89 |
| 149 | Amide mixture of Method Z | 1.0 | 8.5 | 52 | 14 | 44 | 14 | 49 |
| 150 | Amide mixture of Method BB | 0.5 | 8.8 | 87 | 27 | 74 | 32 | 75 |
| 151 | Amide mixture of Method BB | 1.0 | 8.5 | 34 | 11 | 40 | 13 | 22 |
| 152 | Amide mixture of Method CC | 0.5 | 8.5 | 21 | 12 | 19 | 10 | 17 |
| 153 | Amide mixture of Method DD | 0.5 | 8.5 | 15 | 12 | 14 | 12 | 16 |
| 154 | Ester mixture of Method DD | 0.35 | 8.3 | 22 | 13 | 21 | 12 | 22 |
| 155 | Ester mixture of Method DD | 0.25 | 8.4 | 35 | 20 | 31 | 19 | 37 |
| 156 | Ester mixture of Method EE | 0.5 | 8.5 | 20 | 12 | 16 | 11 | 17 |
| 157 | Ester mixture of Method EE | 0.35 | 8.5 | 22 | 13 | 21 | 12 | 22 |
| 158 | Ester mixture of Method EE | 0.25 | 8.6 | 28 | 15 | 28 | 14 | 31 |
| 159 | Amide mixture of Method FF | 0.5 | 8.8 | 31 | 15 | 21 | 11 | 21 |
| 160 | Ester mixture of Example 47 | 0.5 | 8.4 | 21 | 12 | 18 | 12 | 35 |
| 161 | Amide mixture of Example 48 | 0.5 | 8.8 | 31 | 13 | 19 | 11 | 26 |
| 162 | Amide ester mixture of Example 49 | 0.5 | 8.8 | 30 | 15 | 18 | 11 | 22 |
| 163** | Ester mixture of Example 50 | 1.0 | 8.9 | 20 | 15 | 15 | 12 | 18 |
| 164 | Amide mixture of Example 51 | 0.5 | 8.8 | 49 | 21 | 23 | 12 | 22 |
| 165** | Amide mixture of Example 51 | 0.5 | 8.9 | 37 | 20 | 27 | 13 | 21 |
| 166 | Ester mixture of Example 52 | 0.5 | 8.3 | 44 | 13 | 42 | 12 | 51 |
| 167 | Amide mixture of Example 53 | 1.0 | 8.7 | 36 | 15 | 26 | 12 | 19 |

*In Example 144, the sizing agent is formulated at 80° C. while in the state of a melt.
**In examples 163 and 165, the size formulation is prepared in the presence of 0.7% of a mixture in the weight ratio of 1:1 of sorbitan monostearate and its adduct with ethylene oxide.

TABLE XII

| Example No. | Sizing formulation | Amount of the sizing agent (%) | pH of the dispersion of the fibres | WA Cobb30 (g/m²) | | | | After 2 weeks storage |
|---|---|---|---|---|---|---|---|---|
| | | | | After drying | | After 1 day storage | | |
| | | | | SS | OS | SS | OS | SS |
| 168 | 7% Liquid ester mixture of Method X 100 val % of ammonia | 0.5 | 8.3 | 89 | 78 | 58 | 43 | 84 |
| 169 | 7% Liquid ester mixture of Method X 100 val % of ammonia | 1.0 | 8.3 | 29 | 26 | 20 | 18 | 102 |

TABLE XII-continued

| Example No. | Sizing formulation | Amount of the sizing agent (%) | pH of the dispersion of the fibres | WA Cobb$_{30}$ (g/m$^2$) | | | | |
|---|---|---|---|---|---|---|---|---|
| | | | | After drying | | After 1 day storage | | After 2 weeks storage |
| | | | | SS | OS | SS | OS | SS |
| 170 | 7% molten amide mixture of Method AA 100 val % of ammonia | 0.5 | 8.2 | 18 | 13 | 17 | 13 | 25 |
| 171 | 7% molten amide mixture of Method AA 200 val % of ammonia | 0.5 | 8.2 | 19 | 13 | 19 | 14 | 39 |
| 172 | 7% molten ester mixture of Method GG 100 val % of ammonia | 0.5 | 8.2 | 30 | 16 | 29 | 16 | 80 |

Examples 173 to 180

The method of Examples 54 to 75 is repeated, except that the filler specified in Table XIII below is used and the sizing agent and the retention aid are added separately to the dispersion of the fibres, 15% of sizing agent in powder form being stirred together with an aqueous 5% ammonia solution in the presence of water and glass beads to give self-emulsifying, likewise homogeneous and long-shelf-life sizing agent formulations given in Table XIII below. The val % shown denote the number of equivalents of ammonia for 100 equivalents based on the number of —COOH groups present in the particular ester or amide mixture used as sizing agent. 10 seconds after 0.4% in dry matter of sizing agent has been added, the fibre-bearing liquid is admixed with 0.2% in dry matter of retention aid No. 1. The filler, sizing agent and retention aid amounts are based on the solids content of the dispersion of the fibres. This also holds for the alum amount. The sizing results are also shown in Table XIII.

separately to the dispersion of the fibres and that no PERCOL 292 ® is used as an auxiliary. As the filler, there is added 20% of chalk to the dispersion of the fibres. The addition of the sizing agent is carried out 10 seconds after the addition of the chalk and the addition of the retention aid 10 seconds after the addition of the sizing agent. As the sizing agents, there are used the emulsions and dispersions which are indicated in the following Table XIV. Retention aid No. 6 or No. 7 is used instead of one of the retention aids Nos. 1 to 3. Retention aid No. 6 is an epichlorohydrin adduct of a reaction product of dicyanodiamide, diethylene triamine and dimethyl adipate which is prepared as in Example 7 of British Patent 1,125,486. Retention aid No. 7 is a copolymer of adipic acid and dimethylamino hydroxypropyl diethylene triamine, this copolymer having a molecular weight of 1,000 to 10,000. The sizing agents and retention aids are used in the amounts which are indicated in the following Table XIV, these amounts and the amount of filler (20% of chalk) being based on dry matter of sizing agent, retention aid and filler and on

TABLE XIII

| Example No. | Sizing agent | Filler | pH of the dispersion of the fibres | WA Cobb$_{30}$ (g/m$^2$) | | | | | |
|---|---|---|---|---|---|---|---|---|---|
| | | | | After drying | | After 1 day storage | | After 2 weeks storage | |
| | | | | SS | OS | SS | OS | SS | OS |
| 173 | 15% ester mixture of Method W 100 val % of ammonia | 20% of chalk (in the presence of 1.5 g of Na$_2$SO$_4$/liter of liquor) | 8.5 | 28 | 12 | 28 | 12 | 47 | 16 |
| 174 | 15% amide mixture of Method Y 50 val % of ammonia | 20% of chalk (in the presence of 1.5 g of Na$_2$SO$_4$/liter of liquor) | 8.5 | 26 | 13 | 22 | 11 | 41 | 13 |
| 175 | 15% ester mixture of Method W 100 val % of ammonia | 20% of chalk (in the presence of 1.5% of Al$_2$(SO$_4$)$_3$) | 8.0 | 22 | 14 | 20 | 12 | 44 | 17 |
| 176 | 15% amide mixture of Method Y 50 val % of ammonia | 20% of chalk (in the presence of 1.5% of Al$_2$(SO$_4$)$_3$) | 8.0 | 17 | 14 | 16 | 13 | 23 | 15 |
| 177 | 15% ester mixture of Method W 100 val % of ammonia | 20% kaolin | 5.5 | 44 | 18 | 39 | 18 | 100 | 94 |
| 178 | 15% amide mixture of Method Y 50 val % of ammonia | 20% kaolin | 5.5 | 30 | 20 | 25 | 24 | 109 | 96 |
| 179* | 15% ester mixture of Method W 100 val % of ammonia | —* | 6.5 | 29 | 20 | 15 | 11 | 19 | 14 |
| 180* | 15% amide mixture of Method Y 50 val % of ammonia | —* | 6.5 | 69 | 44 | 17 | 12 | 53 | 23 |

*The dispersion of the fibres used in Examples 179 and 180 contains a bleached birch sulfate pulp, a bleached pine sulfate pulp and mechanical wood pulp in a weight ratio of 1:1:2 but no filler.
Similar results are obtained when the retention aid is the first to be added to the dispersion of the fibres, followed after 10 seconds by the sizing agent.

Examples 181 to 184

The method of Examples 54 to 75 is repeated, except that the sizing agent and the retention aid are added the solids content of the dispersion of the fibres. sizing results can also be seen from the following Table XIV.

Examples 186 to 188 and Comparative Test II

TABLE XIV

| Example No. | Sizing agent | Amount of sizing agent (%) | Retention aid | Amount of retention aid (%) | pH value of the dispersion of the fibres | WA Cobb$_{30}$ (g/m$^2$) after drying | | | |
|---|---|---|---|---|---|---|---|---|---|
| | | | | | | immediately | | after 1 day storage | |
| | | | | | | SS | OS | SS | OS |
| 181 | according to Method T* | 0.5 | No. 6 | 0.25 | 8.4 | 34 | 13 | 18 | 10 |
| 182 | according to Method DD** | 0.5 | No. 6 | 1.0 | 8.5 | 39 | 15 | 30 | 11 |
| 183 | according to Example 22*** | 0.5 | No. 6 | 1.0 | 8.5 | 17 | 12 | 14 | 11 |
| 184 | according to Example 22*** | 0.5 | No. 7 | 1.0 | 8.8 | 20 | 15 | 16 | 12 |

*as a dilutable, homogeneous, long-shelf-life formulation of the sizing agent, which has been emulsified in the molten state with 58 val % of sodium hydroxide in the presence of water at 80° C.
**as a dilutable, homogeneous, long-shelf-life formulation of the sizing agent, which has been emulsified in the molten state with 89 val % of sodium hydroxide in the presence of water at 80° C.
***as a dilutable, homogeneous, long-shelf-life formulation of the sizing agent, which has been dispersed in powder form with 68 val % ammonia in the presence of water and glass beads at room temperature (15 to 25° C.).

Example 185 and Comparative Test I

The method of Examples 54 to 75 is repeated, except that the sizing agent and the retention aid are added separately to the dispersion of the fibres and that no PERCOL 292 ® used as an auxiliary. As the filler, there is added 20% of chalk to the dispersion of the fibres. The addition of the sizing agent is carried out 10 seconds after the addition of the chalk and the addition of the retention aid 10 seconds after the addition of the sizing agent. As the sizing agents, there is used a 35% dilutable, homogeneous and long-shelf-life formulation of the ester mixture in the molten state obtained according to Method T which is emulsified with 58 val % of sodium hydroxide in the presence of water at 80° C. Retention aid No. 8 is used instead of the retention aids Nos. 1 to 3. Retention aid No. 8 is an epichlorohydrin adduct of a poly-N-methyldiallylamine which is prepared as in Example 1 of U.S. Pat. No. 4,279,794. The sizing agents and retention aids are used in the amounts which are indicated in the following Table XV, these amounts and the amount of filler (20% of chalk) being based on dry matter of sizing agent, retention aid and filler and on the solids content of the dispersion of the fibres. The sizing results can be seen from the following Table XV.

In addition, the whitness is assessed by measurement of the reflectance values according to the standard test T 452 of TAPPI (Technical A/ssociation of the Pulp and Paper Industry). The higher the reflectance values, the better the whitness of the paper.

The method of Examples 54 to 75 is repeated, except that the sizing agent and the retention aid are added separately to the dispersion of the fibres and that there is additionally used as a fluorescent brightening agent 0.075% of the diethanolamine salt of the 4,4'-bis[2-(di-β-hydroxyethylamino)-4-(p-sulfophenylamino)-1,3,5-triazin(6)-yl-amino]-stilbene-2,2'-disulfonic acid. As the filler, there is added 20% of chalk to the dispersion of the fibres. The addition of the chalk is carried out 1 minute after the addition of the fluorescent brightening agent, the addition of the sizing agent 10 seconds after the addition of the chalk, the addition of the retention aid 10 seconds after the addition of the sizing agent and the addition of PERCOL 292 ® 10 seconds after the addition of the retention aid. As the sizing agents, there are used the emulsions and dispersions which are indicated in the following Table XVI. Retention aid No. 8 is used instead of one of the retention aids Nos. 1 to 3. The sizing agents and retention aids are used in the amounts which are indicated in the following Table XVI, these amounts, the amount of fluorescent brightening agent (0.075%) and the amount of filler (20% of chalk) being based on dry matter of fluorescent brightening agent, sizing agent, retention aid and filler and on the solids content of the dispersion of the fibres. The sizing results can also be seen from the following Table XVI.

The whitness is assessed by measurement of the reflectance values according to the standard test T 452 of TAPPI.

TABLE XV

| Example No. or comparative test No. | Amount of sizing agent (%) | Amount of retention aid (%) | pH-value of the dispersion of the fibres | WA Cobb$_{30}$ (g/m$^2$) after drying | | | | Whiteness (reflectance values) |
|---|---|---|---|---|---|---|---|---|
| | | | | immediately | | after 1 day storage | | |
| | | | | SS | OS | SS | OS | |
| Example 185 | 0.5 | 0.25 | 8.8 | 17 | 12 | 16 | 11 | 67.9 |
| Comparative test I | 0 | 0 | — | — | 161 | — | 169 | 67.1 |

TABLE XVI

| Example No. or comparative test No. | Amount of sizing agent (%) | Sizing agent | Amount of retention aid (%) | pH-value of the dispersion of the fibres | WA Cobb$_{30}$ (g/m$^2$) after drying | | | | | Whitness (reflectance values) |
|---|---|---|---|---|---|---|---|---|---|---|
| | | | | | immediately | | after 1 day storage | | after 2 weeks storage | |
| | | | | | SS | OS | SS | OS | SS | |
| Example 186 | 0.5 | according to Method T* | 0.25 | 9.0 | 22 | 14 | 21 | 12 | 22 | 73.0 |
| Example 187 | 0.5 | according to Method DD** | 0.25 | 9.0 | 26 | 14 | 24 | 12 | 26 | 72.5 |

TABLE XVI-continued

| Example No. or comparative test No. | Amount of sizing agent (%) | Sizing agent | Amount of retention aid (%) | pH-value of the dispersion of the fibres | WA Cobb30 (g/m²) after drying | | | | | Whitness (reflectance values) |
|---|---|---|---|---|---|---|---|---|---|---|
| | | | | | immediately | | after 1 day storage | | after 2 weeks storage | |
| | | | | | SS | OS | SS | OS | SS | |
| Example 188 | 0.5 | according to Example 22*** | 0.25 | 9.0 | 21 | 12 | 18 | 10 | 17 | 72.3 |
| Comparative test II | 0 | — | 0 | — | — | 153 | — | 146 | 147 | 74.4 |

*as a dilutable, homogeneous, long-shelf-life formulation of the sizing agent, which has been emulsified in the molten state with 58 val % of sodium hydroxide in the presence of water at 80° C.
**as a dilutable, homogeneous, long-shelf-life formulation of the sizing agent, which has been emulsified in the molten state with 89 val % of sodium hydroxide in the presence of water at 80° C.
*as a dilutable, homogeneous, long-shelf-life formulation of the sizing agent, which has been dispersed in powder form with 68 val % ammonium in the presence of water and glass beads at room temperature (15° to 25° C.).

Comparative Tests III to V

The method of Examples 112 to 116 is repeated, except that Comparative test III is carried out with 0.5% of retention aid No. 5 without sizing agent, Comparative IV with 0.5% of the specified sizing agent without retention aid and Comparative test V without sizing agent or retention aid, affording only poor sizing of the paper, as is evident from the WA Cobb values above 100 given in Table XVII below.

TABLE XVII

| Comparative Test No. | pH-value of the dispersion of the fibres | WA Cobb30 (g/m²) after drying | | | |
|---|---|---|---|---|---|
| | | immediately | | after 1 day storage | |
| | | SS | OS | SS | OS |
| III | 8.1 | 191 | 154 | 162 | 148 |
| IV | 8.0 | 173 | 146 | 150 | 124 |
| V | 8.1 | 240 | 196 | 197 | 176 |

What is claimed is:

1. A process for sizing paper or cardboard, which comprises adding to an aqueous dispersion of cellulose fibers, in any order or simultaneously at least
   (A) 0.02 to 3% by weight of a sizing agent which contains one acidic group selected from the group consisting of $-P(=O)(OH)_2$, $-COOH$ and $-SO_3H$ which is either free or in the form of a salt and at least two hydrophobic substituents which each have at least 5 carbon atoms, and at least one of the hydrophobic substituents having at least 8 carbon atoms, and at least two adjacent hydrophobic substituents being bonded to each other with a linking member of the formula $$-Q_1-(O)-A_1-(O)_{m-1}-Q_2- \quad (1)$$

or $$-O-A_2-O- \quad (2)$$

wherein m is 1 or 2, $A_1$ is a divalent aliphatic or cycloaliphatic radical, $A_2$ is a divalent aromatic radical and $Q_1$ and $Q_2$ are

wherein the linking member has 4 to 15 carbon atoms and 2 hetero atoms and the sizing agent has a molecular weight of 400 to 3000, and
   (B) 0.02 to 3% by weight of a polymeric cationic retention aid.

2. A process of claim 1, wherein the component (A) sizing agent contains at least two hydrophobic substituents which each have at least 8 carbon atoms.

3. A process of claim 2, wherein the component (A) sizing agent is monomeric or oligomeric.

4. A process of claim 1, wherein the hydrophobic substituents of the component (A) sizing agent each have 8 to 22 carbon atoms.

5. A process of claim 1, wherein the component (A) sizing agent contains 1 to 6 anionic groups which each have one or two negative charges and 2 to 10 hydrophobic substituents, at least two adjacent hydrophobic substituents being bonded to each other with 1 to 5 linking members which each have 4 to 15 carbon atoms and at least two oxygen and/or nitrogen atoms.

6. A process of claim 1, wherein the component (A) sizing agent is obtainable by reacting (a) an aliphatic alcohol having 3 to 26 carbon atoms and 2 to 6 hydroxyl or hydroxy-$C_1$-$C_4$-alkyl groups, 0 to 5 nitrogen atoms, and in the presence of 2 hydroxy groups an optional $C_6$-$C_{22}$ fatty amine group; a heterocylic alcohol or glycide having 3 nitrogen atoms in the hetero ring and 3 hydroxy-$C_1$-$C_4$-alkyl or glycide groups; an alkandiol diglycide having 2 to 6 carbon atoms in the alkane radical; a diphenol; a triphenol; or a dihydroxynaphthalene with (b) a fatty acid, a halide thereof or a primary or secondary fatty amine having 6 to 22 carbon atoms in the fatty radical, and then with (c) a polybasic inorganic acid or an organic acid having 2 to 18 carbon atoms or an anhydride thereof.

7. A process of claim 1, wherein the component (A) sizing agent is obtainable by reacting
   (a) 1,5-, 1,8-, 2,3- or 2,7-dihydroxynaphthalene, pyrogallol, hydroxyhydroquinone, phloroglucine, hydroquinone, pyrocatechol, resorcinol, tris(hydroxyethyl) isocyanurate, butane-1,4-dioldiglycide, glycerol, butane-1,2,4-triol, pentaerythritol, sorbitol, sorbitan, triethanolamine, a $C_8$-$C_{22}$ fatty amine diethoxylate, N,N,N',N'-tetrakis(2-hydroxypropyl-)ethylemediamine or tris(hydroxymethyl-)aminomethane with
   (b) a fatty acid having 16 to 20 carbon atoms or an alkyl halide or alkenyl halide or a monoalkylamine, dialkylamine, monoalkenylamine or dialkenylamine which has 16 to 20 carbon atoms in the alkyl or alkenyl radical and then with (c) sulfur trioxide, sulfuric acid, chlorosulfonic acid, phosphoric acid, phosphorus pentoxide, phthalic anhydride, succinic anhydride or maleic anhydride.

8. A process of claim 1, wherein component (B) retention aid has a molecular weight of 1,000 to 2,000,000.

9. A process of claim 1, wherein the component (B) retention aid is a polyalkyleneimine, an epihalogenohydrin adduct of reaction products of polyalkylenepolyamines and aliphatic dicarboxylic acids or of reaction products of polyalkylenepolyamines, dicyanodiamide and free or alkanol-esterified organic dicarboxylic acids, reaction products of dicyanodiamide, formaldehyde, ammonium salts of strong inorganic acids and alkylenediamines or polyalkylenepolyamines, cationically modified starches or carbohydrates from carob bean or guar bean flour, reaction products of epihalogenohydrins and polymerised diallylamines or copolymers based on polyamide-amines.

10. A process of claim 1, wherein the fiber dispersion further contains a filler selected from the group consisting of condensation products of formaldehyde and urea, titanium dioxide, calcium sulfate, talc, kaolin, montmorillonite and chalk.

11. Paper or cardboard which is sized by the process of claim 1.

* * * * *